US007364740B2

(12) United States Patent
Behr et al.

(10) Patent No.: US 7,364,740 B2
(45) Date of Patent: Apr. 29, 2008

(54) **MOLECULAR DIFFERENCES BETWEEN SPECIES OF THE *M. TUBERCULOSIS* COMPLEX**

(75) Inventors: Marcel Behr, Montreal (CA); Peter Small, Seattle, WA (US); Gary Schoolnik, Stanford, CA (US); Michael A. Wilson, Bethesda, MD (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 323 days.

(21) Appl. No.: 11/143,401

(22) Filed: Jun. 1, 2005

(65) Prior Publication Data

US 2006/0002953 A1 Jan. 5, 2006

Related U.S. Application Data

(63) Continuation of application No. 10/647,089, filed on Aug. 21, 2003, now abandoned, which is a continuation of application No. 09/894,844, filed on Jun. 27, 2001, now Pat. No. 6,686,166, which is a continuation of application No. 09/318,191, filed on May 25, 1999, now Pat. No. 6,291,190.

(60) Provisional application No. 60/097,936, filed on Aug. 25, 1998.

(51) Int. Cl.

| | |
|---|---|
| ***A61K 48/00*** | (2006.01) |
| ***A61K 39/02*** | (2006.01) |
| ***A61K 39/04*** | (2006.01) |
| ***C12N 1/21*** | (2006.01) |
| ***C12N 15/63*** | (2006.01) |
| *C07H 21/04* | (2006.01) |

(52) U.S. Cl. ................. 424/185.1; 424/93.1; 424/93.2; 424/93.4; 424/184.1; 424/190.1; 424/192.1; 424/193.1; 424/197.11; 424/234.1; 424/248.1; 435/320.1; 435/252.3; 435/253.1; 514/2

(58) Field of Classification Search ..................... None
See application file for complete search history.

(56) References Cited

U.S. PATENT DOCUMENTS

| | | | | |
|---|---|---|---|---|
| 5,134,142 A * | 7/1992 | Matsuo et al. | ......... | 514/253.09 |
| 5,686,597 A | 11/1997 | Coleman et al. | | |
| 5,700,683 A | 12/1997 | Stover | | |
| 5,776,465 A | 7/1998 | O'Donnell et al. | | |
| 5,955,356 A | 9/1999 | Content et al. | | |
| 6,291,190 B1 | 9/2001 | Behr et al. | .................. | 435/7.1 |

FOREIGN PATENT DOCUMENTS

| | | |
|---|---|---|
| WO | WO 96/27129 | 2/1996 |
| WO | WO 96/25519 | 8/1996 |
| WO | WO 01/04151 | 1/2001 |

OTHER PUBLICATIONS

Medina et al., J. Exp. Med., 1996, vol. 183, pp. 1045-1051.*
Sable et al., Clinical Immunology, 2007, vol. 122, pp. 239-251.*
Orme, Vaccine, 2006, vol. 24, pp. 2-19.*
Doherty et al., Clin. Microbiol. Rev., 2005, vol. 18, No. 4, pp. 687-702.*
Agger et al., Vaccine, 2002, vol. 21, pp. 7-14.*
Rook et al., Vaccine, 2005, vol. 23, pp. 2115-2120.*
Aldovini, et al., (1993) *Journal of Bacteriology*, vol. 175:7282-7289.
Behr et al., (May 1999) *Science*, vol. 284:1520-1523.
Brosch et al., (May 1998) *Ibfection & Immunity*, vol. 66(5):2221-2229.
Cole, et al., (1998) *Nature*, vol. 393:537-544.
Converse, et al., (1996) *Infection and Immunity*, vol. 64, No. (11):4776-4787.
Delahunty, et al., (1996) *American Journal of Human Genetics*, vol. 58:1239-1246.
DeRisi, et al., (1996) *Nature Genetics*, vol. 14:457-460.
Ganjam, et al., (1991) *P.N.A.S.*, vol. 88:5433-5437.
Gordon et al., (Apr. 1999) *Molecular Microbiology*, vol. 32(3):643-655.
Hacia, et al., (1996) *Nature Genetics*, vol. 14:441-447.
Jost, et al., (1994) *Journal of Biochemistry*, vol. 269:26267-73.
Lockhart, et al., (1996) *Nature Biotechnology*, vol. 14:1675-1680.
Mahairas, et al., (1996) *Journal of Bacteriology*, vol. 178, No. (5):1274-1282.
Norman, et al., (1995) *Molecular Microbiology*, vol. 16:755-760.
Paul, et al., (1996) *journal of Infectious Diseases*, vol. 174, No. (1):105-112.
Philip, W. et al., (1996) *Microbiology*, vol. 142:3135-3145.
Ramsay, et al., (1998) *Nature Biotechnology*, vol. 16:40-44.
Riley, et al., (1990) *Nucleic Acids Research*, vol. 18:2887-2890.
Saiki, et al., (1985) *Science*, vol. 239:487-491.
Sambrook, et al., *Molecular Cloning: A Laboratory Manual, CSH Press* (1989), pp. 14.2-14.33.
Shalon, et al., (1996) *Genome Research*, vol. 6:639-645.
Silver, et al., (1998) *Infection and Immunology*, vol. 66, No. (3):1190-1199.
Talbot, et al., (1997) *Journal of Clinical Microbiology*, vol. 35:566-569.
Brosch et al. Infection and Immunity, May 1998, vol. 66, No. 5, pp. 2221-2229.
Mahairas et al. Journal of Bacteriology, Mar. 1996, vol. 178, No. 5, pp. 1274-1282.
Cole, et al. Nature, Jun. 1998, vol. 393, pp. 537-544.
Cole, et al. Nature, Nov. 1998, vol. 396, Errata, pp. 190-198.
Gordon et al. Molecular Microbiology, Apr. 1999, vol. 32, No. 3, pp. 643-655.
Behr et al. Science, May 1999, vol. 284, pp. 1520-1523.

* cited by examiner (Continued)

*Primary Examiner*—David Guzo
(74) *Attorney, Agent, or Firm*—Bozicevic, Field & Francis LLP; Pamela J. Sherwood

(57) ABSTRACT

Specific genetic deletion are identified in mycobacteria isolates, including variations in the *M. tuberculosis* genome sequence between isolates, and numerous deletion present in BCG as compared to M. tb. These deletions are used as markers to distinguish between pathogenic and avirulent strains, and as a marker for particular M. tb isolates. Deletions specific to vaccine strains of BCG are useful in determining whether a positive tuberculin skin test is indicative of actual tuberculosis infection. The deleted sequences may be re-introduced into BCG to improve the efficacy of vaccination. Alternatively, the genetic sequence that corresponds to the deletion(s) are deleted from *M. bovis* or *M. tuberculosis* to attenuate the pathogenic bacteria.

15 Claims, No Drawings

MOLECULAR DIFFERENCES BETWEEN SPECIES OF THE *M. TUBERCULOSIS* COMPLEX

This invention was made with Government support under contract AI01137 and AI135969 awarded by the National Institutes of Health. The Government has certain rights in this invention.

Tuberculosis is an ancient human scourge that continues to be an important public health problem worldwide. It is an ongoing epidemic of staggering proportions. Approximately one in every three people in the world is infected with *Mycobacterium tuberculosis*, and has a 10% lifetime risk of progressing from infection to clinical disease. Although tuberculosis can be treated, an estimated 2.9 million people died from the disease last year.

There are significant problems with a reliance on drug treatment to control active *M. tuberculosis* infections. Most of the regions having high infection rates are less developed countries, which suffer from a lack of easily accessible health services, diagnostic facilities and suitable antibiotics against *M. tuberculosis*. Even where these are available, patient compliance is often poor because of the lengthy regimen required for complete treatment, and multidrug-resistant strains are increasingly common.

Prevention of infection would circumvent the problems of treatment, and so vaccination against tuberculosis is widely performed in endemic regions. Around 100 million people a year are vaccinated with live bacillus Calmette-Guerin (BCG) vaccine. BCG has the great advantage of being inexpensive and easily administered under less than optimal circumstances, with few adverse reactions. Unfortunately, the vaccine is widely variable in its efficacy, providing anywhere from 0 to 80% protection against infection with *M. tuberculosis*.

BCG has an interesting history. It is an attenuated strain of *M. bovis*, a very close relative of *M. tuberculosis*. The *M. bovis* strain that became BCG was isolated from a cow in the late 1800's by a bacteriologist named Nocard, hence it was called Nocard's bacillus. The attenuation of Nocard's bacillus took place from 1908 to 1921, over the course of 230 in vitro passages. Thereafter, it was widely grown throughout the world, resulting in additional hundreds and sometime thousands of in vitro passages. Throughout its many years in the laboratory, there has been selection for cross-reaction with the tuberculin skin test, and for decreased side effects. The net results have been a substantially weakened pathogen, which may be ineffective in raising an adequate immune response.

New antituberculosis vaccines are urgently needed for the general population in endemic regions, for HIV-infected individuals, as well as health care professionals likely to be exposed to tubercle bacilli. Recombinant DNA vaccines bearing protective genes from virulent *M. tuberculosis* are being developed using shuttle plasmids to transfer genetic material from one mycobacterial species to another, for example see U.S. Pat. No. 5,776,465. Tuberculosis vaccine development should be given a high priority in current medical research goals.

Relevant Literature

Mahairas et al. (1996) *J Bacteriol* 178(5):1274-1282 provides a molecular analysis of genetic differences between *Mycobacterium bovis* BCG and virulent *M. bovis*. Subtractive genomic hybridization was used to identify genetic differences between virulent *M. bovis* and *M. tuberculosis* and avirulent BCG. U.S. Pat. No. 5,700,683 is directed to these genetic differences.

Cole et al. (1998) *Nature* 393:537-544 have described the complete genome of *M. tuberculosis*. To obtain the contiguous genome sequence, a combined approach was used that involved the systematic sequence analysis of selected large-insert clones as well as random small-insert clones from a whole-genome shotgun library. This culminated in a composite sequence of 4,411,529 base pairs, with a G+C content of 65.6%. 3,924 open reading frames were identified in the genome, accounting for ~91% of the potential coding capacity.

*Mycobacterium tuberculosis* (*M.tb.*) genomic sequence is available at several internet sites.

SUMMARY OF THE INVENTION

Genetic markers are provided that distinguish between strains of the *Mycobacterium tuberculosis* complex, particularly between avirulent and virulent strains. Strains of interest include *M. bovis, M. bovis* BCG strains, *M. tuberculosis* (*M. tb.*) isolates, and bacteriophages that infect mycobacteria. The genetic markers are used for assays, e.g. immunoassays, that distinguish between strains, such as to differentiate between BCG immunization and M. tb. infection. The protein products may be produced and used as an immunogen, in drug screening, etc. The markers are useful in constructing genetically modified M. tb or *M. bovis* cells having improved vaccine characteristics.

DETAILED DESCRIPTION OF THE EMBODIMENTS

Specific genetic deletions are identified that serve as markers to distinguish between avirulent and virulent mycobacteria strains, including *M. bovis, M. bovis* BCG strains, *M. tuberculosis* (*M. tb.*) isolates, and bacteriophages that infect mycobacteria. These deletions are used as genetic markers to distinguish between the different mycobacteria. The deletions may be introduced into M. tb. or *M. bovis* by recombinant methods in order to render a pathogenic strain avirulent. Alternatively, the deleted genes are identified in the M. tb. genome sequence, and are then reintroduced by recombinant methods into BCG or other vaccine strains, in order to improve the efficacy of vaccination.

The deletions of the invention are identified by comparative DNA hybridizations from genomic sequence of *mycbacterium* to a DNA microarray comprising representative sequences of the M. tb. coding sequences. The deletions are then mapped to the known M. tb. genome sequence in order to specifically identify the deleted gene(s), and to characterize nucleotide sequence of the deleted region.

Nucleic acids comprising the provided deletions and junctions are used in a variety of applications. Hybridization probes may be obtained from the known M. tb. sequence which correspond to the deleted sequences. Such probes are useful in distinguishing between mycobacteria. For example, there is a 10% probability that an M. tb. infected person will progress to clinical disease, but that probability may vary depending of the particular infecting strain. Analysis for the presence or absence of the deletions provided below as "M. tb variable" is used to distinguish between different M. tb strains. The deletions are also useful in identifying whether a patient that is positive for a tuberculin skin test has been infected with M. tb or with BCG.

In another embodiment of the invention, mycobacteria are genetically altered to delete sequences identified herein as absent in attenuated strains, but present in pathogenic strains, e.g. deletions found in BCG but present in M. tb H37Rv. Such genetically engineered strains may provide superior vaccines to the present BCG isolates in use. Alternatively, BCG strains may be "reconstructed" to more closely resemble wild-type M. tb by inserting certain of the deleted sequences back into the genome. Since the protein products of the deleted sequences are expressed in virulent mycobacterial species, the encoded proteins are useful as immunogens for vaccination.

The attenuation (loss of virulence) in BCG is attributed to the loss of genetic material at a number of places throughout the genome. The selection over time for fewer side-effects resulting from BCG immunization, while retaining cross-reactivity with the tuberculin skin test, has provided an excellent screen for those sequences that engender side effects. The identification of deletions that vary between BCG isolates identifies such sequences, which may be used in drug screening and biological analysis for the role of the deleted genes in causing untoward side effects and pathogenicity.

Identification of *M Tuberculosis* Complex Deletion Markers

The present invention provides nucleic acid sequences that are markers for specific mycobacteria, including M. tb., *M. bovis*, BCG and bacteriophage. The deletions are listed in Table 1. The absence or presence of these marker sequences is characteristic of the indicated isolate, or strain. As such, they provide a unique characteristic for the identification of the indicated mycobacteria. The deletions are identified by their M. tb. open reading frame ("Rv" nomenclature), which corresponds to a known genetic sequence, and may be accessed as previously cited. The junctions of the deletions are provided by the designation of position in the publicly available M. tb. sequence.

TABLE 1

| SEQ ID | rd | rv_num | orf_id | breakpoint |
|---|---|---|---|---|
| SEQ ID NO: 1 | RD01 | Rv3871 | MTV027.06 | "H37Rv, segment 160: 7534, 16989" |
| SEQ ID NO: 2 | RD01 | Rv3872 | MTV027.07 | "H37Rv, segment 160: 7534, 16989" |
| SEQ ID NO: 3 | RD01 | Rv3873 | MTV027.08 | "H37Rv, segment 160: 7534, 16989" |
| SEQ ID NO: 4 | RD01 | Rv3874 | MTV027.09 | "H37Rv, segment 160: 7534, 16989" |
| SEQ ID NO: 5 | RD01 | Rv3875 | MTV027.10 | "H37Rv, segment 160: 7534, 16989" |
| SEQ ID NO: 6 | RD01 | Rv3876 | MTV027.11 | "H37Rv, segment 160: 7534, 16989" |
| SEQ ID NO: 7 | RD01 | Rv3877 | MTV027.12 | "H37Rv, segment 160: 7534, 16989" |
| SEQ ID NO: 8 | RD01 | Rv3878 | MTV027.13 | "H37Rv, segment 160: 7534, 16989" |
| SEQ ID NO: 9 | RD01 | Rv3879c | MTV027.14c | "H37Rv, segment 160: 7534, 16989" |
| SEQ ID NO: 10 | RD02 | Rv1988 | MTCY39.31c | "H37Rv segment 88: 14211, segment 89: 8598" |
| SEQ ID NO: 11 | RD02 | Rv1987 | MTCY39.32c | "H37Rv segment 88: 14211, segment 89: 8598" |
| SEQ ID NO: 12 | RD02 | Rv1986 | MTCY39.33c | "H37Rv segment 88: 14211, segment 89: 8598" |
| SEQ ID NO: 13 | RD02 | Rv1985c | MTCY39.34 | "H37Rv segment 88: 14211, segment 89: 8598" |
| SEQ ID NO: 14 | RD02 | Rv1984c | MTCY39.35 | "H37Rv segment 88: 14211, segment 89: 8598" |
| SEQ ID NO: 15 | RD02 | Rv1983 | MTCY39.36c | "H37Rv segment 88: 14211, segment 89: 8598" |
| SEQ ID NO: 16 | RD02 | Rv1982c | MTCY39.37 | "H37Rv segment 88: 14211, segment 89: 8598" |
| SEQ ID NO: 17 | RD02 | Rv1981c | MTCY39.38 | "H37Rv segment 88: 14211, segment 89: 8598" |
| SEQ ID NO: 18 | RD02 | Rv1980c | MTCY39.39 | "H37Rv segment 88: 14211, segment 89: 8598" |
| SEQ ID NO: 19 | RD02 | Rv1979c | MTCY39.40 | "H37Rv segment 88: 14211, segment 89: 8598" |
| SEQ ID NO: 20 | RD02 | Rv1978 | MTV051.16 | "H37Rv segment 88: 14211, segment 89: 8598" |
| SEQ ID NO: 21 | RD03 | Rv1586c | MTCY336.18 | "H37Rv, segment 70: 7677, 16923" |
| SEQ ID NO: 22 | RD03 | Rv1585c | MTCY336.19 | "H37Rv, segment 70: 7677, 16923" |
| SEQ ID NO: 23 | RD03 | Rv1584c | MTCY336.20 | "H37Rv, segment 70: 7677, 16923" |
| SEQ ID NO: 24 | RD03 | Rv1583c | MTCY336.21 | "H37Rv, segment 70: 7677, 16923" |
| SEQ ID NO: 25 | RD03 | Rv1582c | MTCY336.22 | "H37Rv, segment 70: 7677, 16923" |
| SEQ ID NO: 26 | RD03 | Rv1581c | MTCY336.23 | "H37Rv, segment 70: 7677, 16923" |
| SEQ ID NO: 27 | RD03 | Rv1580c | MTCY336.24 | "H37Rv, segment 70: 7677, 16923" |
| SEQ ID NO: 28 | RD03 | Rv1579c | MTCY336.25 | "H37Rv, segment 70: 7677, 16923" |
| SEQ ID NO: 29 | RD03 | Rv1578c | MTCY336.26 | "H37Rv, segment 70: 7677, 16923" |
| SEQ ID NO: 30 | RD03 | Rv1577c | MTCY336.27 | "H37Rv, segment 70: 7677, 16923" |
| SEQ ID NO: 31 | RD03 | Rv1576c | MTCY336.28 | "H37Rv, segment 70: 7677, 16923" |
| SEQ ID NO: 32 | RD03 | Rv1575 | MTCY336.29c | "H37Rv, segment 70: 7677, 16923" |
| SEQ ID NO: 33 | RD03 | Rv1574 | MTCY336.30c | "H37Rv, segment 70: 7677, 16923" |
| SEQ ID NO: 34 | RD03 | Rv1573 | MTCY336.31c | "H37Rv, segment 70: 7677, 16923" |
| SEQ ID NO: 35 | RD04 | Rv0221 | MTCY08D5.16 | "H37Rv, segment 12: 17432, 19335" |
| SEQ ID NO: 36 | RD04 | Rv0222 | MTCY08D5.17 | "H37Rv, segment 12: 17432, 19335" |
| SEQ ID NO: 37 | RD04 | Rv0223c | MTCY08D5.18 | "H37Rv, segment 12: 17432, 19335" |
| SEQ ID NO: 38 | RD05 | Rv3117 | MTCY164.27 | "H37Rv, segment 135: 27437, 30212" |
| SEQ ID NO: 39 | RD05 | Rv3118 | MTCY164.28 | "H37Rv, segment 135: 27437, 30212" |
| SEQ ID NO: 40 | RD05 | Rv3119 | MTCY164.29 | "H37Rv, segment 135: 27437, 30212" |
| SEQ ID NO: 41 | RD05 | Rv3120 | MTCY164.30 | "H37Rv, segment 135: 27437, 30212" |
| SEQ ID NO: 42 | RD05 | Rv3121 | MTCY164.31 | "H37Rv, segment 135: 27437, 30212" |
| SEQ ID NO: 43 | RD06 | Rv1506c | MTCY277.28c | "H37Rv, segment 65: 23614, 36347" |
| SEQ ID NO: 44 | RD06 | Rv1507c | MTCY277.29c | "H37Rv, segment 65: 23614, 36347" |
| SEQ ID NO: 45 | RD06 | Rv1508c | MTCY277.30c | "H37Rv, segment 65: 23614, 36347" |
| SEQ ID NO: 46 | RD06 | Rv1509 | MTCY277.31 | "H37Rv, segment 65: 23614, 36347" |
| SEQ ID NO: 47 | RD06 | Rv1510 | MTCY277.32 | "H37Rv, segment 65: 23614, 36347" |
| SEQ ID NO: 48 | RD06 | Rv1511 | MTCY277.33 | "H37Rv, segment 65: 23614, 36347" |
| SEQ ID NO: 49 | RD06 | Rv1512 | MTCY277.34 | "H37Rv, segment 65: 23614, 36347" |
| SEQ ID NO: 50 | RD06 | Rv1513 | MTCY277.35 | "H37Rv, segment 65: 23614, 36347" |
| SEQ ID NO: 51 | RD06 | Rv1514c | MTCY277.36c | "H37Rv, segment 65: 23614, 36347" |

TABLE 1-continued

| SEQ ID | rd | rv_num | orf_id | breakpoint |
|---|---|---|---|---|
| SEQ ID NO: 52 | RD06 | Rv1515c | MTCY277.37c | "H37Rv, segment 65: 23614, 36347" |
| SEQ ID NO: 53 | RD06 | Rv1516c | MTCY277.38c | "H37Rv, segment 65: 23614, 36347" |
| SEQ ID NO: 54 | RD07 | Rv2346c | MTCY98.15c | "H37Rv, segment 103: 17622, 26584" |
| SEQ ID NO: 55 | RD07 | Rv2347c | MTCY98.16c | "H37Rv, segment 103: 17622, 26584" |
| SEQ ID NO: 56 | RD07 | Rv2348c | MTCY98.17c | "H37Rv, segment 103: 17622, 26584" |
| SEQ ID NO: 57 | RD07 | Rv2349c | MTCY98.18c | "H37Rv, segment 103: 17622, 26584" |
| SEQ ID NO: 58 | RD07 | Rv2350c | MTCY98.19c | "H37Rv, segment 103: 17622, 26584" |
| SEQ ID NO: 59 | RD07 | Rv2351c | MTCY98.20c | "H37Rv, segment 103: 17622, 26584" |
| SEQ ID NO: 60 | RD07 | Rv2352c | MTCY98.21c | "H37Rv, segment 103: 17622, 26584" |
| SEQ ID NO: 61 | RD07 | Rv2353c | MTCY98.22c | "H37Rv, segment 103: 17622, 26584" |
| SEQ ID NO: 62 | RD08 | Rv0309 | MTCY63.14 | "H37Rv, segment 16: 17018, 20446" |
| SEQ ID NO: 63 | RD08 | Rv0310c | MTCY63.15c | "H37Rv, segment 16: 17018, 20446" |
| SEQ ID NO: 64 | RD08 | Rv0311 | MTCY63.16 | "H37Rv, segment 16: 17018, 20446" |
| SEQ ID NO: 65 | RD08 | Rv0312 | MTCY63.17 | "H37Rv, segment 16: 17018, 20446" |
| SEQ ID NO: 66 | RD09 | Rv3623 | MTCY15C10.29c | "H37Rv, segment 153: 21131, segment 154: 2832" |
| SEQ ID NO: 67 | RD09 | Rv3622c | MTCY15C10.30 | "H37Rv, segment 153: 21131, segment 154: 2832" |
| SEQ ID NO: 68 | RD09 | Rv3621c | MTCY15C10.31 | "H37Rv, segment 153: 21131, segment 154: 2832" |
| SEQ ID NO: 69 | RD09 | Rv3620c | MTCY15C10.32 | "H37Rv, segment 153: 21131, segment 154: 2832" |
| SEQ ID NO: 70 | RD09 | Rv3619c | MTCY15C10.33 | "H37Rv, segment 153: 21131, segment 154: 2832" |
| SEQ ID NO: 71 | RD09 | Rv3618 | MTCY15C10.34c | "H37Rv, segment 153: 21131, segment 154: 2832" |
| SEQ ID NO: 72 | RD09 | Rv3617 | MTCY15C10.35c | "H37Rv, segment 153: 21131, segment 154: 2832" |
| SEQ ID NO: 73 | RD10 | Rv1257c | MTCY50.25 | "H37Rv segment 55: 3689, 6696" |
| SEQ ID NO: 74 | RD10 | Rv1256c | MTCY50.26 | "H37Rv segment 55: 3689, 6696" |
| SEQ ID NO: 75 | RD10 | Rv1255c | MTCY50.27 | "H37Rv segment 55: 3689, 6696" |
| SEQ ID NO: 76 | RD11 | Rv3429 | MTCY77.01 | "H37Rv, segment 145: 30303 to segment 146: 1475" |
| SEQ ID NO: 77 | RD11 | Rv3428c | MTCY78.01 | "H37Rv, segment 145: 30303 to segment 146: 1475" |
| SEQ ID NO: 78 | RD11 | Rv3427c | MTCY78.02 | "H37Rv, segment 145: 30303 to segment 146: 1475" |
| SEQ ID NO: 79 | RD11 | Rv3426 | MTCY78.03c | "H37Rv, segment 145: 30303 to segment 146: 1475" |
| SEQ ID NO: 80 | RD11 | Rv3425 | MTCY78.04c | "H37Rv, segment 145: 30303 to segment 146: 1475" |
| SEQ ID NO: 81 | RD12 | Rv2072c | MTCY49.11c | "H37Rv segment 93: 9301, 11331" |
| SEQ ID NO: 82 | RD12 | Rv2073c | MTCY49.12c | "H37Rv segment 93: 9301, 11331" |
| SEQ ID NO: 83 | RD12 | Rv2074 | MTCY49.13 | "H37Rv segment 93: 9301, 11331" |
| SEQ ID NO: 84 | RD12 | Rv2075c | MTCY49.14c | "H37Rv segment 93: 9301, 11331" |
| SEQ ID NO: 85 | RD13bis | Rv2645 | MTCY441.15 | "H37Rv, segment 118: 12475, 23455" |
| SEQ ID NO: 86 | RD13bis | Rv2646 | MTCY441.16 | "H37Rv, segment 118: 12475, 23455" |
| SEQ ID NO: 87 | RD13bis | Rv2647 | MTCY441.17 | "H37Rv, segment 118: 12475, 23455" |
| SEQ ID NO: 88 | RD13bis | Rv2648 | MTCY441.17A | "H37Rv, segment 118: 12475, 23455" |
| SEQ ID NO: 89 | RD13bis | Rv2649 | MTCY441.18 | "H37Rv, segment 118: 12475, 23455" |
| SEQ ID NO: 90 | RD13bis | Rv2650c | MTCY441.19 | "H37Rv, segment 118: 12475, 23455" |
| SEQ ID NO: 91 | RD13bis | Rv2651c | MTCY441.20c | "H37Rv, segment 118: 12475, 23455" |
| SEQ ID NO: 92 | RD13bis | Rv2652c | MTCY441.21c | "H37Rv, segment 118: 12475, 23455" |
| SEQ ID NO: 93 | RD13bis | Rv2653c | MTCY441.22c | "H37Rv, segment 118: 12475, 23455" |
| SEQ ID NO: 94 | RD13bis | Rv2654c | MTCY441.23c | "H37Rv, segment 118: 12475, 23455" |
| SEQ ID NO: 95 | RD13bis | Rv2655c | MTCY441.24c | "H37Rv, segment 118: 12475, 23455" |
| SEQ ID NO: 96 | RD13bis | Rv2656c | MTCY441.25c | "H37Rv, segment 118: 12475, 23455" |
| SEQ ID NO: 97 | RD13bis | Rv2657c | MTCY441.26c | "H37Rv, segment 118: 12475, 23455" |
| SEQ ID NO: 98 | RD13bis | Rv2658c | MTCY441.27c | "H37Rv, segment 118: 12475, 23455" |
| SEQ ID NO: 99 | RD13bis | Rv2659c | MTCY441.28c | "H37Rv, segment 118: 12475, 23455" |
| SEQ ID NO: 100 | RD13bis | Rv2660c | MTCY441.29c | "H37Rv, segment 118: 12475, 23455" |
| SEQ ID NO: 101 | RD14 | Rv1766 | MTCY28.32 | "H37Rv segment 79: 30573, 39642" |
| SEQ ID NO: 102 | RD14 | Rv1767 | MTCY28.33 | "H37Rv segment 79: 30573, 39642" |
| SEQ ID NO: 103 | RD14 | Rv1768 | MTCY28.34 | "H37Rv segment 79: 30573, 39642" |
| SEQ ID NO: 104 | RD14 | Rv1769 | MTCY28.35 | "H37Rv segment 79: 30573, 39642" |
| SEQ ID NO: 105 | RD14 | Rv1770 | MTCY28.36 | "H37Rv segment 79: 30573, 39642" |
| SEQ ID NO: 106 | RD14 | Rv1771 | MTCY28.37 | "H37Rv segment 79: 30573, 39642" |
| SEQ ID NO: 107 | RD14 | Rv1772 | MTCY28.38 | "H37Rv segment 79: 30573, 39642" |
| SEQ ID NO: 108 | RD14 | Rv1773c | MTCY28.39 | "H37Rv segment 79: 30573, 39642" |
| SEQ ID NO: 109 | RD15 | Rv1963c | MTV051.01c | "H37Rv segment 88: 1153, 13873" |
| SEQ ID NO: 110 | RD15 | Rv1964 | MTV051.02 | "H37Rv segment 88: 1153, 13873" |
| SEQ ID NO: 111 | RD15 | Rv1965 | MTV051.03 | "H37Rv segment 88: 1153, 13873" |
| SEQ ID NO: 112 | RD15 | Rv1966 | MTV051.04 | "H37Rv segment 88: 1153, 13873" |
| SEQ ID NO: 113 | RD15 | Rv1967 | MTV051.05 | "H37Rv segment 88: 1153, 13873" |
| SEQ ID NO: 114 | RD15 | Rv1968 | MTV051.06 | "H37Rv segment 88: 1153, 13873" |
| SEQ ID NO: 115 | RD15 | Rv1969 | MTV051.07 | "H37Rv segment 88: 1153, 13873" |
| SEQ ID NO: 116 | RD15 | Rv1970 | MTV051.08 | "H37Rv segment 88: 1153, 13873" |
| SEQ ID NO: 117 | RD15 | Rv1971 | MTV051.09 | "H37Rv segment 88: 1153, 13873" |
| SEQ ID NO: 118 | RD15 | Rv1972 | MTV051.10 | "H37Rv segment 88: 1153, 13873" |
| SEQ ID NO: 119 | RD15 | Rv1973 | MTV051.11 | "H37Rv segment 88: 1153, 13873" |
| SEQ ID NO: 120 | RD15 | Rv1974 | MTV051.12 | "H37Rv segment 88: 1153, 13873" |
| SEQ ID NO: 121 | RD15 | Rv1975 | MTV051.13 | "H37Rv segment 88: 1153, 13873" |
| SEQ ID NO: 122 | RD15 | Rv1976c | MTV051.14 | "H37Rv segment 88: 1153, 13873" |
| SEQ ID NO: 123 | RD15 | Rv1977 | MTV051.15 | "H37Rv segment 88: 1153, 13873" |
| SEQ ID NO: 124 | RD16 | Rv3405c | MTCY78.23 | "H37Rv, segment 145: 5012, 12621" |
| SEQ ID NO: 125 | RD16 | Rv3404c | MTCY78.24 | "H37Rv, segment 145: 5012, 12621" |
| SEQ ID NO: 126 | RD16 | Rv3403c | MTCY78.25 | "H37Rv, segment 145: 5012, 12621" |
| SEQ ID NO: 127 | RD16 | Rv3402c | MTCY78.26 | "H37Rv, segment 145: 5012, 12621" |

TABLE 1-continued

| SEQ ID | rd | rv_num | orf_id | breakpoint |
|---|---|---|---|---|
| SEQ ID NO: 128 | RD16 | Rv3401 | MTCY78.27c | "H37Rv, segment 145: 5012, 12621" |
| SEQ ID NO: 129 | RD16 | Rv3400 | MTCY78.28c | "H37Rv, segment 145: 5012, 12621" |

The "Rv" column indicates public M. tb sequence, open reading frame. The BCG strains were obtained as follows:

TABLE 2

Strains employed in study of BCG phylogeny

| Name of strain | Synonym | Source | Descriptors |
|---|---|---|---|
| BCG-Russia | Moscow | ATCC | # 35740 |
| BCG-Moreau | Brazil | ATCC | # 35736 |
| BCG-Moreau | Brazil | IAF | dated 1958 |
| BCG-Moreau | Brazil | IAF | dated 1961 |
| BCG-Japan | Tokyo | ATCC | # 35737 |
| BCG-Japan | Tokyo | IAF | dated 1961 |
| BCG-Japan | Tokyo | JATA | vaccine strain |
| BCG-Japan | Tokyo | JATA | bladder cancer strain |
| BCG-Japan | Tokyo | JATA | clinical isolate- adenitis |
| BCG-Sweden | Gothenburg | ATCC | # 35732 |
| BCG-Sweden | Gothenburg | IAF | dated 1958 |
| BCG-Sweden | Gothenburg | SSI | production lot, Copenhagen |
| BCG-Phipps | Philadelphia | ATCC | # 35744 |
| BCG-Denmark | Danish 1331 | ATCC | # 35733 |
| BCG-Copenhagen | | ATCC | #27290 |
| BCG-Copenhagen | | IAF | dated 1961 |
| BCG-Tice | Chicago | vaccine | dated 1973 |
| BCG-Tice | Chicago | ATCC | # 35743 |
| BCG-Frappier | Montreal | IAF | primary lot, 1973 |
| BCG-Frappier, INH-resistant | Montreal-R | IAF | primary lot, 1973 |
| BCG-Frappier | Montreal | IAF | passage 946 |
| BCG-Connaught | Toronto | CL | bladder cancer treatment |
| BCG-Birkhaug | | ATCC | # 35731 |
| BCG-Prague | Czech | SSI | lyophilized 1968 |
| BCG-Glaxo | | vaccine | dated 1973 |
| BCG-Glaxo | | ATCC | # 35741 |
| BCG-Pasteur | | IAF | passage 888 |
| BCG-Pasteur | | IAF | dated 1961 |
| BCG-Pasteur | | IP | 1173P2-B |
| BCG-Pasteur | | IP | 1173P2-C |
| BCG-Pasteur | | IP | clinical isolate # 1 |
| BCG-Pasteur | | IP | clinical isolate # 2 |
| BCG-Pasteur | | ATCC | # 35734 |

Abbreviations: IP = Institut Pasteur, Paris, France;
IAF = Institut Armand Frappier, Laval, Canada;
ATCC = American Type Culture Collection, Rockville, Md, USA;
SSI = Statens Serum Institute, Copenhagen, Denmark;
CL = Connaught Laboratories, Willowdale, Canada,
JATA = Japanese Anti-Tuberculosis Association;
INH = isoniazid.
Canadian BCG's refers to BCG-Montreal and BCG-Toronto, the latter being derived from the former.

In performing the initial screening method, genomic DNA is isolated from two mycobacteria microbial cell cultures. The two DNA preparations are labeled, where a different label is used for the first and second microbial cultures, typically using nucleotides conjugated to a fluorochrome that emits at a wavelength substantially different from that of the fluorochrome tagged nucleotides used to label the selected probe. The strains used were the reference strain of *Mycobacterium tuberculosis* (H37Rv), other M. tb. laboratory strains, such as H37Ra, the O strain, M. tb. clinical isolates, the reference strain of *Mycobacterium bovis*, and different strains of *Mycobacterium bovis* BCG.

The two DNA preparations are mixed, and competitive hybridization is carried out to a microarray representing all of the open reading frames in the genome of the test microbe, usually H37Rv. Hybridization of the labeled sequences is accomplished according to methods well known in the art. In a preferred embodiment, the two probes are combined to provide for a competitive hybridization to a single microarray. Hybridization can be carried out under conditions varying in stringency, preferably under conditions of high stringency (e.g., 4×SSC, 10% SDS, 65° C.) to allow for hybridization of complementary sequences having extensive homology (e.g., having at least 85% sequence identity, preferably at least 90% sequence identity, more preferably having at least 95% sequence identity). Where the target sequences are native sequences the hybridization is preferably carried out under conditions that allow hybridization of only highly homologous sequences (e.g., at least 95% to 100% sequence identity).

Two color fluorescent hybridization is utilized to assay the representation of the unselected library in relation to the selected library (i.e., to detect hybridization of the unselected probe relative to the selected probe). From the ratio of one color to the other, for any particular array element, the relative abundance of that sequence in the unselected and selected libraries can be determined. In addition, comparison of the hybridization of the selected and unselected probes provides an internal control for the assay. An absence of signal from the reference strain, as compared to H37Rv, is indicative that the open reading frame is deleted in the test strain. The deletion may be further mapped by Southern blot analysis, and by sequencing the regions flanking the deletion.

Microarrays can be scanned to detect hybridization of the selected and the unselected sequences using a custom built scanning laser microscope as described in Shalon et al., *Genome Res.* 6:639 (1996). A separate scan, using the appropriate excitation line, is performed for each of the two fluorophores used. The digital images generated from the scan are then combined for subsequent analysis. For any particular array element, the ratio of the fluorescent signal from the amplified selected cell population DNA is compared to the fluorescent signal from the unselected cell population DNA, and the relative abundance of that sequence in the selected and unselected library determined.

Nucleic Acid Compositions

As used herein, the term "deletion marker", or "marker" is used to refer to those sequences of *M. tuberculosis* complex genomes that are deleted in one or more of the strains or species, as indicated in Table 1. The bacteria of the *M. tuberculosis* complex include *M. tuberculosis, M. bovis*, and BCG, inclusive of varied isolates and strains within each species. Nucleic acids of interest include all or a portion of the deleted region, particularly complete open reading frames, hybridization primers, promoter regions, etc.

The term "junction" or "deletion junction" is used to refer to nucleic acids that comprise the regions on both the 3' and the 5' sequence immediately flanking the deletion. Such junction sequences are preferably used as short primers, e.g. from about 15 nt to about 30 nt, that specifically hybridize to the junction, but not to a nucleic acid comprising the undeleted genomic sequence. For example, the deletion found in *M. bovis*, at Rv0221, corresponds to the nucleotide sequence of the *M. tuberculosis* H37Rv genome, segment 12: 17432,19335. The junction comprises the regions upstream of position 17342, and downstream of 19335, e.g. a nucleic acid of 20 nucleotides comprising the sequence from H37Rv 17332-17342 joined to 19335-19345.

Typically, such nucleic acids comprising a junction will include at least about 7 nucleotides from each flanking region, i.e. from the 3' and from the 5' sequences adjacent to the deletion, and may be about 10 nucleotides from each flanking region, up to about 15 nucleotides, or more. Amplification primers that hybridize to the junction sequence, to the deleted sequence, and to the flanking non-deleted regions have a variety of uses, as detailed below.

The nucleic acid compositions of the subject invention encode all or a part of the deletion markers. Fragments may be obtained of the DNA sequence by chemically synthesizing oligonucleotides in accordance with conventional methods, by restriction enzyme digestion, by PCR amplification, etc. For the most part, DNA fragments will be at least about 25 nt in length, usually at least about 30 nt, more usually at least about 50 nt. For use in amplification reactions, such as PCR, a pair of primers will be used. The exact composition of the primer sequences is not critical to the invention, but for most applications the primers will hybridize to the subject sequence under stringent conditions, as known in the art. It is preferable to chose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

Usually, the DNA will be obtained substantially free of other nucleic acid sequences that do not include a deletion marker sequence or fragment thereof, generally being at least about 50%, usually at least about 90% pure and are typically “recombinant”, i.e. flanked by one or more nucleotides with which it is not normally associated on a naturally occurring chromosome.

For screening purposes, hybridization probes of one or more of the deletion sequences may be used in separate reactions or spatially separated on a solid phase matrix, or labeled such that they can be distinguished from each other. Assays may utilize nucleic acids that hybridize to one or more of the described deletions.

An array may include all or a subset of the deletion markers listed in Table 1. Usually such an array will include at least 2 different deletion marker sequences, i.e. deletions located at unique positions within the locus, and may include all of the provided deletion markers. Arrays of interest may further comprise other genetic sequences, particularly other sequences of interest for tuberculosis screening. The oligonucleotide sequence on the array will usually be at least about 12 nt in length, may be the length of the provided deletion marker sequences, or may extend into the flanking regions to generate fragments of 100 to 200 nt in length. For examples of arrays, see Ramsay (1998) *Nat. Biotech.* 16:40-44; Hacia et al. (1996) *Nature Genetics* 14:441-447; Lockhart et al. (1996) *Nature Biotechnol.* 14:1675-1680; and De Risi et al. (1996) *Nature Genetics* 14:457-460.

Nucleic acids may be naturally occurring, e.g. DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-$CH_2$-5'-O-phosphonate and 3'-NH-5'-O-phosphoroamidate. Peptide nucleic acids replace the entire ribose phosphodiester backbone with a peptide linkage.

Sugar modifications are also used to enhance stability and affinity. The α-anomer of deoxyribose may be used, where the base is inverted with respect to the natural b-anomer. The 2'-OH of the ribose sugar may be altered to form 2'-O-methyl or 2'-O-allyl sugars, which provide resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Polypeptide Compositions

The specific deletion markers in Table 1 correspond to open reading frames of the M. tb genome, and therefore encode a polypeptide. The subject markers may be employed for synthesis of a complete protein, or polypeptide fragments thereof, particularly fragments corresponding to functional domains; binding sites; etc.; and including fusions of the subject polypeptides to other proteins or parts thereof. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host.

In the present specification and claims, the term “polypeptide fragments”, or variants thereof, denotes both short peptides with a length of at least two amino acid residues and at most 10 amino acid residues, oligopeptides with a length of at least 11 amino acid residues, 20 amino acid residues, 50 amino acid residues, and up to about 100 amino acid residues; and longer peptides of greater than 100 amino acid residues up to the complete length of the native polypeptide.

The term substantially pure polypeptide fragment means a polypeptide preparation which contains at most 5% by weight of other polypeptide material with which it is natively associated, and lower percentages are preferred, e.g. at most 4%, at most 3%, at most 2%, at most 1%, and at most 0.5%. It is preferred that the substantially pure polypeptide is at least 96% pure, i.e. that the polypeptide constitutes at least 96% by weight of total polypeptide material present in the preparation, and higher percentages are preferred, such as at least 97%, at least 98%, at least 99%, at least 99.25%, at least 99.5%, and at least 99.75%. It is especially preferred that the polypeptide fragment is essentially free of any other antigen with which it is natively associated, i.e. free of any other antigen from bacteria belonging to the tuberculosis complex. This can be accomplished by preparing the polypeptide fragment by means of recombinant methods in a non-mycobacterial host, or by synthesizing the polypeptide fragment by the well-known methods of solid or liquid phase peptide synthesis, e.g. by the method described by Merrifield or variations thereof.

The *M. tuberculosis* polypeptide antigens provided herein include variants that are encoded by DNA sequences that are substantially homologous to one or more of the DNA sequences specifically recited herein, for example variants having at least 80%, 85%, 90%, 91%, 92%, 93%, 94%, 95%, 96%, 97%, 98%, 99%, or 99.5% sequence identity.

In a preferred embodiment of the invention, polypeptide fragments provide for an epitope of the deletion marker. The binding site of antibodies typically utilizes multiple non-covalent interactions to achieve high affinity binding. While a few contact residues of the antigen may be brought into close proximity to the binding pocket, other parts of the antigen molecule can also be required for maintaining a conformation that permits binding. The portion of the antigen bound by the antibody is referred to as an epitope. As used herein, an epitope is that portion of the antigen that is sufficient for high affinity binding. In a polypeptide antigen, generally a linear epitope will be at least about 7 amino acids in length, and may be at least 8, at least 9, at least 10, at least 11, at least 12, at least 14, at least 16, at least 18, at least 20, at least 22, at least 24, or at least 30 amino acid residues in length. However, antibodies may also recognize conformational determinants formed by non-contiguous residues on an antigen, and an epitope can therefore require a larger fragment of the antigen to be present for binding, e.g. a domain, or up to substantially all of a protein sequence. For each antigen there exists a plurality of epitopes that, in sum, represent the immunologic determinants of that antigen, although there are instances in which an antigen contains a single epitope.

The level of affinity of antibody binding that is considered to be "specific" will be determined in part by the class of antibody, e.g. antigen specific antibodies of the IgM class may have a lower affinity than antibodies of, for example, the IgG classes. As used herein, in order to consider an antibody interaction to be "specific", the affinity will be at least about $10^{-7}$ M, usually about $10^{-8\ to\ -9}$ M, and may be up to $10^{-11}$ or higher for the epitope of interest. It will be understood by those of skill in the art that the term "specificity" refers to such a high affinity binding, and is not intended to mean that the antibody cannot bind to other molecules as well. One may find cross-reactivity with different epitopes, due, e.g. to a relatedness of antigen sequence or structure, or to the structure of the antibody binding pocket itself. Antibodies demonstrating such cross-reactivity are still considered specific for the purposes of the present invention.

Polypeptide sequences include analogs and variants produced by recombinant methods wherein such nucleic acids and polypeptide sequences are modified by substitution, insertion, addition, and/or deletion of one or more nucleotides in the nucleic acid sequence to cause the substitution, insertion, addition, and/or deletion of one or more amino acid residues in the recombinant polypeptide.

The polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, or cells of a higher organism such as vertebrates, particularly mammals, e.g. COS 7 cells, may be used as the expression host cells. Small peptides can also be synthesized in the laboratory.

With the availability of the polypeptides in large amounts, by employing an expression host, the polypeptides may be isolated and purified in accordance with conventional ways. A lysate may be prepared of the expression host and the lysate purified using HPLC, exclusion chromatography, gel electrophoresis, affinity chromatography, or other purification technique. The purified polypeptide will generally be at least about 80% pure, preferably at least about 90% pure, and may be up to and including 100% pure. Pure is intended to mean free of other proteins, as well as cellular debris.

The polypeptide is used for the production of antibodies, where short fragments provide for antibodies specific for the particular polypeptide, and larger fragments or the entire protein allow for the production of antibodies over the surface of the polypeptide. Antibodies may be raised to isolated peptides corresponding to particular domains, or to the native protein.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see *Monoclonal Antibodies: A Laboratory Manual*, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage "display" libraries, usually in conjunction with in vitro affinity maturation.

The antibody may be produced as a single chain, instead of the normal multimeric structure. Single chain antibodies are described in Jost et al. (1994) *J.B.C.* 269:26267-73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Vaccines may be formulated according to methods known in the art. Vaccines of the polypeptides as described above or modified bacteria are administered to a host which may be exposed to virulent tuberculosis. In many countries where tuberculosis is endemic, vaccination may be performed at birth, with additional vaccinations as necessary. The compounds of the present invention are administered at a dosage that provides effective immunity while minimizing any side-effects. It is contemplated that the composition will be obtained and used under the guidance of a physician.

Conventional vaccine strains of BCG may be formulated in a combination vaccine with polypeptides identified in the present invention and produced as previously described, in order to improve the efficacy of the vaccine.

In one method, a dose of the deletion marker polypeptide, formulated as a cocktail of proteins or as individual protein species, in a suitable medium is injected into the patient. The dose will usually be at least about 0.05 μg of protein, and usually not more than about 5 μg of protein.

Various methods for administration may be employed. The formulation may be injected intramuscularly, intravascularly, subcutaneously, etc. The dosage will be conventional. The bacteria can be formulated into pharmaceutical compositions by combination with appropriate, pharmaceutically acceptable carriers or diluents, and may be formulated into preparations in semi-solid or liquid forms, such as solutions, injections, etc. The following methods and excipients are merely exemplary and are in no way limiting.

The polypeptide or modified bacteria can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Unit dosage forms for injection or intravenous administration may comprise the bacteria or polypeptide of the present invention in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of vaccine, calculated in an amount sufficient to produce the desired effect in association with a pharmaceutically acceptable diluent, carrier or vehicle. The specifications for the unit dosage forms of the present invention depend on the particular bacteria employed and the effect to be achieved, and the pharmacodynamics associated with each complex in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

*Mycobacterium*, particularly those of the *M. tuberculosis* complex, are genetically engineered to contain specific deletions or insertions corresponding to the identified genetic markers. In particular, attenuated BCG strains are modified to introduce deleted genes encoding sequences important in the establishment of effective immunity. Alternatively, *M. bovis* or *M. tuberculosis* are modified by homologous recombination to create specific deletions in sequences that determine virulence, i.e. the bacteria are attenuated through recombinant techniques.

In order to stably introduce sequences into BCG, the M. tb open reading frame corresponding to one of the deletions in Table 1 is inserted into a vector that is maintained in *M. bovis* strains. Preferably, the native 5' and 3' flanking sequences are included, in order to provide for suitable regulation of transcription and translation. However, in special circumstances, exogenous promoters and other regulatory regions may be included. Vectors and methods of transfection for BCG are known in the art. For example, U.S. Pat. No. 5,776,465, herein incorporated by reference, describes the introduction of exogenous genes into BCG.

In one embodiment of the invention, the complete deleted region is replaced in BCG. The junctions of the deletion are determined as compared to a wild type M. tb. or *M. bovis* sequence, for example as set forth in the experimental section. The deleted region is cloned by any convenient method, as known in the art, e.g. PCR amplification of the region, restriction endonuclease digestion, chemical synthesis, etc. Preferably the cloned region will further comprise flanking sequences of a length sufficient to induce homologous recombination, usually at least about 25 nt, more usually at least about 100 nt, or greater. Suitable vectors and methods are known in the art, for an example, see Norman et al. (1995) *Mol. Microbiol.* 16:755-760.

In an alternative embodiment, one or more of the deletions provided in Table 1 are introduced into a strain of *M. tuberculosis* or *M. bovis*. Preferably such a strain is reduced in virulence, e.g. H37Ra, etc. Methods of homologous recombination in order to effect deletions in mycobacteria are known in the art, for example, see Norman et al., supra.; Ganjam et al. (1991) *P.N.A.S.* 88:5433-5437; and Aldovini et al. (1993) *J. Bacteriol.* 175:7282-7289. Deletions may comprise an open reading frame identified in Table 1, or may extend to the full deletion, i.e. extending into flanking regions, and may include multiple open reading frames.

The ability of the genetically altered *mycbacterium* to cause disease may be tested in one or more experimental models. For example, M. tb. is known to infect a variety of animals, and cells in culture. In one assay, mammalian macrophages, preferably human macrophages, are infected. In a comparison of virulent, avirulent and attenuated strains of the *M. tuberculosis* complex, alveolar or peripheral blood monocytes are infected at a 1:1 ratio (Silver et al. (1998) *Infect Immun* 66(3):1190-1199; Paul et al. (1996) *J Infect Dis* 174(1):105-112.) The percentages of cells infected by the strains and the initial numbers of intracellular organisms are equivalent, as were levels of monocyte viability up to 7 days following infection. However, intracellular growth reflects virulence, over a period of one or more weeks. Mycobacterial growth may be evaluated by acid-fast staining, electron microscopy, and colony-forming units (cfu) assays. Monocyte production of tumor necrosis factor alpha may also be monitored as a marker for virulence.

Other assays for virulence utilize animal models. The M. tb. complex bacteria are able to infect a wide variety of animal hosts. One model of particular interest is cavitary tuberculosis produced in rabbits by aerosolized virulent tubercle bacilli (Converse et al. (1996) *Infect Immun* 64(11): 4776-4787). In liquefied caseum, the tubercle bacilli grow extracellularly for the first time since the onset of the disease and can reach such large numbers that mutants with antimicrobial resistance may develop. From a cavity, the bacilli enter the bronchial tree and spread to other parts of the lung and also to other people. Of the commonly used laboratory animals, the rabbit is the only one in which cavitary tuberculosis can be readily produced.

Use of Deletion Markers in Identification of Mycobacteria

The deletions provided in Table 1 are useful for the identification of a *mycobacterium* as (a) variants of M. tb. (b) isolates of BCG (c) *M. bovis* strains or (d) carrying the identified mycobacterial bacteriophage, depending on the specific marker that is chosen. Such screening is particularly useful in determining whether a particular infection or isolate is pathogenic. The term mycobacteria may refer to any member of the family Mycobacteriacaeae, including *M. tuberculosis, M. avium* complex, *M. kansasii, M. scrofulaceum, M. bovis* and *M. leprae.*

Means of detecting deletions are known in the art. Deletions may be identified through the absence or presence of the sequences in mRNA or genomic DNA, through analysis of junctional regions that flank the deletion, or detection of the gene product, or, particularly relating to the tuberculin skin test, by identification of antibodies that react with the encoded gene product.

While deletions can be easily determined by the absence of hybridization, in many cases it is desirable to have a positive signal, in order to minimize artifactual negative readings. In such cases the deletions may be detected by designing a primer that flanks the junction formed by the deletion. Where the deletion is present, a novel sequence is formed between the flanking regions, which can be detected by hybridization. Preferably such a primer will be sufficiently short that it will only hybridize to the junction, and will fail to form stable hybrids with either of the separate parts of the junction.

Diagnosis is performed by protein, DNA or RNA sequence and/or hybridization analysis of any convenient sample, e.g. cultured mycobacteria, biopsy material, blood sample, etc. Screening may also be based on the functional or antigenic characteristics of the protein. Immunoassays designed to detect the encoded proteins from deleted sequences may be used in screening.

A number of methods are available for analyzing nucleic acids for the presence of a specific sequence. Where large amounts of DNA are available, genomic DNA is used directly. Alternatively, the region of interest is cloned into a suitable vector and grown in sufficient quantity for analysis. The nucleic acid may be amplified by conventional techniques, such as the polymerase chain reaction (PCR), to provide sufficient amounts for analysis. The use of the polymerase chain reaction is described in Saiki, et al. (1985) *Science* 239:487, and a review of current techniques may be found in Sambrook, et al. *Molecular Cloning: A Laboratory Manual*, CSH Press 1989, pp. 14.2-14.33. Amplification may also be used to determine whether a polymorphism is present, by using a primer that is specific for the polymorphism. Alternatively, various methods are known in the art that utilize oligonucleotide ligation, for examples see Riley et al. (1990) *N.A.R.* 18:2887-2890; and Delahunty et al. (1996) *Am. J. Hum. Genet.* 58:1239-1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2', 4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to the deleted sequence. Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO95/35505, may also be used as a means of detecting the presence of variable sequences. Single strand conformational polymorphism (SSCP) analysis, denaturing gradient gel electrophoresis (DGGE), mismatch cleavage detection, and heteroduplex analysis in gel matrices are used to detect conformational changes created by DNA sequence variation as alterations in electrophoretic mobility. Alternatively, where a polymorphism creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels.

The hybridization pattern of a control and variant sequence to an array of oligonucleotide probes immobilized on a solid support, as described in U.S. Pat. No. 5,445,934, or in WO95/35505, may be used as a means of detecting the presence or absence of deleted sequences. In one embodiment of the invention, an array of oligonucleotides is provided, where discrete positions on the array are complementary to at least a portion of M. tb. genomic DNA, usually comprising at least a portion from the identified open reading frames. Such an array may comprise a series of oligonucleotides, each of which can specifically hybridize to a nucleic acid, e.g. mRNA, cDNA, genomic DNA, etc.

Deletions may also be detected by amplification. In an embodiment of the invention, sequences are amplified that include a deletion junction, i.e. where the amplification primers hybridize to a junction sequence. In a nucleic acid sample where the marker sequence is deleted, a junction will be formed, and the primer will hybridize, thereby allowing amplification of a detectable sequence. In a nucleic acid sample where the marker sequence is present, the primer will not hybridize, and no amplification will take place. Alternatively, amplification primers may be chosen such that amplification of the target sequence will only take place where the marker sequence is present. The amplification products may be separated by size using any convenient method, as known in the art, including gel electrophoresis, chromatography, capillary electrophoresis, density gradient fractionation, etc.

In addition to the detection of deletions by the detection of junctions sequences, or detection of the marker sequences themselves, one may determine the presence or absence of the encoded protein product. The specific deletions in Table 1 correspond to open reading frames of the M. tb genome, and therefore encode polypeptides. Polypeptides are detected by means known in the art, including determining the presence of the specific polypeptide in a sample through biochemical, functional or immunological characterization. The detection of antibodies in patient serum that react with a polypeptide is of particular interest.

Immunization with BCG typically leads to a positive response against tuberculin antigens in a skin test. In people who have been immunized, which includes a significant proportion of the world population, it is therefore difficult to determine whether a positive test is the result of an immune reaction to the BCG vaccine, or to an ongoing M. tb. infection. The subject invention has provided a number of open reading frame sequences that are present in M. tb isolates, but are absent in BCG. As a primary or a secondary screening method, one may test for immunoreactivity of the patient with the polypeptides encoded by such deletion markers. Diagnosis may be performed by a number of methods. The different methods all determine the presence of an immune response to the polypeptide in a patient, where a positive response is indicative of an M. tb infection. The immune response may be determined by determination of antibody binding, or by the presence of a response to intradermal challenge with the polypeptide.

In one method, a dose of the deletion marker polypeptide, formulated as a cocktail of proteins or as individual protein species, in a suitable medium is injected subcutaneously into the patient. The dose will usually be at least about 0.05 μg of protein, and usually not more than about 5 μg of protein. A control comprising medium alone, or an unrelated protein will be injected nearby at the same time. The site of injection is examined after a period of time for the presence of a wheal. The wheal at the site of polypeptide injection is compared to that at the site of the control injection, usually by measuring the size of the wheal. The skin test readings may be assessed by a variety of objective grading systems. A positive result for the presence of an allergic condition will show an increased diameter at the site of polypeptide injection as compared to the control, usually at least about 50% increase in size, more usually at least 100% increase in size.

An alternative method for diagnosis depends on the in vitro detection of binding between antibodies in a patient sample and the subject polypeptides, either as a cocktail or as individual protein species, where the presence of specific binding is indicative of an infection. Measuring the concentration of polypeptide specific antibodies in a sample or fraction thereof may be accomplished by a variety of specific assays. In general, the assay will measure the reactivity between a patient sample, usually blood derived, generally in the form of plasma or serum. The patient sample may be used directly, or diluted as appropriate, usually about 1:10 and usually not more than about 1:10,000. Immunoassays may be performed in any physiological buffer, e.g. PBS, normal saline, HBSS, dPBS, etc.

In a preferred embodiment, a conventional sandwich type assay is used. A sandwich assay is performed by first attaching the polypeptide to an insoluble surface or support. The polypeptide may be bound to the surface by any convenient means, depending upon the nature of the surface, either directly or through specific antibodies. The particular manner of binding is not crucial so long as it is compatible with the reagents and overall methods of the invention. They may be bound to the plates covalently or non-covalently, preferably non-covalently. Samples, fractions or aliquots thereof are then added to separately assayable supports (for example, separate wells of a microtiter plate) containing support-bound polypeptide. Preferably, a series of standards, containing known concentrations of antibodies is assayed in parallel with the samples or aliquots thereof to serve as controls.

Immune specific receptors may be labeled to facilitate direct, or indirect quantification of binding. Examples of labels which permit direct measurement of second receptor binding include radiolabels, such as $^{3}H$ or $^{125}I$, fluorescers, dyes, beads, chemilumninescers, colloidal particles, and the like. Examples of labels which permit indirect measurement of binding include enzymes where the substrate may provide for a colored or fluorescent product. In a preferred embodiment, the second receptors are antibodies labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

In some cases, a competitive assay will be used. In addition to the patient sample, a competitor to the antibody is added to the reaction mix. The competitor and the antibody compete for binding to the polypeptide. Usually, the competitor molecule will be labeled and detected as previously described, where the amount of competitor binding will be proportional to the amount of Immune present. The concentration of competitor molecule will be from about 10 times the maximum anticipated Immune concentration to about equal concentration in order to make the most sensitive and linear range of detection.

Alternatively, antibodies may be used for direct determination of the presence of the deletion marker polypeptide. Antibodies specific for the subject deletion markers as previously described may be used in screening immunoassays. Samples, as used herein, include microbial cultures, biological fluids such as tracheal lavage, blood, etc. Also included in the term are derivatives and fractions of such fluids. Diagnosis may be performed by a number of methods. The different methods all determine the absence or presence of polypeptides encoded by the subject deletion markers. For example, detection may utilize staining of mycobacterial cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including microscopy, radiography, scintillation counting, etc.

An alternative method for diagnosis depends on the in vitro detection of binding between antibodies and the subject polypeptides in solution, e.g. a cell lysate. Measuring the concentration of binding in a sample or fraction thereof may be accomplished by a variety of specific assays. A conventional sandwich type assay may be used. For example, a sandwich assay may first attach specific antibodies to an insoluble surface or support. The particular manner of binding is not crucial so long as it is compatible with the reagents and overall methods of the invention. They may be bound to the plates covalently or non-covalently, preferably non-covalently. The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Samples are then added to separately assayable supports (for example, separate wells of a microtiter plate) containing antibodies. Preferably, a series of standards, containing known concentrations of the polypeptides is assayed in parallel with the samples or aliquots thereof to serve as controls. Preferably, each sample and standard will be added to multiple wells so that mean values can be obtained for each. The incubation time should be sufficient for binding, generally, from about 0.1 to 3 hr is sufficient. After incubation, the insoluble support is generally washed of non-bound components. Generally, a dilute non-ionic detergent medium at an appropriate pH, generally 7-8, is used as a wash medium. From one to six washes may be employed, with sufficient volume to thoroughly wash non-specifically bound proteins present in the sample.

After washing, a solution containing a second antibody is applied. The antibody will bind with sufficient specificity such that it can be distinguished from other components present. The second antibodies may be labeled to facilitate direct, or indirect quantification of binding. Examples of labels that permit direct measurement of second receptor binding include radiolabels, such as $^3H$ or $^{125}I$, fluorescers, dyes, beads, chemilumninescers, colloidal particles, and the like. Examples of labels which permit indirect measurement of binding include enzymes where the substrate may provide for a colored or fluorescent product. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules. Generally, from about 0.1 to 3 hr is sufficient, usually 1 hr sufficing.

After the second binding step, the insoluble support is again washed free of non-specifically bound material. The signal produced by the bound conjugate is detected by conventional means. Where an enzyme conjugate is used, an appropriate enzyme substrate is provided so a detectable product is formed.

Other immunoassays are known in the art and may find use as diagnostics. Ouchterlony plates provide a simple determination of antibody binding. Western blots may be performed on protein gels or protein spots on filters, using a detection system specific for the polypeptide, conveniently using a labeling method as described for the sandwich assay.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Experimental

Methods:

The technical methods used begin with extraction of whole genomic DNA from bacteria grown in culture.

Day 1

Inoculate culture medium of choice (LJ/7H9) and incubate at 35° C. until abundant growth. Dispense 500 µl 1×TE into each tube. (If DNA is in liquid medium, no TE needed.) Transfer loopful (sediment) of cells into microcentrifuge tube containing 500 µl of 1*TE. If taking DNA from liquid medium, let cells collect in bottom of flask. Pipette cells (about 1 ml) into tube. Heat 20 min at 80° C. to kill cells, centrifuge, resuspend in 50 µl of 1*TE. Add 50 µl of 10 mg/ml lysozyme, vortex, incubate overnight at 37° C.

Day 2

Add 70 µl of 10% SDS and 10 µl proteinase K, vortex and incubate 20 min. at 65° C. Add 100 µl of 5M NaCl. Add 100 µl of CTAB/NaCl solution, prewarmed at 65° C. Vortex until liquid content white ("milky"). Incubate 10 min at 65° C. Outside of hood, prepare new microcentrifuge tubes labeled with culture # on top, and culture #, tube #, date on side. Add 550 µl isopropanol to each and cap. Back in the hood, add 750 µl of chloroform/isoamyl alcohol, vortex for 10 sec. Centrifuge at room temp for 5 min. at 12,000 g. Transfer aqueous supernatant in 180 µl amounts to new tube using pipetter, being careful to leave behind solids and non-aqueous liquid. Place 30 min at −20 C. Spin 15 min at room temp in a microcentrifuge at 12,000 g. Discard supernatant; leave about 20 µl above pellet. Add 1 ml cold 70% ethanol and turn tube a few times upside down. Spin 5 min at room temp in a microcentrifuge. Discard supernatant; leave about 20 µl above the pellet. Spin 1 min in a microcentrifuge and discard cautiously the last 20 µl supernatant just above the pellet using a pipetter (P-20). Be sure that all traces of ethanol are removed. Allow pellet to dry at room temp for 10 min or speed vac 2-3 min. (Place open tubes in speed vac, close lid, start rotor, turn on vacuum. After 3 min. push red button, turn off vacuum, turn off rotor. Check if pellets are dry by flicking tube to see if pellet comes away from side of tube.) Redissolve the pellet in 20-50 µl of ddH2O. Small pellets get 20, regular sized get 30 and very large get 50. DNA can be stored at 4° C. for further use.

DNA array: was made by spotting DNA fragments onto glass microscope slides which were pretreated with poly-L-lysine. Spotting onto the array was accomplished by a robotic arrayer. The DNA was cross-linked to the glass by ultraviolet irradiation, and the free poly-L-lysine groups were blocked by treatment with 0.05% succinic anhydride, 50% 1-methyl-2-pyrrolidinone and 50% borate buffer.

The majority of spots on the array were PCR-derived products, produced by selecting over 9000 primer pairs designed to amplify the predicted open reading frames of the sequences strain H37Rv (ftp.sanger.ac.uk/pub/TB.seq). Some internal standards and negative control spots including plasmid vectors and non-M. tb. DNA were also on the array.

Therefore, with the preparation for an array that contained the whole genome of *Mycobacterium tuberculosis*, we compared BCG-Connaught to *Mycobacterium tuberculosis*, using the array for competitive hybridization. The protocol follows:

DNA labeling protocol. Add 4 µg DNA in 20 µl $H_2O$, 2 ml dN10N6 and 36 µl $H_2O$. 2 ml DNA spike for each DNA sample, for total of 60 µl. Boil 3 minutes to denature DNA, then snap cool on ice water bath. Add 1 µl dNTP (5 mM ACG), 10 µl 10 buffer, 4 µl Klenow, 22 µl $H_2O$ to each tube. Add 3 µl of Cy3 or Cy5 dUTP, for total of 100 µl. Incubate 3 hours at 37 C. Add 11 µl 3M NaAc, 250 µl 100% EtOH to precipitate, store O/N at −20 C. Centrifuge genomic samples 30 minutes at 13K to pellet precipitate. Discard supernatant, add 70% EtOH, spin 15 minutes, discard sup and speed-vac to dry. This provides DNA for two experiments.

DNA hybridization to microarray. protocol. Resuspend the labeled DNA in 11 µl $dH_2O$ (for 2 arrays). Run out 1 µDNA on a 1.5% agarose gel to document sample to be hybridized. Of the remaining 10 µl of solution, half will be used for this hyb, and half will be left for later date. Take 5 µl of solution Cy3 and add to same amount of Cy5 solution, for total volume 10 μl mixed labeled DNA. Add 1 μl tRNA, 2.75 μl 20×SSC, 0.4 μl SDS, for total volume 14.1 μl. Place on slide at array site, cover with 22 mm coverslip, put slide glass over and squeeze onto rubber devices, then hybridize 4 hours at 65 C. After 4 hours, remove array slides from devices, leave coverslip on, and dip in slide tray into wash buffer consisting of 1×SSC with 0.05% SDS for about 2 minutes. Cover slip should fall off into bath. After 2 minutes in wash buffer, dip once into a bath with 0.06×SSC, then rinse again in 0.06×SSC in separate bath. Dry slides in centrifuge about 600 rpm. They are now ready for scanning.

Fluorescence scanning and data acquisition. Fluorescence scanning was set for 20 microns/pixel and two readings were taken per pixel. Data for channel 1 was set to collect fluorescence from Cy3 with excitation at 520 nm and emission at 550-600 nm. Channel 2 collected signals excited at 647 nm and emitted at 660-705 nm, appropriate for Cy5. No neutral density filters were applied to the signal from either channel, and the photomultiplier tube gain was set to 5. Fine adjustments were then made to the photomultiplier gain so that signals collected from the two spots containing genomic DNA were equivalent.

To analyze the signal from each spot on the array, a 14×14 grid of boxes was applied to the data collected from the array such that signals from within each box were integrated and a value was assigned to the corresponding spot. A background value was obtained for each spot by integrating the signals measured 2 pixels outside the perimeter of the corresponding box. The signal and background values for each spot were imported into a spreadsheet program for further analysis. The background values were subtracted from the signals and a factor of 1.025 was applied to each value in channel 2 to normalize the data with respect to the signals from the genomic DNA spots.

Because the two samples are labeled with different fluorescent dyes, it is possible to determine that a spot of DNA on the array has hybridized to *Mycobacterium tuberculosis* (green dye) and not to BCG (red dye), thus demonstrating a likely deletion from the BCG genome.

However, because the array now contains spots representing 4000 spots, one may expect up to 100 spots with hybridization two standard deviations above or below the mean. Consequently, we have devised a screening protocol, where we look for mismatched hybridization in two consecutive genes on the genome. Therefore, we are essentially looking only for deletions of multiple genes at this point.

To confirm that a gene or group of genes is deleted, we perform Southern hybridization, employing a separate probe from the DNA on the array. Digestions of different *mycbacterium* DNAs are run on an agarose gel, and transferred to membranes. The membranes can be repeatedly used for probing for different DNA sequences. For the purposes of this project, we include DNA from the reference strain of *Mycobacterium tuberculosis* (H37Rv), from other laboratory strains, such as H37Ra, the O strain, from clinical isolates, from the reference strain of *Mycobacterium bovis*, and from different strains of *Mycobacterium bovis* BCG.

Once a deletion is confirmed by Southern hybridization, we then set out to characterize the exact genomic location. This is done by using polymerase chain reaction, with primers designed to be close to the edges of the deletion, see Talbot (1997) *J Clin Micro.* 35: 566-9

Primers have been chosen to amplify across the deleted region. Only in the absence of this region does one obtain an amplicon. PCR products were examined by electrophoresis (1.5% agarose) and ethidium bromide staining.

Once a short amplicon is obtained, this amplicon is then sequenced. A search of the genome database is performed to determine whether the sequence is exactly identical to one part of the *Mycobacterium tuberculosis* genome, and that the next part of the amplicon is exactly identical to another part of the *Mycobacterium tuberculosis* genome. This permits precise identification of the site of deletion.

Below follows an example of the kind of report obtained:

```
rd6 bridging PCR, blast search of sequence
emb|Z79701|MTCY277 Mycobacterium tuberculosis cosmid Y277
Length = 38,908
Plus Strand HSPs:
Score = 643 (177.7 bits), Expect = 1.6e-54, Sum P(2) = 1.6e-54
Identities = 129/131 (98%), Positives = 129/131 (98%), Strand = Plus/Plus
Query:     12  ANTAGTAATGTGCGAGCTGAGCGATGTCGCCGCTCCCAAAAATTACCAATGGTTNGGTCA  71  (SEQ ID NO:130)
               | |||||||||||||||||||||||||||||||||||||||||||||||||||| |||||
Sbjct:  24784  AGTAGTAATGTGCGAGCTGAGCGATGTCGCCGCTCCCAAAAATTACCAATGGTTTGGTCA      SEQ ID NO:131)
Query:     72  TGACGCCTTCCTAACCAGAATTGTGAATTCATACAAGCCGTAGTCGTGCAGAAGCGCAAC
               ||||||||||||||||||||||||||||||||||||||||||||||||||||||||||||
Sbjct:  24344  TGACGCCTTCCTAACCAGAATTGTGAATTCATACAAGCCGTAGTCGTGCAGAAGCGCAAC
Query:    132  ACTCTTGGAGT    142
               |||||||||||
Sbjct:  24904  ACTCTTGGAGT  24914
Score = 224 (61.9 bits), Expect = 1.6e-54, Sum P(2) = 1.6e-54
Identities = 46/49 (93%), Positives = 46/49 (93%), Strand = Plus/Plus

Query:    141  GTGGCCTACAACGGNGCTCTCCGNGGCGCGGGCGTACCGGATATCTTAG    189 (SEQ ID NO:132)
               | |||||||||||| |||||||| |||||||||||||||||||||||||
Sbjct:  37645  GCGGCCTACAACGGCGCTCTCCGCGGCGCGGGCGTACCGGATATCTTAG  37693 (SEQ ID NO:133)
```

This process is repeated with each suggested deletion, beginning with the three previously described deletions to serve as controls. Sixteen deletions have been identified by these methods, and are listed in Table 1.

It is to be understood that this invention is not limited to the particular methodology, protocols, formulations and reagents described, as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a complex" includes a plurality of such complexes and reference to "the formulation" includes reference to one or more formulations and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

What is claimed is:

1. An immunogenic composition, comprising:

a substantially pure polypeptide encoded by a nucleotide sequence comprising the open reading frame Rv2660 (SEQ ID NO:100) or a polypeptide encoded by a nucleotide fragment of at least 25 contiguous nucleotides of SEQ ID NO:100 or where said polypeptide is fused to another peptide or protein; and a pharmaceutically acceptable excipient.

2. The immunogenic composition according to claim 1, further comprising an adjuvant.

3. The immunogenic composition according to claim 1, wherein said polypeptide is fused to another peptide or protein.

4. The immunogenic composition according to claim 1, comprising a *mycobacterium* of the *M. tuberculosis* complex that has been modified by introduction of said nucleotide sequence comprising the open reading frame Rv2660 (SEQ ID NO:100) or nucleotide fragment of at least 25 contiguous nucleotides of SEQ ID NO:100.

5. The immunogenic composition according to claim 1, wherein said polypeptide is co-formulated with a *mycobacterium* of the *M. tuberculosis* complex.

6. The immunogenic composition according to claim 4, wherein said *mycobacterium* of the *M. tuberculosis* complex is bacillus Calmette-Guerin.

7. The immunogenic composition according to claim 4, wherein said *mycobacterium* of the *M. tuberculosis* complex is *M. bovis.*

8. The immunogenic composition of claim 5, wherein said *mycobacterium* of the *M. tuberculosis* complex is bacillus Calmette-Guerin.

9. The immunogenic composition according to claim 5, wherein said *mycobacterium* of the *M. tuberculosis* complex is *M. bovis.*

10. A method of immunizing an individual to *M. tuberculosis*, the method comprising:

injecting said individual with a *mycobacterium* of the *M. tuberculosis* complex that has been modified to introduce a nucleotide sequence comprising the open reading frame Rv2660(SEQ ID NO:100) or nucleotide fragment of at least 25 contiguous nucleotides of SEQ ID NO:100, wherein said *mycobacterium* of the *M. tuberculosis* complex is bacillus Calmette-Guerin.

11. A method of immunizing an individual to *M. tuberculosis*, the method comprising:

injecting said individual with a polypeptide encoded by a nucleotide sequence comprising the open reading frame Rv2660 (SEQ ID NO:100) or a polypeptide encoded by a nucleotide fragment of at least 25 contiguous nucleotides of SEQ ID NO:100 or where said polypeptide is fused to another peptide or protein, wherein said polypeptide is co-formulated with bacillus Calmette-Guerin.

12. A genetically altered *mycbacterium* of the *M. tuberculosis* complex, comprising an exogenous nucleic acid sequence comprising the open reading frame Rv2660 (SEQ ID NO:100) or at least 25 contiguous nucleotides of SEQ ID NO:100.

13. The genetically altered *mycbacterium* of claim 12, wherein said exogenous nucleic acid encodes a polypeptide that is fused to another peptide or protein.

14. The genetically altered *mycbacterium* of claim 12, wherein said *mycobacterium* is BCG.

15. The *mycbacterium* of claim 12, and a physiologically acceptable carrier for injection.

* * * * *

UNITED STATES PATENT AND TRADEMARK OFFICE

CERTIFICATE OF CORRECTION

PATENT NO. : 7,364,740 B2
APPLICATION NO. : 11/143401
DATED : April 29, 2008
INVENTOR(S) : Behr et al.

It is certified that error appears in the above-identified patent and that said Letters Patent is hereby corrected as shown below:

In The Specification Under Column 1:

• Please replace lines 6-9 with:

-- FEDERALLY SPONSORED RESEARCH OR DEVELOPMENT
This invention was made with Government support under contracts AI001137 and AI035969 awarded by the National Institutes of Health. The Government has certain rights in this invention. --

Signed and Sealed this
Nineteenth Day of April, 2011

David J. Kappos
*Director of the United States Patent and Trademark Office*

SEQUENCE LISTING

```
<160> NUMBER OF SEQ ID NOS: 137

<210> SEQ ID NO 1
<211> LENGTH: 1773
<212> TYPE: DNA
<213> ORGANISM: Mycobacteria tuberculosis

<400> SEQUENCE: 1

atgactgctg aaccggaagt acggacgctg cgcgaggttg tgctggacca gctcggcact      60

gctgaatcgc gtgcgtacaa gatgtggctg ccgccgttga ccaatccggt cccgctcaac     120

gagctcatcg cccgtgatcg gcgacaaccc ctgcgatttg ccctggggat catggatgaa     180

ccgcgccgcc atctacagga tgtgtggggc gtagacgttt ccggggccgg cggcaacatc     240

ggtattgggg gcgcacctca aaccgggaag tcgacgctac tgcagacgat ggtgatgtcg     300

gccgccgcca cacactcacc gcgcaacgtt cagttctatt gcatcgacct aggtggcggc     360

gggctgatct atctcgaaaa ccttccacac gtcggtgggg tagccaatcg gtccgagccc     420

gacaaggtca accgggtggt cgcagagatg caagccgtca tgcggcaacg ggaaaccacc     480

ttcaaggaac accgagtggg ctcgatcggg atgtaccggc agctgcgtga cgatccaagt     540

caacccgttg cgtccgatcc atacggcgac gtctttctga tcatcgacgg atggcccggt     600

tttgtcggcg agttccccga ccttgagggg caggttcaag atctggccgc ccaggggctg     660

gcgttcggcg tccacgtcat catctccacg ccacgctgga cagagctgaa gtcgcgtgtt     720

cgcgactacc tcggcaccaa gatcgagttc cggcttggtg acgtcaatga aacccagatc     780

gaccggatta cccgcgagat cccggcgaat cgtccgggtc gggcagtgtc gatggaaaag     840

caccatctga tgatcggcgt gcccaggttc gacggcgtgc acagcgccga taacctggtg     900

gaggcgatca ccgcgggggt gacgcagatc gcttcccagc acaccgaaca ggcacctccg     960

gtgcgggtcc tgccggagcg tatccacctg cacgaactcg acccgaaccc gccgggacca    1020

gagtccgact accgcactcg ctgggagatt ccgatcggct tgcgcgagac ggacctgacg    1080

ccggctcact gccacatgca cacgaacccg cacctactga tcttcggtgc ggccaaatcg    1140

ggcaagacga ccattgccca cgcgatcgcg cgcgccattt gtgcccgaaa cagtccccag    1200

caggtgcggt tcatgctcgc ggactaccgc tcgggcctgc tggacgcggt gccggacacc    1260

catctgctgg gcgccggcgc gatcaaccgc aacagcgcgt cgctagacga ggccgttcaa    1320

gcactggcgg tcaacctgaa gaagcggttg ccgccgaccg acctgacgac ggcgcagcta    1380

cgctcgcgtt cgtggtggag cggatttgac gtcgtgcttc tggtcgacga ttggcacatg    1440

atcgtgggtg ccgccggggg gatgccgccg atggcaccgc tggccccgtt attgccggcg    1500

gcggcagata tcgggttgca catcattgtc acctgtcaga tgagccaggc ttacaaggca    1560
```

-continued accatggaca agttcgtcgg cgccgcattc gggtcgggcg ctccgacaat gttcctttcg 1620
ggcgagaagc aggaattccc atccagtgag ttcaaggtca agcggcgccc ccctggccag 1680
gcatttctcg tctcgccaga cggcaaagag gtcatccagg ccccctacat cgagcctcca 1740
gaagaagtgt tcgcagcacc cccaagcgcc ggt 1773

<210> SEQ ID NO 2
<211> LENGTH: 297
<212> TYPE: DNA
<213> ORGANISM: Mycobacteria tuberculosis

<400> SEQUENCE: 2
atggaaaaaa tgtcacatga tccgatcgct gccgacattg gcacgcaagt gagcgacaac 60
gctctgcacg gcgtgacggc cggctcgacg gcgctgacgt cggtgaccgg gctggttccc 120
gcgggggccg atgaggtctc cgcccaagcg gcgacggcgt tcacatcgga gggcatccaa 180
ttgctggctt ccaatgcatc ggcccaagac cagctccacc gtgcgggcga agcggtccag 240
gacgtcgccc gcacctattc gcaaatcgac gacggcgccg ccggcgtctt cgccgaa 297

<210> SEQ ID NO 3
<211> LENGTH: 1104
<212> TYPE: DNA
<213> ORGANISM: Mycobacteria tuberculosis

<400> SEQUENCE: 3
atgctgtggc acgcaatgcc accggagcta aataccgcac ggctgatggc cggcgcgggt 60
ccggctccaa tgcttgcggc ggccgcggga tggcagacgc tttcggcggc tctggacgct 120
caggccgtcg agttgaccgc gcgcctgaac tctctgggag aagcctggac tggaggtggc 180
agcgacaagg cgcttgcggc tgcaacgccg atggtggtct ggctacaaac cgcgtcaaca 240
caggccaaga cccgtgcgat gcaggcgacg gcgcaagccg cggcatacac ccaggccatg 300
gccacgacgc cgtcgctgcc ggagatcgcc gccaaccaca tcacccaggc cgtccttacg 360
gccaccaact tcttcggtat caacacgatc ccgatcgcgt tgaccgagat ggattatttc 420
atccgtatgt ggaaccaggc agccctggca atggaggtct accaggccga gaccgcggtt 480
aacacgcttt tcgagaagct cgagccgatg gcgtcgatcc ttgatcccgg cgcgagccag 540
agcacgacga acccgatctt cggaatgccc tcccctggca gctcaacacc ggttggccag 600
ttgccgccgg cggctaccca gaccctcggc caactgggtg agatgagcgg cccgatgcag 660
cagctgaccc agccgctgca gcaggtgacg tcgttgttca gccaggtggg cggcaccggc 720
ggcggcaacc cagccgacga ggaagccgcg cagatgggcc tgctcggcac cagtccgctg 780
tcgaaccatc cgctggctgg tggatcaggc cccagcgcgg gcgcgggcct gctgcgcgcg 840
gagtcgctac ctggcgcagg tgggtcgttg acccgcacgc cgctgatgtc tcagctgatc 900
gaaaagccgg ttgccccctc ggtgatgccg gcggctgctg ccggatcgtc ggcgacgggt 960
ggcgccgctc cggtgggtgc gggagcgatg ggccagggtg cgcaatccgg cggctccacc 1020
aggccgggtc tggtcgcgcc ggcaccgctc gcgcaggagc gtgaagaaga cgacgaggac 1080
gactgggacg aagaggacga ctgg 1104

<210> SEQ ID NO 4
<211> LENGTH: 300
<212> TYPE: DNA
<213> ORGANISM: Mycobacteria tuberculosis

<400> SEQUENCE: 4

-continued atggcagaga tgaagaccga tgccgctacc ctcgcgcagg aggcaggtaa tttcgagcgg 60
atctccggcg acctgaaaac ccagatcgac caggtggagt cgacggcagg ttcgttgcag 120
ggccagtggc gcggcgcggc ggggacggcc gcccaggccg cggtggtgcg cttccaagaa 180
gcagccaata agcagaagca ggaactcgac gagatctcga cgaatattcg tcaggccggc 240
gtccaatact cgagggccga cgaggagcag cagcaggcgc tgtcctcgca aatgggcttc 300

<210> SEQ ID NO 5
<211> LENGTH: 285
<212> TYPE: DNA
<213> ORGANISM: M. tuberculosis

<400> SEQUENCE: 5
atgacagagc agcagtggaa tttcgcgggt atcgaggccg cggcaagcgc aatccaggga 60
aatgtcacgt ccattcattc cctccttgac gaggggaagc agtccctgac caagctcgca 120
gcggcctggg gcggtagcgg ttcggaggcg taccagggtg tccagcaaaa atgggacgcc 180
acggctaccg agctgaacaa cgcgctgcag aacctggcgc ggacgatcag cgaagccggt 240
caggcaatgg cttcgaccga aggcaacgtc actgggatgt tcgca 285

<210> SEQ ID NO 6
<211> LENGTH: 1998
<212> TYPE: DNA
<213> ORGANISM: Mycobacteria tuberculosis

<400> SEQUENCE: 6
atggcggccg actacgacaa gctcttccgg ccgcacgaag gtatggaagc tccggacgat 60
atggcagcgc agccgttctt cgaccccagt gcttcgtttc cgccggcgcc cgcatcggca 120
aacctaccga agcccaacgg ccagactccg cccccgacgt ccgacgacct gtcggagcgg 180
ttcgtgtcgg ccccgccgcc gccaccccca cccccacctc cgcctccgcc aactccgatg 240
ccgatcgccg caggagagcc gccctcgccg gaaccggccg catctaaacc acccacaccc 300
cccatgccca tcgccggacc cgaaccggcc ccacccaaac cacccacacc ccccatgccc 360
atcgccggac ccgaaccggc cccacccaaa ccacccacac ctccgatgcc catcgccgga 420
cctgcaccca ccccaaccga atcccagttg gcgcccccca gaccaccgac accacaaacg 480
ccaaccggag cgccgcagca accggaatca ccggcgcccc acgtaccctc gcacgggcca 540
catcaacccc ggcgcaccgc accagcaccg ccctgggcaa agatgccaat cggcgaaccc 600
ccgcccgctc cgtccagacc gtctgcgtcc ccggccgaac caccgacccg gcctgccccc 660
caacactccc gacgtgcgcg ccggggtcac cgctatcgca cagacaccga acgaaacgtc 720
gggaaggtag caactggtcc atccatccag gcgcggctgc gggcagagga agcatccggc 780
gcgcagctcg cccccggaac ggagccctcg ccagcgccgt tgggccaacc gagatcgtat 840
ctggctccgc ccacccgccc cgcgccgaca gaacctcccc ccagcccctc gccgcagcgc 900
aactccggtc ggcgtgccga gcgacgcgtc caccccgatt tagccgccca acatgccgcg 960
gcgcaacctg attcaattac ggccgcaacc actggcggtc gtcgccgcaa gcgtgcagcg 1020
ccggatctcg acgcgacaca gaaatcctta aggccggcgg ccaaggggcc gaaggtgaag 1080
aaggtgaagc cccagaaacc gaaggccacg aagccgccca aagtggtgtc gcagcgcggc 1140
tggcgacatt gggtgcatgc gttgacgcga atcaacctgg gcctgtcacc cgacgagaag 1200
tacgagctgg acctgcacgc tcgagtccgc cgcaatcccc gcgggtcgta tcagatcgcc 1260

-continued gtcgtcggtc tcaaaggtgg ggctggcaaa accacgctga cagcagcgtt ggggtcgacg 1320
ttggctcagg tgcgggccga ccggatcctg gctctagacg cggatccagg cgccggaaac 1380
ctcgccgatc gggtagggcg acaatcgggc gcgaccatcg ctgatgtgct tgcagaaaaa 1440
gagctgtcgc actacaacga catccgcgca cacactagcg tcaatgcggt caatctggaa 1500
gtgctgccgg caccggaata cagctcggcg cagcgcgcgc tcagcgacgc cgactggcat 1560
ttcatcgccg atcctgcgtc gaggttttac aacctcgtct tggctgattg tggggccggc 1620
ttcttcgacc cgctgacccg cggcgtgctg tccacggtgt ccggtgtcgt ggtcgtggca 1680
agtgtctcaa tcgacggcgc acaacaggcg tcggtcgcgt tggactggtt gcgcaacaac 1740
ggttaccaag atttggcgag ccgcgcatgc gtggtcatca atcacatcat gccgggagaa 1800
cccaatgtcg cagttaaaga cctggtgcgg catttcgaac agcaagttca acccggccgg 1860
gtcgtggtca tgccgtggga caggcacatt gcggccggaa ccgagatttc actcgacttg 1920
ctcgacccta tctacaagcg caaggtcctc gaattggccg cagcgctatc cgacgatttc 1980
gagagggctg gacgtcgt 1998

<210> SEQ ID NO 7
<211> LENGTH: 1533
<212> TYPE: DNA
<213> ORGANISM: Mycobacteria tuberculosis

<400> SEQUENCE: 7
ttgagcgcac ctgctgttgc tgctggtcct accgccgcgg gggcaaccgc tgcgcggcct 60
gccaccaccc gggtgacgat cctgaccggc agacggatga ccgatttggt actgccagcg 120
gcggtgccga tggaaactta tattgacgac accgtcgcgg tgctttccga ggtgttggaa 180
gacacgccgg ctgatgtact cggcggcttc gactttaccg cgcaaggcgt gtgggcgttc 240
gctcgtcccg gatcgccgcc gctgaagctc gaccagtcac tcgatgacgc cggggtggtc 300
gacgggtcac tgctgactct ggtgtcagtc agtcgcaccg agcgctaccg accgttggtc 360
gaggatgtca tcgacgcgat cgccgtgctt gacgagtcac ctgagttcga ccgcacggca 420
ttgaatcgct ttgtgggggc ggcgatcccg cttttgaccg cgcccgtcat cgggatggcg 480
atgcgggcgt ggtgggaaac tgggcgtagc ttgtggtggc cgttggcgat tggcatcctg 540
gggatcgctg tgctggtagg cagcttcgtc gcgaacaggt tctaccagag cggccacctg 600
gccgagtgcc tactggtcac gacgtatctg ctgatcgcaa ccgccgcagc gctggccgtg 660
ccgttgccgc gcggggtcaa ctcgttgggg gcgccacaag ttgccggcgc cgctacggcc 720
gtgctgtttt tgaccttgat gacgcggggc ggccctcgga agcgtcatga gttggcgtcg 780
tttgccgtga tcaccgctat cgcggtcatc gcggccgccg ctgccttcgg ctatggatac 840
caggactggg tccccgcggg ggggatcgca ttcgggctgt tcattgtgac gaatgcggcc 900
aagctgaccg tcgcggtcgc gcggatcgcg ctgccgccga ttccggtacc cggcgaaacc 960
gtggacaacg aggagttgct cgatcccgtc gcgaccccgg aggctaccag cgaagaaacc 1020
ccgacctggc aggccatcat cgcgtcggtg cccgcgtccg cggtccggct caccgagcgc 1080
agcaaactgg ccaagcaact tctgatcgga tacgtcacgt cgggcaccct gattctggct 1140
gccggtgcca tcgcggtcgt ggtgcgcggg cacttctttg tacacagcct ggtggtcgcg 1200
ggtttgatca cgaccgtctg cggatttcgc tcgcggcttt acgccgagcg ctggtgtgcg 1260
tgggcgttgc tggcggcgac ggtcgcgatt ccgacgggtc tgacggccaa actcatcatc 1320
tggtacccgc actatgcctg gctgttgttg agcgtctacc tcacggtagc cctggttgcg 1380

-continued

```
ctcgtggtgg tcgggtcgat ggctcacgtc cggcgcgttt caccggtcgt aaaacgaact   1440

ctggaattga tcgacggcgc catgatcgct gccatcattc ccatgctgct gtggatcacc   1500

ggggtgtacg acacggtccg caatatccgg ttc                                1533
```

<210> SEQ ID NO 8
<211> LENGTH: 840
<212> TYPE: DNA
<213> ORGANISM: Mycobacteria tuberculosis

<400> SEQUENCE: 8

```
atggctgaac cgttggccgt cgatcccacc ggcttgagcg cagcggccgc gaaattggcc     60

ggcctcgttt ttccgcagcc tccggcgccg atcgcggtca gcggaacgga ttcggtggta    120

gcagcaatca acgagaccat gccaagcatc gaatcgctgg tcagtgacgg gctgcccggc    180

gtgaaagccg ccctgactcg aacagcatcc aacatgaacg cggcggcgga cgtctatgcg    240

aagaccgatc agtcactggg aaccagtttg agccagtatg cattcggctc gtcgggcgaa    300

ggcctggctg gcgtcgcctc ggtcggtggt cagccaagtc aggctaccca gctgctgagc    360

acacccgtgt cacaggtcac gacccagctc ggcgagacgg ccgctgagct ggcacccccgt   420

gttgttgcga cggtgccgca actcgttcag ctggctccgc acgccgttca gatgtcgcaa    480

aacgcatccc ccatcgctca gacgatcagt caaaccgccc aacaggccgc ccagagcgcg    540

cagggcggca gcggcccaat gcccgcacag cttgccagcg ctgaaaaacc ggccaccgag    600

caagcggagc cggtccacga agtgacaaac gacgatcagg gcgaccaggg cgacgtgcag    660

ccggccgagg tcgttgccgc ggcacgtgac gaaggcgccg gcgcatcacc gggccagcag    720

cccggcgggg gcgttcccgc gcaagccatg gataccggag ccggtgcccg cccagcggcg    780

agtccgctgg cggccccccgt cgatccgtcg actccggcac cctcaacaac cacaacgttg   840
```

<210> SEQ ID NO 9
<211> LENGTH: 2187
<212> TYPE: DNA
<213> ORGANISM: Mycobacteria tuberculosis

<400> SEQUENCE: 9

```
atgagtatta ccaggccgac gggcagctat gccagacaga tgctggatcc gggcggctgg     60

gtggaagccg atgaagacac tttctatgac cgggcccagg aatatagcca ggttttgcaa    120

agggtcaccg atgtattgga cacctgccgc cagcagaaag gccacgtctt cgaaggcggc    180

ctatggtccg gcggcgccgc caatgctgcc aacggcgccc tgggtgcaaa catcaatcaa    240

ttgatgacgc tgcaggatta tctcgccacg gtgattacct ggcacaggca tattgccggg    300

ttgattgagc aagctaaatc cgatatcggc aataatgtgg atggcgctca acgggagatc    360

gatatcctgg agaatgaccc tagcctggat gctgatgagc gccataccgc catcaattca    420

ttggtcacgg cgacgcatgg ggccaatgtc agtctggtcg ccgagaccgc tgagcgggtg    480

ctggaatcca agaattggaa acctccgaag aacgcactcg aggatttgct tcagcagaag    540

tcgccgccac ccccagacgt gcctaccctg gtcgtgccat ccccgggcac accgggcaca    600

ccgggaaccc cgatcacccc gggaaccccg atcaccccgg gaaccccaat cacacccatc    660

ccgggagcgc cggtaactcc gatcacacca acgcccggca ctcccgtcac gccggtgacc    720

ccgggcaagc cggtcacccc ggtgaccccg gtcaaaccgg gcacaccagg cgagccaacc    780

ccgatcacgc cggtcacccc cccggtcgcc ccggccacac cggcaacccc ggccacgccc    840
```

-continued

```
gttaccccag ctcccgctcc acacccgcag ccggctccgg caccggcgcc atcgcctggg    900

ccccagccgg ttacaccggc cactcccggt ccgtctggtc cagcaacacc gggcacccca    960

gggggcgagc cggcgccgca cgtcaaaccc gcggcgttgg cggagcaacc tggtgtgccg   1020

ggccagcatg cgggcggggg gacgcagtcg gggcctgccc atgcggacga atccgccgcg   1080

tcggtgacgc cggctgcggc gtccggtgtc ccgggcgcac gggcggcggc cgccgcgccg   1140

agcggtaccg ccgtgggagc gggcgcgcgt tcgagcgtgg gtacggccgc ggcctcgggc   1200

gcggggtcgc atgctgccac tggcgggcg ccggtggcta cctcggacaa ggcggcggca   1260

ccgagcacgc gggcggcctc ggcgcggacg gcacctcctg cccgcccgcc gtcgaccgat   1320

cacatcgaca aacccgatcg cagcgagtct gcagatgacg gtacgccggt gtcgatgatc   1380

ccggtgtcgg cggctcgggc ggcacgcgac gccgccactg cagctgccag cgcccgccag   1440

cgtggccgcg gtgatgcgct gcggttggcg cgacgcatcg cggcggcgct caacgcgtcc   1500

gacaacaacg cgggcgacta cgggttcttc tggatcaccg cggtgaccac cgacggttcc   1560

atcgtcgtgg ccaacagcta tgggctggcc tacataccg acgggatgga attgccgaat   1620

aaggtgtact tggccagcgc ggatcacgca atcccggttg acgaaattgc acgctgtgcc   1680

acctacccgg ttttggccgt gcaagcctgg gcggctttcc acgacatgac gctgcgggcg   1740

gtgatcggta ccgcggagca gttggccagt tcggatcccg gtgtggccaa gattgtgctg   1800

gagccagatg acattccgga gagcggcaaa atgacgggcc ggtcgcggct ggaggtcgtc   1860

gacccctcgg cggcggctca gctggccgac actaccgatc agcgtttgct cgacttgttg   1920

ccgccggcgc cggtggatgt caatccaccg ggcgatgagc ggcacatgct gtggttcgag   1980

ctgatgaagc ccatgaccag caccgctacc ggccgcgagg ccgctcatct gcgggcgttc   2040

cgggcctacg ctgcccactc acaggagatt gccctgcacc aagcgcacac tgcgactgac   2100

gcggccgtcc agcgtgtggc cgtcgcggac tggctgtact ggcaatacgt caccgggttg   2160

ctcgaccggg ccctggccgc cgcatgc                                       2187
```

```
<210> SEQ ID NO 10
<211> LENGTH: 426
<212> TYPE: DNA
<213> ORGANISM: Mycobacteria tuberculosis

<400> SEQUENCE: 10

atggccggac tgaacattta cgtgaggcgc tggcggacag cgcttcacgc aaccgtgtcg     60

gcattgatag ttgccatcct cggactcgcc atcaccccgg tcgctagtgc ggcgacggcc    120

agggcgacgt tgtcggtgac atcgacgtgg cagaccggtt tcatcgcccg cttcaccatc    180

acaaactcga gcacggcgcc gctaaccgat tggaagcttg aattcgactt gccggcagga    240

gaatccgtct tgcacacatg gaatagcacc gttgcacgat ctggcacgca ctacgttctc    300

agcccagcga attggaatcg catcattgcc cccggtggtt cagccacggg cggcctaaga    360

ggcgggctga ccggttctta ctcgccgccg tcgagttgtc tgctcaacgg gcaatatcct    420

tgcacc                                                               426
```

```
<210> SEQ ID NO 11
<211> LENGTH: 597
<212> TYPE: DNA
<213> ORGANISM: Mycobacteria tuberculosis

<400> SEQUENCE: 11

gtgaactcac cactggtcgt cggcttcctg gcctgcttca cgctgatcgc cgcgattggc     60
```

-continued

```
gcgcagaacg cattcgtgct gcggcaggga atccagcgtg agcacgtgct gccggtggtg    120
gcgctgtgca cggtgtccga catcgtgctg atcgccgccg gtatcgcggg gttcggcgca    180
ttgatcggcg cacatccgcg tgcgctcaat gtcgtcaagt ttggcggcgc cgccttccta    240
atcggctacg ggctacttgc ggcccggcgg gcgtggcgac ctgttgcgct gatcccatct    300
ggcgccacgc cggttcgctt agccgaggtc ctggtgacct gtgcggcatt cacgttcctc    360
aacccacacg tctacctcga caccgtcgtg ttgctaggcg cgctggccaa cgagcacagc    420
gaccagcgct ggctgttcgg cctcggcgcg gtcacagcca gtgcggtatg gttcgccacc    480
ctcgggttcg gagccggccg gttgcgcggg ctgttcacca accccggctc gtggagaatc    540
ctcgacggcc tgatcgcggt catgatggtt gcgctgggaa tctcgctgac cgtgacc       597
```

<210> SEQ ID NO 12
<211> LENGTH: 909
<212> TYPE: DNA
<213> ORGANISM: Mycobacteria tuberculosis

<400> SEQUENCE: 12

```
atggtggatc cgcagcttga cggtccacag ctggccgcat tggctgccgt ggtcgaactg     60
ggcagcttcg atgcggccgc ggagcgccta catgtcaccc cgtcggctgt cagtcagcgc    120
atcaagtcgt tggagcagca ggtcggccag gtgctggtgg tcagggaaaa gccatgtcgg    180
gcgacgaccg caggtatccc gctgttgcgg ttggccgcgc aaacagcgtt gctcgagtcc    240
gaggcgctcg ctgaaatggg tggcaacgcg tcgctgaaac gcacgcggat caccattgcg    300
gtaaacgccg attccatggc gacatggttt tcggccgtgt tcgacggtct cggcgacgtc    360
ctgctcgacg ttcggatcga ggaccaggac cattccgcgc ggctgctacg ggagggtgtg    420
gcgatgggcg cggtgaccac cgagcggaac ccggtgccgg gctgccgggt gcacccgctg    480
ggtgaaatgc gctacctacc agtggccagc aggccattcg tccagcgcca tctatccgac    540
gggttcactg ccgccgcggc ggctaaagct ccgtcactgg cgtggaatcg tgacgatggg    600
ctgcaggaca tgttggtgcg taaggccttt cgtcgcgcca tcaccagacc gacgcacttt    660
gtcccgacca cagagggctt caccgccgca gcgcgcgccg ggctgggatg gggcatgttc    720
cccgagaagc tggcagcatc tccgcttgcc gatggatcgt tcgtacgggt ctgcgacata    780
cacctcgacg tccctctcta ttggcaatgc tggaaactgg acagtccgat catcgcgcga    840
attaccgaca cggtgagggc ggcggcaagc ggtctgtacc ggggccagca acgccgccgc    900
cgaccgggt                                                            909
```

<210> SEQ ID NO 13
<211> LENGTH: 651
<212> TYPE: DNA
<213> ORGANISM: Mycobacteria tuberculosis

<400> SEQUENCE: 13

```
atgactccac gcagccttgt tcgcatcgtt ggtgtcgtgg ttgcgacgac cttggcgctg     60
gtgagcgcac ccgccggcgg tcgtgccgcg catgcggatc cgtgttcgga catcgcggtc    120
gttttcgctc gcggcacgca tcaggcttct ggtcttggcg acgtcggtga ggcgttcgtc    180
gactcgctta cctcgcaagt tggcgggcgg tcgattgggg tctacgcggt gaactaccca    240
gcaagcgacg actaccgcgc gagcgcgtca aacggttccg atgatgcgag cgcccacatc    300
cagcgcaccg tcgccagctg cccgaacacc aggattgtgc ttggtggcta ttcgcagggt    360
```

-continued gcgacggtca tcgatttgtc cacctcggcg atgccgcccg cggtggcaga tcatgtcgcc 420
gctgtcgccc ttttcggcga gccatccagt ggtttctcca gcatgttgtg gggcggcggg 480
tcgttgccga caatcggtcc gctgtatagc tctaagacca taaacttgtg tgctcccgac 540
gatccaatat gcaccggagg cggcaatatt atggcgcatg tttcgtatgt tcagtcgggg 600
atgacaagcc aggcggcgac attcgcggcg aacaggctcg atcacgccgg a 651

<210> SEQ ID NO 14
<211> LENGTH: 1674
<212> TYPE: DNA
<213> ORGANISM: Mycobacteria tuberculosis

<400> SEQUENCE: 14
gtgtcatttc tggtcgtggt tcccgagttc ttgacgtccg cggcagcgga tgtggagaac 60
ataggttcca cactgcgcgc ggcgaatgcc gcggctgccg cctcgaccac cgcgcttgcg 120
gccgctggcg ctgatgaggt atcggcggcg gtggcagcgc tgtttgccag gttcggtcag 180
gaatatcaag cggtcagcgc gcaggcgagc gctttccatc aacagttcgt gcagacgctg 240
aactcggcgt caggatcgta tgcggccgcg gaggccacca tcgcgtcaca gttgcagacc 300
gcgcagcacg atctgctggg cgcggtcaat gcaccaaccg aaacgttgtt ggggcgtccg 360
ctaatcggcg acggagcacc cggacggca acgagtccga atggcggggc gggtgggctg 420
ctgtacggca acggcggcaa cggttattcc gcgacggcgt cgggggtcgg cggcggggcc 480
ggcggttccg cggggttgat cggcaatggc ggcgccgggg gagccggcgg acccaacgcc 540
cccgggggag ccggcggcaa cggtggctgg ctgctcggca acggcgggat cggcgggccc 600
gggggcgcgt cgagcatccc cggcatgagt ggtggagccg gcggaaccgg cggtgccgca 660
ggacttttgg gctggggagc gaacggcgga gccggcggcc tcggtgatgg agtcggtgtc 720
gatcgtggca cgggcggcgc cggaggccgc ggcggcctgt tgtatggcgg atacggcgtc 780
agtgggccag gcggcgacgg cagaaccgtc ccgctggaga taattcatgt cacagagccg 840
acggtacatg ccaacgtcaa cggcggaccg acgtcaacca ttctggtcga caccggatcc 900
gctggtcttg ttgtctcgcc tgaggatgtc gggggaatcc tgggagtgct tcacatgggc 960
ctcccaaccg gattgagcat cagcggttac agcgggggggc tgtactacat cttcgccacg 1020
tataccacga cggtggactt cgggaatggc atcgtcaccg cgccgaccgc cgttaatgtc 1080
gtcctcttgt ccatcccaac gtccccccttc gccatttcga cctacttcag cgccttgctg 1140
gccgatccga caacaactcc gttcgaagcc tatttcggtg ccgtcggcgt ggacggcgtt 1200
ctgggagttg ggcccaatgc ggtgggacca ggccccagca ttccgacgat ggcgttaccg 1260
ggtgacctca accagggagt gctcatcgac gcacccgcag gtgagctcgt gttcggtccc 1320
aacccgctac ctgcgcccaa cgtcgaggtc gtcggatcgc cgatcaccac cctgtacgta 1380
aagatcgatg gtgggactcc catacccgtc ccctcgatca tcgattccgg tggggtaacg 1440
ggaaccatcc cgtcatatgt catcggatcc ggaaccctgc cggcgaacac aaacattgag 1500
gtctacacca gccccggcgg tgatcggctc tacgcgttca acacaaacga ttaccgcccg 1560
accgtcattt catccggcct gatgaatacc gggttcttgc ccttcagatt ccagccggtg 1620
tacatcgact acagccccag cggtataggg acaacagtct ttgatcatcc ggcg 1674

<210> SEQ ID NO 15
<211> LENGTH: 1674
<212> TYPE: DNA
<213> ORGANISM: M. tuberculosis -continued

<400> SEQUENCE: 15
gtgtcatttc tggtcgtggt tcccgagttc ttgacgtccg cggcagcgga tgtggagaac 60
ataggttcca cactgcgcgc ggcgaatgcc gcggctgccg cctcgaccac cgcgcttgcg 120
gccgctggcg ctgatgaggt atcggcggcg gtggcagcgc tgtttgccag gttcggtcag 180
gaatatcaag cggtcagcgc gcaggcgagc gctttccatc aacagttcgt gcagacgctg 240
aactcggcgt caggatcgta tgcggccgcg gaggccacca tcgcgtcaca gttgcagacc 300
gcgcagcacg atctgctggg cgcggtcaat gcaccaaccg aaacgttgtt ggggcgtccg 360
ctaatcggcg acggagcacc cgggacggca acgagtccga atggcggggc gggtgggctg 420
ctgtacggca acggcggcaa cggttattcc gcgacggcgt cgggggtcgg cggcggggcc 480
ggcggttccg cggggttgat cggcaatggc ggcgccgggg gagccggcgg acccaacgcc 540
cccgggggag ccggcggcaa cggtggctgg ctgctcggca acggcgggat cggcgggccc 600
gggggcgcgt cgagcatccc cggcatgagt ggtggagccg gcggaaccgg cggtgccgca 660
ggacttttgg gctggggagc gaacggcgga gccggcggcc tcggtgatgg agtcggtgtc 720
gatcgtggca cgggcggcgc cggaggccgc ggcggcctgt tgtatggcgg atacggcgtc 780
agtgggccag gcggcgacgg cagaaccgtc ccgctggaga taattcatgt cacagagccg 840
acggtacatg ccaacgtcaa cggcggaccg acgtcaacca ttctggtcga caccggatcc 900
gctggtcttg ttgtctcgcc tgaggatgtc gggggaatcc tgggagtgct tcacatgggc 960
ctcccaaccg gattgagcat cagcggttac agcgggggcc tgtactacat cttcgccacg 1020
tataccacga cggtggactt cgggaatggc atcgtcaccg cgccgaccgc cgttaatgtc 1080
gtcctcttgt ccatcccaac gtccccttc gccatttcga cctacttcag cgccttgctg 1140
gccgatccga caacaactcc gttcgaagcc tatttcggtg ccgtcggcgt ggacggcgtt 1200
ctgggagttg ggcccaatgc ggtgggacca ggccccagca ttccgacgat ggcgttaccg 1260
ggtgacctca accagggagt gctcatcgac gcacccgcag gtgagctcgt gttcggtccc 1320
aacccgctac ctgcgcccaa cgtcgaggtc gtcggatcgc cgatcaccac cctgtacgta 1380
aagatcgatg gtgggactcc catacccgtc ccctcgatca tcgattccgg tggggtaacg 1440
ggaaccatcc cgtcatatgt catcggatcc ggaaccctgc cggcgaacac aaacattgag 1500
gtctacacca gccccggcgg tgatcggctc tacgcgttca acacaaacga ttaccgcccg 1560
accgtcattt catccggcct gatgaatacc gggttcttgc ccttcagatt ccagccggtg 1620
tacatcgact acagccccag cggtataggg acaacagtct ttgatcatcc ggcg 1674

<210> SEQ ID NO 16
<211> LENGTH: 417
<212> TYPE: DNA
<213> ORGANISM: Mycobacteria tuberculosis

<400> SEQUENCE: 16
atgatcgtgg acacaagcgc cgtggtggcc ctggttcaag gcgagcggcc gcacgccacc 60
ctggtcgcgg ccgccctggc cggcgcccat agccccgtca tgtctgcacc caccgtcgcc 120
gaatgcctga ttgtcttgac cgcccgtcac ggccccgttg cgcgcacgat cttcgaacga 180
cttcgcagcg aaatcggctt gagcgtgtca tctttcaccg ccgagcatgc cgctgccacg 240
caacgagcct ttctgcgata cggcaagggg cgccaccgcg cggctctcaa cttcggagac 300
tgtatgacgt acgcgaccgc ccagctgggc caccaaccac tgctggccgt cggcaacgac 360

-continued

```
ttcccgcaaa ccgaccttga gttccgcggc gtcgtcggct actggccagg cgtcgcg       417


<210> SEQ ID NO 17
<211> LENGTH: 684
<212> TYPE: DNA
<213> ORGANISM: M. tuberculosis

<400> SEQUENCE: 17

gtgcgcatca agatcttcat gctggtcacg gctgtcgttt tgctctgttg ttcgggtgtg     60

gccacggccg cgcccaagac ctactgcgag gagttgaaag gcaccgatac cggccaggcg    120

tgccagattc aaatgtccga cccggcctac aacatcaaca tcagcctgcc cagttactac    180

cccgaccaga agtcgctgga aaattacatc gcccagacgc gcgacaagtt cctcagcgcg    240

gccacatcgt ccactccacg cgaagccccc tacgaattga atatcacctc ggccacatac    300

cagtccgcga taccgccgcg tggtacgcag gccgtggtgc tcaaggtcta ccagaacgcc    360

ggcggcacgc acccaacgac cacgtacaag gccttcgatt gggaccaggc ctatcgcaag    420

ccaatcacct atgacacgct gtggcaggct gacaccgatc cgctgccagt cgtcttcccc    480

attgtgcaag gtgaactgag caagcagacc ggacaacagg tatcgatagc gccgaatgcc    540

ggcttggacc cggtgaatta tcagaacttc gcagtcacga acgacggggt gattttcttc    600

ttcaacccgg gggagttgct gcccgaagca gccggcccaa cccaggtatt ggtcccacgt    660

tccgcgatcg actcgatgct ggcc                                           684


<210> SEQ ID NO 18
<211> LENGTH: 684
<212> TYPE: DNA
<213> ORGANISM: M. tuberculosis

<400> SEQUENCE: 18

gtgcgcatca agatcttcat gctggtcacg gctgtcgttt tgctctgttg ttcgggtgtg     60

gccacggccg cgcccaagac ctactgcgag gagttgaaag gcaccgatac cggccaggcg    120

tgccagattc aaatgtccga cccggcctac aacatcaaca tcagcctgcc cagttactac    180

cccgaccaga agtcgctgga aaattacatc gcccagacgc gcgacaagtt cctcagcgcg    240

gccacatcgt ccactccacg cgaagccccc tacgaattga atatcacctc ggccacatac    300

cagtccgcga taccgccgcg tggtacgcag gccgtggtgc tcaaggtcta ccagaacgcc    360

ggcggcacgc acccaacgac cacgtacaag gccttcgatt gggaccaggc ctatcgcaag    420

ccaatcacct atgacacgct gtggcaggct gacaccgatc cgctgccagt cgtcttcccc    480

attgtgcaag gtgaactgag caagcagacc ggacaacagg tatcgatagc gccgaatgcc    540

ggcttggacc cggtgaatta tcagaacttc gcagtcacga acgacggggt gattttcttc    600

ttcaacccgg gggagttgct gcccgaagca gccggcccaa cccaggtatt ggtcccacgt    660

tccgcgatcg actcgatgct ggcc                                           684


<210> SEQ ID NO 19
<211> LENGTH: 1443
<212> TYPE: DNA
<213> ORGANISM: Mycobacteria tuberculosis

<400> SEQUENCE: 19

gtggtcggcc cgcggacgag aggatatgcg atccacaagc tgggtttctg cagcgtcgtc     60

atgctcggga tcaactcgat aatcggcgcc ggtatcttcc taactccagg tgaggtgatc    120

gggctcgcag gacccttcgc gccgatggcc tatgttttag ctggcatttt cgcgggtgtc    180
```

-continued gtggcgatcg tcttcgcgac ggcggcaagg tacgtcagaa caaacggtgc ctcctacgcc 240
tacacaacgg ccgcatttgg gcgccggatc ggcatctatg tcggtgtcac ccacgccatt 300
accgcgtcca tcgcttgggg ggtgttggct tctttttcg tctcgacgct gttgcgagtg 360
gccttccccg acaaggcctg ggccgacgcc gagcaactgt tcagtgtgaa gacgctgacg 420
tttctcggct ttatcggcgt gctgttggcc atcaacctct tcggcaaccg ggcgatcaag 480
tgggccaacg gaacgtcaac ggtaggcaag gcattcgcgc tctcggcatt cattgtcggc 540
gggctgtgga tcatcaccac ccagcacgtg aacaactacg caacggcgtg gtcggcatac 600
agcgcgaccc cgtactcgtt gcttggcgtc gccgaaattg gcaagggcac gttctcgagt 660
atggcgctgg ccacgattgt cgcgttgtac gcattcaccg gtttcgaatc gatcgcgaac 720
gccgccgaag aaatggacgc gccggaccgg aacctgccga gagctatacc gatcgcgatc 780
ttctcggttg gcgcgatcta cttgctcacc ctaacggtag cgatgctgct cggatcgaac 840
aagatcgccg cgtcggacga caccgtgaaa ctggccgcgg ccatcggaaa cgctaccttc 900
cgaacgatca tcgtcgtcgg agccctgata tcgatgttcg gcatcaatgt cgcggcctcg 960
ttcggtgcac cgcggctttg gaccgcgtta gcggacagcg ggttctgcc gacacgcttg 1020 tcacgcaaga accaatacga cgtgccgatg gtctccttcg caattacggc gtcgttggcg 1080
ctcgcattcc cgttggcgct gcggttcgac aacctgcacc tgaccggcct ggcggtgatc 1140
gcccgattcg tccagttcat catcgtgccg atcgctctca tcgcattggc gaggtctcag 1200
gcagtagaac atgctgctgt gcggcgaaat gcgttcaccg acaaggtgtt accgcttgtt 1260
gcgatcgtgg tctcggttgg gctggcagtg tcctacgact accgctgcat ctttctagtg 1320
cggggtggtc cgaactactt ctcgattgct ttgatcgtga tcacgttcgt cgtggtaccg 1380
gcgatggctt atctgcacta ctaccgaatc attcgccggg ttggcgatcg gccgagcact 1440
cgc 1443

<210> SEQ ID NO 20
<211> LENGTH: 846
<212> TYPE: DNA
<213> ORGANISM: Mycobacteria tuberculosis

<400> SEQUENCE: 20
atgggtgagg cgaacatccg cgagcaggcg atcgccacga tgccacgggg tggccccgac 60
gcgtcttggc tggatcgtcg attccagacc gacgcactgg agtacctcga ccgcgacgat 120
gtgcccgatg aggtcaaaca gaagatcatc ggggtgctcg accgggtggg caccctgacc 180
aacctgcacg agaagtacgc ccggatagcc ctgaaacttg tttctgacat tcccaacccg 240
cgaatcctgg aacttggtgc gggccatggc aagctctcag cgaaaatcct cgagctacac 300
ccgacagcga cggtgacgat cagcgatcta gatcccacct cggtggccaa catcgccgcg 360
ggagagctgg gaacacatcc gcgagcacgc acccaagtga tcgacgccac cgcaatcgac 420
ggccacgacc acagctatga cctggcggtc ttcgcgctgg catttcacca cctgccgcct 480
acggtcgcct gcaaagcgat cgccgaggcc acccgggtgg ggaagcgctt tctgatcatc 540
gacctcaaac ggcagaaacc gctgtcgttc acgctctctt cggtgctgct actgccgctc 600
cacctactgc tgctgccatg gtcgtcgatg cgctcgagca tgcacgacgg ctttatcagc 660
gcactacgtg cctacagtcc ctcggcgttg cagacgcttg cccgcgccgc cgatccggga 720
atgcaggttg aaatcttgcc cgcaccgacc aggctattcc cgccatcgct cgccgttgtg 780

-continued

```
ttctcccgtt cgagctcagc gccaacggaa tctagcgagt gctcggccga tcgccaaccc    840

ggcgaa                                                                846
```

<210> SEQ ID NO 21
<211> LENGTH: 1407
<212> TYPE: DNA
<213> ORGANISM: Mycobacteria tuberculosis

<400> SEQUENCE: 21

```
gtgagataca ctacacctgt gcgtgctgct gtctacctcc gaatctcaga agaccgctcc     60

ggcgaacagc tcggcgtggc ccgccaacgc gaggactgcc taaagctgtg cgggcagcga    120

aaatgggtgc ccgtcgagta cctcgacaac gacgtcagcg catcaaccgg caagcgccgc    180

cccgcctacg agcagatgtt ggccgacatc accgccggca agatcgccgc cgtggtggcc    240

tgggacctgg accggctcca tcgccgtccc atcgagctgg aagccttcat gtcattagcc    300

gacgagaagc ggctggccct ggccaccgtc gccggcgacg ttgacctggc gacaccccag    360

ggccggctag tcgcccgcct gaaggggtcg gtggccgctc acgaaaccga gcacaagaag    420

gcacgacagc gccgcgccgc ccgccagaaa gctgaacgcg gccaccccaa ctggtcgaaa    480

gccttcggct acctgcccgg ccccaacggt cccgaacccg acccccggac agcgccgctg    540

gtcaaacagg cctacgccga catcctcgcc ggggcgtccc tgggcgacgt gtgccgccag    600

tggaacgacg ccggggcgtt caccatcacc ggccgcccgt ggacgactac aacgctgtcg    660

aaattcttgc gcaaaccccg caacgccgga ctacgcgcat ataagggtgc ccgctacggc    720

ccggtggacc gcgacgcgat tgtcggcaag gcccagtggt cgccgctggt ggacgaggcg    780

acgttctggg ccgcccaggc cgtgctggac gcccccggcc gcgcccccgg ccgcaaaagc    840

gtgcgccgcc acctgctgac cgggctggca ggctgcggca aatgcggcaa ccacctggcc    900

ggcagctacc gcaccgacgg ccaggtcgtc tacgtgtgca aggcgtgcca cggggtggcc    960

atcctggccg acaacatcga accgatcctg tatcacatcg tggccgagcg gctggccatg   1020

cccgacgccg ttgacttgtt gcgccgggag attcacgacg ccgccgaagc cgaaaccatc   1080

cgcctggaac tggaaaccct ctacggggag ctggacaggc tcgccgtcga acgcgccgaa   1140

gggctactga ccgcgcgcca ggtgaagatc agcaccgaca tcgtcaacgc caagataacg   1200

aaacttcagg cccgccaaca ggatcaggaa cggctccgag tgttcgacgg gataccgttg   1260

ggaacaccgc aagtcgccgg gatgatagcc gagctgtcgc cggaccggtt ccgcgccgtc   1320

ctcgacgtcc tcgctgaagt cgttgtccag ccggtcggca agagcggcag gatattcaat   1380

cccgaacggg tgcaggtgaa ttggcga                                       1407
```

<210> SEQ ID NO 22
<211> LENGTH: 513
<212> TYPE: DNA
<213> ORGANISM: M. tuberculosis

<400> SEQUENCE: 22

```
atgagccggc accacaacat cgtgatcgtc tgtgaccacg gccgcaaagg cgatggccgc     60

atcgaacacg agcgctgcga tcttgtcgcg ccgatcattt gggtcgacga gacccagggc    120

tggttaccgc aggcgccagc ggtggcaaca ttactcgacg acgacaacca gccgcgagcc    180

gttattggct tgccgcccaa cgagtctcgc ctacgacctg aaatgcgccg cgacgggtgg    240

gtgcggctgc actgggaatt cgcctgcctg aggtacggcg ccgccggcgt gcgcacgtgc    300

gagcagcggc ccgtgcgggt tcgcaacggc gacctgcaaa cactgtgcga gaacgttccg    360
```

-continued

```
cggctactga ccggactggc cggcaacccc gactacgcac cgggttttgc ggtgcagtcg    420

gacgcggtgg tcgtcgccat gtggctgtgg cgcacgctct gcgaaagcga cacgccgaac    480

aaactacgcg ccaccccaac gcgtggtagc tgc                                 513
```

<210> SEQ ID NO 23
<211> LENGTH: 219
<212> TYPE: DNA
<213> ORGANISM: M. tuberculosis

<400> SEQUENCE: 23

```
gtgtcgacca tctaccatca tcgcggccgc gtagccgcac tgtctcgttc ccgcgcatcc     60

gacgatcccg agttcatcgc cgcgaaaacc gatctcgttg ccgcgaacat cgcggactac    120

ctcatccgca ccctcgccgc agcgccgccc ctgactgacg agcagcgcac ccggctggcc    180

gagctgctgc gccccgtgcg gcggtcaggc ggtgcccga                           219
```

<210> SEQ ID NO 24
<211> LENGTH: 396
<212> TYPE: DNA
<213> ORGANISM: Mycobacteria tuberculosis

<400> SEQUENCE: 24

```
atgaccgccg gcgccggcgg gtcgccgccg acgcgacgat gcccggccac ggaggaccgg     60

gcacccgcga cagtcgccac accgtctagc gccgatccta ccgcgtcacg cgccgtgtcg    120

tggtggtcgg tgcacgagca tgtcgcgccg gtcctggatg ctgccgggtc gtggccgatg    180

gccggcacac cggcctggcg tcagctcgac gacgccgatc ctcgcaaatg ggccgcgatc    240

tgcgacgcag cccggcactg ggctctgagg gtagagacgt gccaggaggc gatggcgcag    300

gcgtcacgtg acgtatctgc ggccgccgac tggcccggca tcgcccgcga gatcgtccga    360

cggcgcggcg tgtacatccc gcgggcgggg gtggcg                              396
```

<210> SEQ ID NO 25
<211> LENGTH: 1413
<212> TYPE: DNA
<213> ORGANISM: Mycobacteria tuberculosis

<400> SEQUENCE: 25

```
atggccgaca tcccctacgg caccgactat cccgacgccc cctggatcga ccgggacggg     60

cacgtgctca tcgacgacgg tggcaaaccg acgcaagttc atcgcggcca agcccgaatc    120

gcctaccggc tagccgaacg ttaccaggac aagctgctgc acgtggccgg gatcggctgg    180

cactcctggg acggcagacg ctgggcagcc gacgaccgcg gcgaagccaa acgtgcagtg    240

ctggcagagc tgcgccaagc gctctcagac agcctcaacg acaaggaatt acgcgccgac    300

gtccgaaaat gcgaatcggc gtccggcgtg gccggcgtgc tcgacctggc cgccgcactg    360

gtaccattcg ccgcgacggt agccgacctc gacagcgacc cgcacttgct caacgtcgcg    420

aatgggacgc tggacctgca cacgctcaaa ttgcggcccc acgcgcccgc tgaccgcatc    480

acaaagatat gccgcggtgc ctaccagtcc gacaccgaat cgcctctctg gcaagcgttc    540

ttgacccgcg ttctgcccga tgaaggtgtg cgcgggttcg tgcaacgcct ggccggcgtc    600

ggcctactag gcaccgtccg cgaacatgtc ctggcgattc ttatcggtgt aggtgccaac    660

ggaaaatctg tgttcgacaa ggcgattcgc tatgcccttg gcgattatgc ctgcaccgct    720

gagcctgacc ttttcatgca ccgggaaaac gctcacccaa caggcgaaat ggacctccgc    780
```

-continued

```
ggcgtgcgat gggtagcggt atccgagagc gaaaaagatc gccggctggc cgaatcaacg    840

ataaaacggc tgactggcgg cgacaccatc cgcgcccgaa agatgcggca agacttcgtg    900

gaattcacgc cgtcacatac ccactgctc atcaccaacc acctaccgag agtgcccggc     960

gatgatacgg ccatctggcg gcgaattcga gtggtgccgt ttgaagtagt gattcctgcc   1020

gacgagcagg accgggaact ggacgcacgg ttgcagttgg aggccgacag catcctgtcc   1080

tgggcggtgg ccggatggag cgactatcag cgaatcggac tatcccagcc ggacgcggtg   1140

ctcgcggcaa cgtcgaatta ccgcgaggac tccgacacga taaagaggtt catcgacgac   1200

gaatgcgtca ccagctcgcc ggtgctgaaa gccactacta cgcatctgtt cgaggcgtgg   1260

caaaggtggc gggtgcaaga aggcgtaccc gaaatctcgc gcaaagcgtt cggccagtcg   1320

ctcgacaccc acggataccc ggtcactgac aaggcccgtg atggtcgttg gcgggccgga   1380

atagcggtga gaggggccga tgatttcgat gat                                1413
```

<210> SEQ ID NO 26
<211> LENGTH: 393
<212> TYPE: DNA
<213> ORGANISM: Mycobacteria tuberculosis

<400> SEQUENCE: 26

```
atgaccgctg tcgcgatcac cccggcatcc ggcggtcggc acagcgtccg attcgcctac     60

gactctgcga tcgtgtcgtt gatcaagtcc acgatccccg cctatgcccg ctcctggtcc    120

gcgcacaccc gctgctggtt catcgacgct gactggaccc cactgctggc cgccgagctg    180

cgctaccacg gccacaccgt caccggaccc gccgaccccgg cgcaacagca gtgcaccgac   240

tgggccaaag cgttgttccg ggcggtcgga ccccagcgga cacccgccgt gtacagggct    300

ttatccaaag tgctgcaccc cgacgcccca accggatgcc cgatactgca acagcagctc    360

aatgccgcca gaaccgcact taccaaccct gct                                 393
```

<210> SEQ ID NO 27
<211> LENGTH: 270
<212> TYPE: DNA
<213> ORGANISM: Mycobacteria tuberculosis

<400> SEQUENCE: 27

```
atggctgaaa cccccgacca cgccgaactg cggcgacgaa tcgccgacat ggctttcaac     60

gccgatgtcg gtatggcgac ctgcaaacgc tgtggtgacg ccgtgccgta catcatcctg    120

ccgaacctgc agaccggcga acccgtcatg ggtgtcgccg acaacaaatg gaagcgcgcg    180

aactgtcccg tcgacgtcgg taagccgtgc ccgttcctaa tcgccgaggg tgtcgccgac    240

agcaccgacg acaccataga ggtcgaccag                                     270
```

<210> SEQ ID NO 28
<211> LENGTH: 312
<212> TYPE: DNA
<213> ORGANISM: Mycobacteria tuberculosis

<400> SEQUENCE: 28

```
gtgaccccga tcaaccggcc cctgaccaac gacgaacgac aactgatgca cgagctggca     60

gtccaggttg tctgctcgca gacgggttgc tcacccgatg cggcggtcga agcactcgaa    120

tccttcgcga aagacggaac acttatcctc cgcggcgaca ccgagaacgc ctacctcgaa    180

gccggaggca atgttcttgt ccatgccgat cgtgactggc ttgccttcca cgcgtcgtat    240

cccggcaacg acccgctgcg agacgcccga cctatcgagc aggacgacga ccagggggcg    300
```

-continued

```
gggtcgccat cg                                                     312

<210> SEQ ID NO 29
<211> LENGTH: 468
<212> TYPE: DNA
<213> ORGANISM: Mycobacteria tuberculosis

<400> SEQUENCE: 29

atgccaagac caccgaaacc ggcccggctc aaactggttg agggccgctc cccggccgc     60

gattccggcg gccggaaagt ccccgagtcg ccgaagttta tccgtcaggc accggatgcc    120

ccggactggc tcgacgccga ggcgctggcc gaatggcggc gcgtcgcacc gactttggag    180

cggcttgacc tgctcaaacc tgaggatcgg gcgctcctgt ccgcgtactg cgagacctgg    240

tccgtctacg tcgcggcggt tcagcgggtc cgcgccgaag gcctcacaat tacctcaccg    300

aaatccggtg tcgtgcaccg gaacccggcg gtgacggttg cggagacggc gcgcatgcat    360

ctgctgcgct tggcctccga gtttggcctg accccggccg ccgagcagcg actggcggtg    420

gcgccgggcg acgacggcga cgggctcaac ccgtttgccc cggaccgg                 468

<210> SEQ ID NO 30
<211> LENGTH: 510
<212> TYPE: DNA
<213> ORGANISM: Mycobacteria tuberculosis

<400> SEQUENCE: 30

atggccgagc tgcggtctgg cgaaggccga accgtgcacg gcaccatcgt gccctacaac     60

gaggcgacca ccgtccgcga cttcgacggc gagttccagg aaatgttcgc tcctggcgct    120

tttcggcgct ccatcgccga gcgcggccac aaattgaagc tgctggtctc tcacgacgct    180

cgaacccgct acccggtggg ccgggccgtt gagttgcggg aggagcctca cggcttgttc    240

ggggcgttcg agattgcgga caccccggac ggcgacgagg ctttggcgaa cgtaaaagct    300

ggtgtcgtcg actcgttttc ggtgggtttc cgaccgatcc gggaccgtcg cgaaggggat    360

gtgctggtgc gcgtcgaagc ggcgctgtta gaggtttccc taaccggcgt tccggcctat    420

tcgggggcac aaatcgccgg ggtgcgcgcg gaatcgctta cagtcgtttc ccgttcgaca    480

gccgaagcct ggctgtccct actcgattgg                                     510

<210> SEQ ID NO 31
<211> LENGTH: 1419
<212> TYPE: DNA
<213> ORGANISM: Mycobacteria tuberculosis

<400> SEQUENCE: 31

atgaccgaat tcgacgacat caaaaacctc tctttacctg aaacccgtga cgcggcgaag     60

cagctcctcg acagtgtcgc cggcgacctg accggtgagg cggcgcagcg ttttcaggcg    120

ctgacgcgcc acgccgagga actgcgggcg gagcagcgcc gccgcggccg cgaagccgag    180

gaggcgctgc gccgctaccg ggccggtgag ctgagggtgg tgcccggcgc tcccaccggc    240

ggcgacgacg gcgacgcgcc gccgggcaac tcgttgcggg acaccgcgtt tcgcacactg    300

gattcttgtg tgcgagacgg cctgatgtcg tcgcgggcgg cggagaccgc ggaaaccttg    360

tgccgcaccg ggccgccgca gtccacctcg tgggcgcagc gctggctggc ggccaccggc    420

agccgcgact atttgggcgc gttcgtcaag cgggtttcca atcctgttgc ggggcacacg    480

gtttggaccg accgggaagc ggccgcgtgg cgtgaggctg ccgcggtggc cgccgagcag    540
```

-continued

```
cgagcgatgg gcctggtgga cacccaaggc gggtttctga tcccggcggc gctggacccg    600

gcgatcctgc tgtcgggtga tgggtcgacg aacccgattc ggcaggtggc gagggtggtg    660

caaacgacct ccgagatttg gcggggcgtg acttccgaag gcgccgaagc tcgttggtac    720

tccgaagccc aggaggtgtc cgacgattcg ccagcgttgg cccagccggc ggtgccgaac    780

taccgtggaa gctgctggat tccgttctcc atcgagctgg agggtgacgc ggcgagcttc    840

gttggcgaga tcggcaagat tctcgcggac agcgttgagc aactgcaggc cgcggcgttc    900

gtcaacggct ccggcaacgg cgagcccacc gggttcgtca gcgcgctaac cggcacctcc    960

gatcaggtgg tcgtcggcgc ggggtcagaa gcgattgtgg cggcggatgt ttacgcgttg   1020

cagtcggcgc tgccgccaag gttccaggcc agcgccgcgt tcgcggcgaa cttgtccacc   1080

atcaacacgt tgcggcaggc ggaaacttcg aatggcgcgc tgaaattccc atcgctgcac   1140

gacagtccgc cgatgctagc cgggaagtct gtcctggaag tctcccacat ggacaccgtt   1200

gattcggcgg tgacagcgac gaatcatcca ctggtgcttg gcgactggaa gcaattcctc   1260

atcggcgaca gagttgggtc catggtggag ttggtgcctc acctgttcgg gccgaatcgc   1320

cggccgaccg ggcagcgcgg attcttcgcc tggttcaggg tcggatcaga tgtgctggtg   1380

cgcaacgcgt ttcgagttct gaaggtggag actaccgcg                          1419
```

```
<210> SEQ ID NO 32
<211> LENGTH: 351
<212> TYPE: DNA
<213> ORGANISM: Mycobacteria tuberculosis

<400> SEQUENCE: 32

atggcgccgc tggccgccgg atcgccgagc tggaacggcc gaaagccaag cagcggcaac     60

aggaaggcgg cgaccatggc cgccaggctc gatattctgg cttggggccc atgggcccca    120

agccagaatc ggagcgtcgt tcgacgaaaa cagacactgc tatcggcgca gccctcggca    180

tctccgccgg cacctaccgg cggctcaaac gaatcgacaa cgcaacccgc agcgagttgg    240

cgcgtgggcg gcccggcacc cctaagcaga ggccgcccac gcctggccct atcctaccta    300

cgcggtagtc tccaccttca gaactcgaaa cgcgttgcgc accagcacat c             351
```

```
<210> SEQ ID NO 33
<211> LENGTH: 309
<212> TYPE: DNA
<213> ORGANISM: Mycobacteria tuburculosis

<400> SEQUENCE: 33

atgggctaca aaccagaatc agagcgtcat tcgacgaaaa cagacactgc tatcggcgca     60

gccctcggca tctccgccgg cacctaccgg cggctcaaac gaatcgacaa cgcaacccac    120

agcgacgaca aagaaatccg ccggttcgcg gagaaacaaa tggcgccgct ggtcgccgga    180

tcgccgagct ggaacgcccg aaagccaagg agcgccaacg cgagggtggt cgcctcggtg    240

catcgatcac caatgccggc tttggtccca tggaaccaaa gccgtctcag cgccacactg    300

acaaggagg                                                            309
```

```
<210> SEQ ID NO 34
<211> LENGTH: 408
<212> TYPE: DNA
<213> ORGANISM: Mycobacteria tuburculosis

<400> SEQUENCE: 34

atgaccacca caccagcacg tttcaaccac ttggtgacgg taaccgacct ggaaacgggt     60
```

-continued

```
gaccgcgccg tctgcgaccg cgaccaggtg gccgagacga tccgggcgtg gttcccggac    120

gcgcccttgg aggtgaggga agcgctcgtt cggctgcagg ccgcgttgaa tcggcacgag    180

cacaccggcg agctcgaagc gttcctgcgg atcagcgtcg agcacgccga cgccgccggc    240

ggcgacgagt gcggcccggc gatcctggcc ggccgctccg ggccggaaca agccgccatc    300

aaccggcaac tcggactcgc cggcgacgac gagcccgacg gcgacgacac cccgccgtgg    360

agccggatga tcgggcttgg cggcggaagc ccagcggaag acgagcgc                 408
```

<210> SEQ ID NO 35
<211> LENGTH: 1407
<212> TYPE: DNA
<213> ORGANISM: Mycobacteria tuburculosis

<400> SEQUENCE: 35

```
gtgaaacggc tcagcggctg ggacgcggta ctgctttaca gcgagacccc gaatgtgcac     60

atgcacacac tcaaggtcgc cgtgatcgaa ttggattcgg acagacagga attcggtgtc    120

gacgcgtttc gcgaggtgat cgctggccgg ctgcataagc ttgagccatt gggctatcag    180

ctggttgatg tcccgttgaa gttccatcac ccgatgtggc gggagcactg ccaggtcgat    240

ctcaactacc acatccggcc gtggcggttg cgcgccccgg ggggtcggcg cgaactcgac    300

gaggcggtcg gagaaatcgc cagcaccccg ctgaaccgcg accacccgct gtgggagatg    360

tacttcgttg aggggcttgc caaccaccgg atcgcggtgg ttgccaaaat tcaccatgcg    420

ttggctgacg gtgttgcctc ggcaaacatg atggcacggg ggatggatct gctgccggga    480

ccggaggtcg gccgctatgt gcctgacccc gctcctacca agcggcagtt gctgtccgcg    540

gcgttcatcg accacttgcg ccacctcggc cggattcctg caaccatccg gtacaccacg    600

cagggtctag gccgggtgcg acgtagctcg cgcaagctct cacccgcact gaccatgcca    660

tttaccccgc caccgacgtt catgaatcac cggctcaccc cggagcgcag gttcgccacc    720

gccaccctgg cgctgattga cgtgaaggcg acggccaagt tgctgggggc gacgatcaac    780

gacatggtgc tggccatgtc gaccggcgct ctgcgtaccc tgctattgcg ctatgacggc    840

aaggccgaac cgctgctggc gtcggtcccg gtgagttacg acttctcacc ggagcggatc    900

tccggtaacc gcttcaccgg aatgctggtg gcgctgcctg ccgactccga cgacccgttg    960

cagcgggtgc gcgtctgtca cgaaaacgcg gtctccgcca aggagagcca ccagcttttg   1020

ggaccggagt tgatcagccg ctgggcggct tactggccac ctgccggtgc ggaagccttg   1080

ttccggtggt tgtctgagcg cgacgggcag aacaaggtac tcaacttgaa tatctcgaat   1140

gttcccggtc cgcgcgaacg cggccgcgtg gggccgcgc tggtcaccga gatctattcg   1200

gtgggcccgt tgaccgccgg tagcggattg aatatcacgg tgtggagtta tgtcgatcag   1260

ctcaatatct cggtgttaac cgatggttcc accgtgcagg acccgcatga agtaaccgcg   1320

ggaatgatcg cggacttcat cgaaatacgc cgcgccgctg gtctttccgt ggagttgaca   1380

gtcgtcgagt ccgcgatggc gcaggca                                       1407
```

<210> SEQ ID NO 36
<211> LENGTH: 786
<212> TYPE: DNA
<213> ORGANISM: Mycobacteria tuburculosis

<400> SEQUENCE: 36

```
atgagcagcg aaagcgacgc agccaacacc gaacctgagg ttctggtaga acagcgggat     60
```

-continued

```
cggattttga tcatcacgat caaccgcccg aaagccaaga acgcggtcaa cgccgcagtc    120

agccggggct tggccgatgc gatggatcag cttgacggcg atgccggcct gtcggtggca    180

atcctgaccg gtgggggcgg ttcgttctgc gcgggcatgg acctcaaggc gttcgcccgg    240

ggcgagaatg tcgtcgtcga aggtcgcggc cttggcttta ccgaacgtcc gccgaccaag    300

ccgctcattg ctgcggtgga aggctacgcg ttggcgggtg gcaccgagct ggcgcttgct    360

gccgacctga tcgtggcggc cagggattcg gcgttcggga ttcctgaagt caagcggggt    420

ctggttgccg gcggcggggg attgctgcgg ttgccggagc gcatcccgta tgcgatagcc    480

atggagttgg cgctgaccgg tgacaaccta ccggccgaac gcgcgcacga gctggggctc    540

gtcaacgttt tggccgagcc ggggaccgcc ctcgatgctg cgatcgcgtt ggcggagaag    600

atcaccgcca atgggccgct ggcggtggtg gccaccaagc ggattatcac cgagtcgcgt    660

gggtggagtc ccgacactat gttcgctgag cagatgaaga tcctggtgcc ggtgttcacc    720

tccaacgacg cgaaggaagg tgcgatcgcg ttcgccgaga ggcgccggcc ccgttggacg    780

ggcacc                                                               786
```

<210> SEQ ID NO 37
<211> LENGTH: 1461
<212> TYPE: DNA
<213> ORGANISM: M. tuberculosis

<400> SEQUENCE: 37

```
atgtctgaca gtgccacgga atacgacaag cttttcatcg gcggcaagtg gaccaaaccg     60

tcgacctccg atgttatcga ggtacgctgc ccagccactg ggaatatgt cggcaaggtg    120

ccgatggcgg ccgccgccga cgtcgacgcc gcggtcgccg cagcacgtgc ggcgttcgac    180

aacggcccct ggccctcgac cccgccgcac gagcgtgcgg cggtgatcgc tgcggcggtc    240

aagatgctgg ctgagcgcaa ggacctgttc accaagctgc tcgcagccga aaccggccag    300

ccgccgacca tcatcgagac gatgcactgg atgggttcga tgggggcgat gaactacttt    360

gccggtgcag cggacaaggt cacctggacc gaaacccgca ccggctccta tggacagagc    420

attgtcagcc gtgagccggt cggtgtggtg ggcgcgatcg tggcctggaa cgtcccgctg    480

tttctggccg tcaacaagat tgcgccggcg ctgctggccg gctgcaccat cgtgctcaag    540

cccgccgccg aaacaccgct gaccgcaaac gctttggcgg aggtgttcgc cgaggtgggc    600

ctgcccgagg gggtgttgtc ggtagtgccg ggagggattg agaccggtca ggcgctgacg    660

tctaacccgg acatcgacat gtttaccttc accggcagct cggccgtcgg ccgagaggtc    720

ggcaggcgtg ccgctgagat gctcaagccg tgcaccttag aactcggcgg caagtcggcg    780

gccatcattc tcgaggacgt cgacctggcc gcagctattc cgatgatggt gttctccggc    840

gtcatgaacg ccggacaggg ctgcgtcaac cagacccgca ttctggctcc gcgctcccgg    900

tacgacgaaa tcgtggctgc ggtaactaat ttcgtaacgg ctctcccggt gggcccgccg    960

tcggacccgg cagctcagat cgggccgctg atctcggaga agcagcggac tcgcgttgaa   1020

ggctacatcg ccaagggcat cgaggagggc gctcggttgg tgtgcggcgg cggccgtccc   1080

gagggcttgg acaacggctt ctttatccaa cccaccgtat tcgccgatgt cgacaacaag   1140

atgaccatcg cacaggagga gatcttcggg ccggtgctgg ccatcattcc ttatgacacc   1200

gaggaggacg cgatcgcgat cgccaacgat tcagtgtatg ggctggcggg cagcgtgtgg   1260

accaccgacg tgcccaaagg catcaagatc tcgcagcaga tccgcaccgg gacatacgga   1320

atcaactggt acgccttcga tcccggctca cccttcggcg gctacaagaa ctccggaatc   1380
```

-continued ggccgcgaga acgggcccga gggtgtcgaa cacttcaccc agcaaaagag tgtcctgctg 1440
ccgatgggct acaccgtcgc g 1461

<210> SEQ ID NO 38
<211> LENGTH: 831
<212> TYPE: DNA
<213> ORGANISM: M. tuberculosis

<400> SEQUENCE: 38
atggcacgct gcgatgtcct ggtctccgcc gactgggctg agagcaatct gcacgcgccg 60
aaggtcgttt tcgtcgaagt ggacgaggac accagtgcat atgaccgtga ccatattgcc 120
ggcgcgatca agttggactg gcgcaccgac ctgcaggatc cggtcaaacg tgacttcgtc 180
gacgcccagc aattctccaa gctgctgtcc gagcgtggca tcgccaacga ggacacggtg 240
atcctgtacg gcggcaacaa caattggttc gccgcctacg cgtactggta tttcaagctc 300
tacggccatg agaaggtcaa gttgctcgac ggcggccgca agaagtggga gctcgacgga 360
cgcccgctgt ccagcgaccc ggtcagccgg ccggtgacct cctacaccgc ctccccgccg 420
gataacacga ttcgggcatt ccgcgacgag gtcctggcgg ccatcaacgt caagaacctc 480
atcgacgtgc gctctcccga cgagttctcc ggcaagatcc tggcccccgc gcacctgccg 540
caggaacaaa gccagcggcc cggacacatt cctggtgcca tcaacgtgcc gtggagcagg 600
gccgccaacg aggacggcac cttcaagtcc gatgaggagt tggccaagct ttacgccgac 660
gccggcctag acaacagcaa ggaaacgatt gcctactgcc gaatcgggga acggtcctcg 720
cacacctggt tcgtgttgcg ggaattactc ggacaccaaa acgtcaagaa ctacgacggc 780
agttggacag aatacggctc cctggtgggc gccccgatcg agttgggaag c 831

<210> SEQ ID NO 39
<211> LENGTH: 300
<212> TYPE: DNA
<213> ORGANISM: M. tuberculosis

<400> SEQUENCE: 39
atgtgctctg gacccaagca aggactgaca ttgccggcca gcgtcgacct ggaaaaagaa 60
acggtgatca ccggccgcgt agtggacggt gacggccagg ccgtgggcgg cgcgttcgtg 120
cggctgctgg actcctccga cgagttcacc gcggaggtcg tcgcgtcggc caccggcgat 180
ttccggttct tcgccgcgcc cggatcctgg acgctgcgcg cgctgtcggc ggccggcaac 240
ggcgacgcgg tggtgcagcc ctcgggcgcg ggcatccacg aggtagacgt caagatcacc 300

<210> SEQ ID NO 40
<211> LENGTH: 441
<212> TYPE: DNA
<213> ORGANISM: M. tuberculosis

<400> SEQUENCE: 40
atggccaatg tggtagctga aggtgcctac ccttactgtc ggctcactga tcagccgctg 60
agtgtggacg aagtgctagc cgccgtctcg ggccccgaac aaggcggcat tgtcatattt 120
gtgggaaacg tgcgtgacca caatgccggg catgatgtca cgcggttgtt ctacgaggcg 180
tatccgccga tggtgattcg gacattgatg tcgatcatcg gacggtgtga agacaaggcc 240
gagggtgtcc gcgttgctgt cgcgcaccgg accggtgaat tgcaaatcgg tgatgccgcg 300
gtcgttattg gcgcgtcagc tccccaccgt gcggaggcat ttgacgccgc gcgtatgtgt 360

-continued atcgagttgc ttaagcagga agtgccgatt tggaagaagg aattcagctc gaccggtgct 420
gaatgggtcg gcgatagacc a 441

<210> SEQ ID NO 41
<211> LENGTH: 600
<212> TYPE: DNA
<213> ORGANISM: M. tuberculosis

<400> SEQUENCE: 41
atgagtccgt ctccatcggc cctgctcgcc gaccacccgg accgcattcg ttggaacgcg 60
aaatacgagt gcgctgaccc cacggaggcg gtatttgcgc ccatatcctg gctcggcgac 120
gtgctgcagt tcggggtgcc agaagggccg gttctggaac tggcgtgcgg tcggtccggc 180
accgcgctgg ggctagccgc ggcgggccgc tgcgtgactg cgatcgacgt ttccgatacc 240
gcgttggttc agctcgagct cgaagcgacc cgacgggaat tggccgatcg cctcacactg 300
gtgcacgccg atctctgctc ctggcagtcg gggatggac gctttgctct ggtactttgc 360
cgactattct ggcatccgcc cacttttcgc caggcttgcg aggctgtggc gccgggcggt 420
gtagtggcgt gggaggcatg gcggcggccc atcgatgtcg ctcgggatac ccgtcgagcc 480
gaatggtgct tgaagccagg ccagcccgag tctgaacttc ccgccggctt cacggtgatt 540
cgggtggtcg acaccgatgg ttcagagccg tcgcggcgca tcatcgccca acggtcactg 600

<210> SEQ ID NO 42
<211> LENGTH: 1200
<212> TYPE: DNA
<213> ORGANISM: Mycobacteria tuburculosis

<400> SEQUENCE: 42
atgacaagca cctcgattcc gacgttcccg ttcgaccggc cggtcccgac ggagccgtcc 60
ccaatgctgt cggaactgag aaacagctgt ccggtagccc cgatagagtt gccctcgggg 120
cacacagcat ggctcgtcac tcgctttgac gatgtaaagg gagtgctgtc cgacaagcgt 180
ttcagctgca gggcggcagc gcacccgtcg tcgcccccgt tcgtgccgtt cgtgcagctt 240
tgccccagct tgttgagcat cgatgggccc caacacaccg cggcccgccg tctgctcgcg 300
cagggcctaa atcccggctt catcgcacgc atgcggcccg ttgtccaaca gatcgtcgac 360
aatgcgctcg acgatctggc agccgcggaa ccaccggtgg acttccagga aatagtaagt 420
gtccctatcg gagaacagct catggccaag ctactcgggg tcgagcccaa aaccgtgcac 480
gagctcgcgg cgcacgtgga tgcggcgatg tccgtgtgtg agatcggcga cgaggaggtg 540
agccggcggt ggtcagcact gtgcacgatg gtcatcgaca tactgcaccg caagctcgcc 600
gaaccgggtg atgacctact tagcacgatc gcccaggcga accggcaaca gtccaccatg 660
accgacgagc aggttgtcgg catgctcctc accgtcgtga tcggaggagt cgacacaccg 720
atcgccgtga tcacaaacgg gctggcgagc ctgctgcacc accgcgatca atatgaacgg 780
ctcgttgaag acccaggccg tgtcgctcgt gcggttgaag aaatagtccg gtttaatccg 840
gcaactgaaa ttgagcactt gcgagttgtc accgaggatg tcgtcattgc cggaaccgcg 900
ctatcggcgg ggagcccagc atttacctct atcacttcgg ctaaccgcga ctccgaccaa 960
ttcctggacc ccgatgagtt tgatgtcgaa cgtaatccga acgaacacat agcatttgga 1020
tatggtccac atgcttgccc ggcctcagcg tattcacgca tgtgcttgac gacgttcttc 1080
acctcgctta cccagcgatt tccgcaactt caactcgcaa gaccgtttga ggatttggaa 1140
cgacggggta agggcctaca ttcggtgggg atcaaggaac tccttgttac ctggccgacg 1200

-continued

<210> SEQ ID NO 43
<211> LENGTH: 498
<212> TYPE: DNA
<213> ORGANISM: Mycobacteria tuburculosis

<400> SEQUENCE: 43
gtgcgcattg tcaatgcggc ggacccattt tcgatcaacg atctaggctg tggctatggg 60
gctctactgg actacctaga tgcgcgtggc ttcaaaactg attacaccgg catcgacgtc 120
tcccccgaaa tggtgcgcgc ggccgcacta cgtttcgaag gtcgggcgaa cgcagacttc 180
atctgcgcgg cgcgcataga tcgggaggcg gactatagcg tcgcgagtgg aatattcaat 240
gttcgtctga aatcgttgga cacggaatgg tgcgctcaca tcgaagcgac gctcgacatg 300
ctgaatgccg cgagtcgccg tggcttctct tttaattgcc tgacatctta ttccgatgca 360
tcaaagatgc gcgacgacct gtactatgct gacccatgcg ccctatttga tctctgcaag 420
cgcaggtact ccaagagtgt tgcgcttctg cacgactacg gcttgtatga attcacaatt 480
ctggttagga aggcgtca 498

<210> SEQ ID NO 44
<211> LENGTH: 693
<212> TYPE: DNA
<213> ORGANISM: Mycobacteria tuburculosis

<400> SEQUENCE: 44
ttgaagaaag tcgcgattgt tcaatcaaat tacatacctt ggcgaggata ttttgacctg 60
attgcattcg tcgatgaatt catcatctat gatgacatgc aatataccaa gcgtgattgg 120
cgaaacagaa atcggatcaa aacgagccag gggttacagt ggataactgt tcccgtccag 180
gtgaagggac gtttccatca aaagatacgt gagacgctga tcgacggcac cgattgggcg 240
aaagcgcact ggcgggcact agaattcaac tacagcgcgg ccgctcattt tgcggagatc 300
gctgactggc tcgcgccgat ttacctcgaa gaacagcaca cgaatctttc cttactcaac 360
aggcgtctat tgaatgcgat ttgcagttat ctcggtatca gcacgcgact ggcaaattcg 420
tgggactacg aattagccga cggcaagacc gagagactgg ccaacctctg ccaacaggcc 480
gcagcgaccg aatatgtctc tggcccctca gcccgttcgt atgtcgatga gcgcgtgttc 540
gacgaactta gcatccgggt aacttggttc gattatgacg gctaccgcga ttataagcaa 600
ttgtggggag ggttcgagcc cgccgtgtcg attctggatc tgctctttaa cgtcggagcc 660
gaggctccgg actatttgag gtactgtcgc cag 693

<210> SEQ ID NO 45
<211> LENGTH: 395
<212> TYPE: DNA
<213> ORGANISM: Mycobacteria tuburculosis
<220> FEATURE:
<221> NAME/KEY: misc_feature
<222> LOCATION: (1)...(395)
<223> OTHER INFORMATION: n = A,T,C or G
<220> FEATURE:
<221> NAME/KEY: misc_feature
<222> LOCATION: 27, 44, 104, 119, 180, 224, 237, 245, 254, 301, 327,
370, 385, 393
<223> OTHER INFORMATION: n = A,T,C or G

<400> SEQUENCE: 45
vvmsartgva rhgtsgrgcg dvgargndvs vatrkrsrgd rvgnhgarar rmkrvrgavt 60
asrrwagssr tmgtasvsaa tayaswyavd vstvvgdcwd wgmngrhcsd yamvaaagna 120

-continued dysadytava awaaryagsh wgargcyvat mavsawaarg argrvvvtga aaawgvdrgn 180
stgvvaayva srrwgattva vvkvvgvvaa rwrwaggtgv vvsnaawrgg tashgknssg 240
grdrnvsgka dsknysgkgt grtgavvvvv avagrrvmvg vatatsadva yyvvaavard 300
nggagdaahg drrravgvcv savasvnvav gyvyggakgv vgttvttvtw awvtcvvvsy 360
arkarhdshn gtrsddtaas ttscnvssrg gcnyt 395

<210> SEQ ID NO 46
<211> LENGTH: 879
<212> TYPE: DNA
<213> ORGANISM: Mycobacteria tuburculosis

<400> SEQUENCE: 46
gtgtttgcgt tgagtaataa tctgaaccgt gtgaacgcat gcatggatgg attccttgcc 60
cgtatccgct cacatgttga tgcgcacgcg ccagaattgc gttcactgtt cgatacgatg 120
gcggccgagg cccgatttgc acgcgactgg ctgtccgagg acctcgcgcg gttgcctgtc 180
ggtgcagcat tgctggaagt gggcgggggg gtacttctgc tcagctgtca actggcggcg 240
gagggatttg acatcaccgc catcgagccg acgggtgaag gttttggcaa gttcagacag 300
cttggcgaca tcgtgctgga attggctgca gcacgaccca ccatcgcgcc atgcaaggcg 360
gaagacttta tttccgagaa gcggttcgac ttcgccttct cgctgaatgt gatggagcac 420
atcgaccttc cggatgaggc agtcaggcgg gtatcggaag tgctgaaacc gggggccagt 480
taccacttcc tgtgcccgaa ttacgtattc ccgtacgaac cgcatttcaa tatcccaaca 540
ttcttcacca aagagctgac atgccgggtg atgcgacatc gcatcgaggg caatacgggc 600
atggatgacc cgaagggagt ctggcgttcg ctcaactgga ttacggttcc caaggtgaaa 660
cgctttgcgg cgaaggatgc gacgctgacc ttgcgcttcc accgtgcaat gttggtatgg 720
atgctggaac gcgcgctgac ggataaggaa ttcgctggtc gccgggcaca atggatggtc 780
gctgctattc gctcggcggt gaaattgcgt gtgcatcatc tggcaggcta tgttcccgct 840
acgctgcagc ccatcatgga tgtgcggcta acgaagaggg 879

<210> SEQ ID NO 47
<211> LENGTH: 1296
<212> TYPE: DNA
<213> ORGANISM: Mycobacteria tuburculosis

<400> SEQUENCE: 47
atgtacgaga gacggcatga gcgcggaatg tgcgaccgtg ccgtcgagat gaccgacgtc 60
ggcgctacgg cagcccccac cggacctatc gcgcggggca gcgtcgctcg ggtcggcgcg 120
gcgaccgcgt tggccgttgc ctgcgtctac acggtcatct atctggcggc ccgcgaccta 180
cccccggctt gtttttcgat attcgcggtg ttttgggggg cgctcggcat tgccaccggc 240
gccacccacg gcctcctgca agaaacgacc cgcgaggtcc gctgggtgcg ctccacccaa 300
atagttgcgg gccatcgtac ccatccgctg cgggtggccg ggatgattgg caccgtcgcg 360
gccgtcgtaa ttgcgggtag ctcaccgctg tggagccgac agctattcgt cgaggggcgc 420
tggctgtccg tggggctact cagcgttggg gtggccgggt tctgcgcgca ggcgaccctg 480
ctgggcgcgc tggccggcgt cgaccggtgg acacagtacg ggtcactgat ggtgaccgac 540
gcggtcatcc ggttggcggt cgccgcggca gcggttgtga tcggatgggg tctggccggg 600
tacttgtggg ccgccaccgc gggagcggtg gcgtggctgc tcatgctgat ggcctcgccc 660

-continued

```
accgcgcgca gcgcggccag cctgctgacg cccgggggaa tcgccacgtt cgtgcgcggt    720

gccgctcatt cgataaccgc cgcgggtgcc agcgcgattc tggtaatggg tttcccagtg    780

ttgctcaaag tgacctccga ccagttaggg gcaaagggcg gagcggtcat cctggctgtg    840

accttgacgc gtgcgccgct tctggtccca ctgagcgcga tgcaaggcaa cctgatcgcg    900

catttcgtcg accggcgcac ccaacggctt cgggcgctga tcgcaccggc gctggtcgtc    960

ggcggcatcg gtgcggtcgg gatgttggcc gcagggctta ccggtccctg gttgctgcgt   1020

gttggattcg gccccgacta ccaaactggc ggggcgttgc tggcctggtt gacggcagcg   1080

gcggtagcta tcgccatgct gacgctgacc ggcgccgccg cggtcgcggc cgcactgcac   1140

cgggcgtatt tgctgggctg ggtcagcgcg acggtggcgt cgacgctgtt gctgctgctg   1200

ccgatgccgc tggagacgcg caccgtgatc gcgctgttgt tcggtccaac ggtgggaatc   1260

gccatccatg tggccgcgtt ggcgcggcga cccgac                              1296
```

<210> SEQ ID NO 48
<211> LENGTH: 1020
<212> TYPE: DNA
<213> ORGANISM: M. tuberculosis

<400> SEQUENCE: 48

```
gtgaagcgag cgctcatcac cggaatcacc ggccaggacg gctcgtatct cgccgaactg     60

ctgctggcca aggggtatga ggttcacggg ctcatccggc gcgcttcgac gttcaacacc    120

tcgcggatcg atcacctcta cgtcgacccg caccaaccgg gcgcgcggct gtttctgcac    180

tatggtgacc tgatcgacgg aacccggttg gtgaccctgc tgagcaccat cgaacccgac    240

gaggtgtaca acctggcggc gcagtcacac gtgcgggtga gcttcgacga acccgtgcac    300

accggtgaca ccaccggcat gggatccatg cgactgctgg aagccgttcg gctctctcgg    360

gtgcactgcc gcttctatca ggcgtcctcg tcggagatgt tcggcgcctc gccgccaccg    420

cagaacgagc tgacgccgtt ctacccgcgg tcaccgtatg gcgccgccaa ggtctattcg    480

tactgggcga cccgcaatta tcgcgaagcg tacggattgt tcgccgttaa cggcatcttg    540

ttcaatcacg aatcaccgcg gcgcggtgag acgttcgtga cccgaaagat caccagggcc    600

gtggcacgca tcaaggccgg tatccagtcc gaggtctata tgggcaatct ggatgcggtc    660

cgcgactggg ggtacgcgcc cgaatacgtc gaaggcatgt ggcggatgct gcagaccgac    720

gagcccgacg acttcgtttt ggcgaccggg cgcggtttca ccgtgcgtga gttcgcgcgg    780

gccgcgttcg agcatgccgg tttggactgg cagcagtacg tgaaattcga ccaacgctat    840

ctgcggccca ccgaggtgga ttcgctgatc ggcgacgcga ccaaggctgc cgaattgctg    900

ggctggaggg cttcggtgca cactgacgag ttggctcgga tcatggtcga cgcggacatg    960

gcggcgctgg agtgcgaagg caagccgtgg atcgacaagc cgatgatcgc cggccggaca   1020
```

<210> SEQ ID NO 49
<211> LENGTH: 966
<212> TYPE: DNA
<213> ORGANISM: M. tuberculosis

<400> SEQUENCE: 49

```
atgaacgcgc acacctcggt cggcccgctt gaccgcgcgg cccgggtcta catcgccggg     60

catcgcggcc tggtcgggtc cgcgctgcta cgcacgtttg cgggcgcggg gttcaccaac    120

ctgctggtgc ggtcacgcgc cgagcttgat ctgacggatc gggccgcgac gttcgacttc    180

gttctcgagt cgaggccgca ggtcgtcatc gacgcggcgg cccgggtcgg cggcatcctg    240
```

-continued gccaacgaca cctacccggc cgatttcctg tcggaaaacc tccagatcca ggtcaacctg 300
ctggatgccg ccgtggcggc gcgggtgccg cggctgctgt tcctgggctc gtcgtgcatc 360
tacccgaaac tcgccccgca gccgatcccg gagagcgcgc tgctcaccgg tccgttggag 420
ccgaccaacg acgcgtacgc gatcgccaaa atcgccggca tccttgcggt ccaggcggtg 480
cgccgccaac atggcctgcc gtggatctcg gcgatgccca ccaacctgta cgggccaggc 540
gacaactttt cgccgtccgg ctcgcatctg ctgccggcac tcatccgccg ctatgacgag 600
gccaaagcca gtggcgcgcc caacgtgacc aactggggca ccggcacgcc ccgacgggag 660
ttgctgcacg tcgacgacct ggcgagcgca tgcctgtatc tgctggaaca tttcgacggg 720
ccgacccatg tcaacgtggg aaccggcatc gaccacacca tcggcgagat cgccgagatg 780
gtcgcctcgg cggtaggcta tagcggcgaa acccgctggg atccaagcaa accggacgga 840
acaccacgca aactgctgga tgtttcggtg ctacgggagg cgggatggcg gccttcgatc 900
gcgctgcgcg acggcatcga ggcgacggtg gcgtggtatc gcgagcacgc gggaacggtt 960
cggcaa 966

<210> SEQ ID NO 50
<211> LENGTH: 729
<212> TYPE: DNA
<213> ORGANISM: Mycobacteria tuberculosis

<400> SEQUENCE: 50
atgaggctgg cccgtcgcgc tcggaacatc ttgcgtcgca acggcatcga ggtgtcgcgc 60
tactttgccg aactggactg ggaacgcaat ttcttgcgcc aactgcaatc gcatcgggtc 120
agtgccgtgc tcgatgtcgg ggccaattcg gggcagtacg ccaggggtct gcgcggcgcg 180
ggcttcgcgg gccgcatcgt ctcgttcgag ccgctgcccg ggccctttgc cgtcttgcag 240
cgcagcgcct ccacggaccc gttgtgggaa tgccggcgct gtgcgctggg cgatgtcgat 300
ggaaccatct cgatcaacgt cgccggcaac gagggcgcca gcagttccgt cttgccgatg 360
ttgaaacgac atcaggacgc ctttccacca gccaactacg tgggcgccca acgggtgccg 420
atacatcgac tcgattccgt ggctgcagac gttctgcggc ccaacgatat tgcgttcttg 480
aagatcgacg ttcaaggatt cgagaagcag gtgatcgcgg gtggcgattc aacggtgcac 540
gaccgatgcg tcggcatgca gctcgagctg tctttccagc cgttgtacga gggtggcatg 600
ctcatccgcg aggcgctcga tctcgtggat tcgttgggct ttacgctctc gggattgcaa 660
cccggtttca ccgacccccg caacggtcga atgctgcagg ccgatggcat cttcttccgg 720
ggcagcgat 729

<210> SEQ ID NO 51
<211> LENGTH: 786
<212> TYPE: DNA
<213> ORGANISM: Mycobacteria tuburculosis

<400> SEQUENCE: 51
gtgacgtctg ctccgaccgt ctcggtgata acgatctcgt tcaacgacct cgacgggttg 60
cagcgcacgg tgaaaagtgt gcgggcgcaa cgctaccggg gacgcatcga gcacatcgta 120
atcgacggtg gcagcggcga cgacgtggtg gcatacctgt ccgggtgtga accaggcttc 180
gcgtattggc agtccgagcc cgacggcggg cggtacgacg cgatgaacca gggcatcgcg 240
cacgcatcgg gtgatctgtt gtggttcttg cactccgccg atcgtttttc cgggcccgac 300

-continued

```
gtggtagccc aggccgtgga ggcgctatcc ggcaagggac cggtgtccga attgtggggc    360

ttcgggatgg atcgtctcgt cgggctcgat cgggtgcgcg gcccgatacc tttcagcctg    420

cgcaaattcc tggccggcaa gcaggttgtt ccgcatcaag catcgttctt cggatcatcg    480

ctggtggcca agatcggtgg ctacgacctt gatttcggga tcgccgccga ccaggaattc    540

atattgcggg ccgcgctggt atgcgagccg gtcacgattc ggtgtgtgct gtgcgagttc    600

gacaccacgg gcgtcggctc gcaccgggaa ccaagcgcgg tcttcggtga tctgcgccgc    660

atgggcgacc ttcatcgccg ctacccgttc gggggaaggc gaatatcaca tgcctaccta    720

cgcggccggg agttctacgc ctacaacagt cgattctggg aaaacgtctt cacgcgaatg    780

tcgaaa                                                               786
```

```
<210> SEQ ID NO 52
<211> LENGTH: 894
<212> TYPE: DNA
<213> ORGANISM: Mycobacteria tuburculosis

<400> SEQUENCE: 52

atgtcgacaa acccaggacc agccgaaggg gctaaccaag tgatggcaca ggaacattcg     60

gccggcgcgg tacaattcac cgcccacaac gttcgcctcg acgacggaac cttgacgata    120

ccggagtcct cgcgcacgtt agacgaatcg tcctggttca tctcggcgcg cgggattctg    180

gaaaccgtct ttcccgggga caagagccac ctacgcctgg ccgatgtcgg ctgcttggaa    240

ggcgggtacg cggtcgggtt cgcgcgcatg ggatttcagg tcctcgggat cgaggttcgc    300

gagctgaaca tggcggcctg caactacatc aaatcgaaga ccaacctgcc gaatctccgg    360

ttcgtccacg acaacgccct caacatcgcc aaccacgggc tcttcgatac cgtcttctgc    420

tgcggcctct tctaccacct ggagaatccg aagcaatacc tggaaaccct ctcgtcggta    480

acgaacaagc tgctgattct ccagacgcac ttctcgatca tcaaccggag cgataaatgg    540

ctccggttgc ccacgacggc acgacaattg accgatcggt tgctgcggcg gccggcgccg    600

gtgaagttca tgctctcggc gcccaccgaa catgagggac ttcccggtag gtggtttacc    660

gagttttccg acgaccgctc gtttggccag cgcgacaccg caaaatgggc gtcctgggac    720

aatcgccggt cattctggat tcaacgcgag cacctacttc aggccatcaa agacgtcggc    780

gtcgacctgg tgatggagga gtacgacaac ttggaaccaa gcatcgccga gtcgttgctc    840

ggaggttcct atgcggcgaa tcttcgaggc accttcatcg gtatcaagac ccgg          894
```

```
<210> SEQ ID NO 53
<211> LENGTH: 1119
<212> TYPE: DNA
<213> ORGANISM: Mycobacteria tuburculosis

<400> SEQUENCE: 53

gtgccgtacg tccgccgacc accaggccac gacggccgac ggccggcggg cacaggcgat     60

tcacgttcgc catcgcaata cccttgcggc cgcgcaggaa aagggccgac ggtgagtccc    120

cagctttgcc ccaaggtgag catcgtctcg accactcaca accaggcggg ctacgcccgt    180

caggccttcg acagctttct cgaccagcaa accgacttcc cggtggagat catcgtcgcc    240

gacgacgcgt cgaccgatgc caccccggcg atcatccgtg agtacgccga gcggtacccg    300

cacgtgttcc ggccgatctt caggaccgaa aacctcggcc tcaatgggaa cctgaccggc    360

gccctgtcgg ccgctcgcgg cgagtacgtc gcgttgtgcg aggcggacga ctactggatc    420

gatccgctga agctaagcaa acaggtcgca ttcctcgacc ggcaccccaa gacgacggtg    480
```

-continued tgcttccatc ccgtccgagt gatatgggag gacggccatg ccaaggactc gaagttcccc 540
ccggttcggg tgcggggcaa cttgagcctg gatgcgttga tcttgatgaa cttcatccag 600
accaactcgg ccgtgtaccg tcgcctcgag cgctacgacg acattcctgc cgacgtcatg 660
cccctggact ggtatctgca cgtccggcac gcggtgcatg gcgacatcgc catgttgccc 720
gacaccatgg ccgtgtatcg ccgccacgcc caaggcatgt ggcacaacca ggtggtggac 780
ccgccaaagt tctggttgac gcagggtccg gggcatgcgg cgacgtttga cgcgatgctc 840
gacctgttcc cgggagaccc cgcgcgcgag gagctcatcg ccgtcatggc cgactggatc 900
cttcgccaga tcgccaacgt tccaggcccg gaggggcgcg ccgcgctgca ggaaaccatc 960
gcgcgccatc cccggatcgc catgctggcg ctgcagcacc gcggggcgac acccgcgcgg 1020
cggctcaaga cccagtggcg caagctcgcc gccgcgacgc cgagccgcag gggctcgtg 1080 gatgtgtggc cctcccggct ccgacgcggc tgtcgagcc 1119

<210> SEQ ID NO 54
<211> LENGTH: 282
<212> TYPE: DNA
<213> ORGANISM: Mycobacteria tuburculosis

<400> SEQUENCE: 54
atgaccatca actatcagtt cggtgatgtc gacgctcatg gcgccatgat ccgcgctcag 60
gccgggttgc tggaggcgga gcatcaggcc atcgttcgtg atgtgttggc cgcgggtgac 120
ttttggggcg gcgccggttc ggtggcttgc caggagttca tcacccagct gggccgtaac 180
ttccaggtga tctacgagca ggccaacgcc cacgggcaga aggtgcaggc tgccggcaac 240
aacatggcac aaaccgacag cgccgtcggc tccagctggg cc 282

<210> SEQ ID NO 55
<211> LENGTH: 294
<212> TYPE: DNA
<213> ORGANISM: Mycobacteria tuburculosis

<400> SEQUENCE: 55
atggcaacac gttttatgac ggatccgcac gcgatgcggg acatggcggg ccgttttgag 60
gtgcacgccc agacggtgga ggacgaggct cgccggatgt gggcgtccgc gcaaaacatc 120
tcgggcgcgg gctggagtgg catggccgag gcgacctcgc tagacaccat ggcccagatg 180
aatcaggcgt ttcgcaacat cgtgaacatg ctgcacgggg tgcgtgacgg gctggttcgc 240
gacgccaaca actacgagca gcaagagcag gcctcccagc agatcctcag cagc 294

<210> SEQ ID NO 56
<211> LENGTH: 324
<212> TYPE: DNA
<213> ORGANISM: Mycobacteria tuburculosis

<400> SEQUENCE: 56
gtgcttttgc ctcttggtcc gcctttgccg cccgacgcgg tggtggcgaa acgggctgag 60
tcgggaatgc tcggcgggtt gtcggttccg ctcagctggg gagtggctgt gccacccgat 120
gattatgacc actgggcgcc tgcgccggag gacggcgccg atgtcgatgt ccaggcggcc 180
gaaggggcgg acgcagaggc cgcggccatg gacgagtggg atgagtggca ggcgtggaac 240
gagtgggtgg cggagaacgc tgaaccccgc tttgaggtgc cacggagtag cagcagcgtg 300
attccgcatt ctccggcggc cggc 324

-continued

<210> SEQ ID NO 57
<211> LENGTH: 1524
<212> TYPE: DNA
<213> ORGANISM: M. tuberculosis

<400> SEQUENCE: 57
atgtcacgcc gagcattcct ggctaaggcg gctggagccg gggcagcggc ggttttgacg 60
gactgggccg caccggtgat cgaaaaggcc tatggtgccg gtccctgctc gggtcatttg 120
accgatatcg agcacatcgt gctgtgccta caggagaaca ggtcgttcga tcactatttc 180
ggcacgcttt ctgccgtcga cgggttcgac actccgacgc cgctgtttca acaaaagggc 240
tggaacccgg agacgcaggc gctggacccc accggcatta cgctgcccta ccgcatcaat 300
accaccgggg gtcccaacgg ggttggcgag tgcgtcaacg acccagacca ccagtggatt 360
gccgcgcact tgtcatggaa cggcggcgcc aatgacggct ggctgccggc gcaggcgcgg 420
acccggtcgg tggccaacac gcccgtggtg atgggctatt acgcacgtcc tgacataccg 480
atccactact tgttggccga taccttcacg atctgcgacc agtacttctc gtcgcttctt 540
ggcgggacga tgcctaaccg gctctattgg atcagcgcca ccgtcaatcc cgacggggat 600
caaggtgggc cgcagatcgt cgaacccgcc atccagccga agttgacctt cacctggcgc 660
atcatgccgc agaacctcag tgacgccggc atcagttgga aggtgtacaa cagcaagctg 720
ctcggcgggc tcaacgacac ttccttgagc cgtaacgggt atgtgggcag tttcaaacag 780
gccgcagatc cgaggtcgga cctggcccgt tatggcatcg ccccggccta cccgtgggat 840
ttcatccgcg acgtcatcaa caacacgctg ccccaggtgt cctgggtcgt tccgttgacc 900
gtcgagtccg aacatccgtc attcccggtg gcagtcggtg cggtgacgat cgtgaacttg 960
ataagggtgt tgctgcgcaa tccggcggtg tgggagaaaa ccgcgttgat catcgcctat 1020
gacgaacatg gcggcttctt cgaccacgtc acaccgctca ccgcgccgga gggcacaccc 1080
ggcgaatgga ttcccaacag tgttgacatc gacaaggtcg acggctccgg cggaatacgt 1140
ggacccatcg gcttgggctt tcgcgtgccc tgcttcgtca tttcgcctta cagtcgcggc 1200
gggctgatgg tccatgatcg gttcgaccac acatcgcagc tgcaattgat cggcaagcgt 1260
ttcggggtgc cggttcccaa cttgacaccc tggcgtgcca gtgtcaccgg cgatatgacg 1320
tcggcattca atttcgcggc cccgccggac ccgtcgccac ccaatctgga ccacccggtc 1380
cgtcaattgc cgaaggtcgc caagtgcgtg cccaatgtgg tgctgggttt cttgaacgaa 1440
ggcctgccgt atcgggtgcc ctacccccaa acaacgccag tccaggaatc cggtcccgcg 1500
cggccgattc ccagcggcat ctgc 1524

<210> SEQ ID NO 58
<211> LENGTH: 1536
<212> TYPE: DNA
<213> ORGANISM: M. tuberculosis

<400> SEQUENCE: 58
atgtcacgtc gagagttttt gacaaagctc actggcgcag gcgcagcggc attcctgatg 60
gactgggctg caccggtgat tgaaaaggcc tacggcgccg ggccttgtcc cggacatttg 120
accgacatcg agcatatcgt gttgctgatg caggagaacc ggtcattcga ccactatttc 180
ggaacgcttt ccagcaccaa tgggttcaac gccgcgtcgc cggcattcca acaaatgggt 240
tggaacccca tgacgcaggc gttggacccc gccggggtca ccattccgtt ccgcttggac 300
accacccgag gccccttcct ggacggcgag tgcgtcaacg accccgagca ccagtgggtg 360

-continued gggatgcacc tggcctggaa cggtggtgcc aacgacaact ggctgccggc gcaggcgacc 420
acccgcgcag gaccatatgt ccctttgacc atgggttact acacgcgcca agacatcccg 480
atccactatc tgctggccga cacgttcacc atctgcgacg gctaccattg ctcgctgctg 540
acgggcaccc tgcccaaccg gctctactgg ttgagcgcca acatcgaccc cgccggcacc 600
gacgggggac cccaattggt agagccgggc ttcctgccgc tgcagcaatt cagttggcgc 660
atcatgccgg aaaacctcga agatgccggg gtcagctgga aggtgtacca gaacaagggc 720
ctcgggcgat tcatcaacac gcccatcagc aataacgggc tggtgcaggc cttccgccag 780
gcagctgatc cgaggtcgaa cttggcccgc tacggtatcg ccccgaccta ccctggggac 840
ttcgctgccg acgtcagggc caaccggcta cccaaggtct cctggttagt tcccaacatc 900
ctgcagtccg aacaccccgc cctgccggta gcgcttggcg cggtgtccat ggtgaccgcg 960
ctgcggatct tgctgtccaa tcccgcggtg tgggaaaaga ccgcacttat cgtcagctat 1020
gacgagaacg gcggcttctt cgaccacgtc acgcccccca cggcaccgcc cgggacaccc 1080
ggcgaattcg tcacggtgcc caacatcgac gcagtacccg ggtccggtgg cattcgtggt 1140
ccgctcggtc tgggttttcg cgttccctgc attgtcattt cgccgtacag ccgcggcccg 1200
ctgatggtct ccgacacgtt cgaccacacc tcgcaattga agttgattcg cgcccggttc 1260
ggcgtgccgg ttcccaacat gaccgcctgg cgcgacggcg tggttggcga catgacctca 1320
gcgttcaact ttgcgactcc accgaattcg accagaccca acttgagcca cccgttgctg 1380
ggagcgctgc cgaagctgcc gcagtgcatc cctaacgtgg tgttgggaac caccgacggc 1440
gcgttgccga gcattcccta tcgggtgccc tatccgcagg tgatgccaac tcaggaaacc 1500
acacccgtcc gcgggactcc cagcgggctg tgcagc 1536

<210> SEQ ID NO 59
<211> LENGTH: 1536
<212> TYPE: DNA
<213> ORGANISM: M. tuberculosis

<400> SEQUENCE: 59
atgtcacgtc gagagttttt gacaaagctc actggcgcag gcgcagcggc attcctgatg 60
gactgggctg caccggtgat tgaaaaggcc tacggcgccg ggccttgtcc cggacatttg 120
accgacatcg agcatatcgt gttgctgatg caggagaacc ggtcattcga ccactatttc 180
ggaacgcttt ccagcaccaa tgggttcaac gccgcgtcgc cggcattcca acaaatgggt 240
tggaacccca tgacgcaggc gttggacccc gccggggtca ccattccgtt ccgcttggac 300
accacccgag gccccttcct ggacggcgag tgcgtcaacg accccgagca ccagtgggtg 360
gggatgcacc tggcctggaa cggtggtgcc aacgacaact ggctgccggc gcaggcgacc 420
acccgcgcag gaccatatgt ccctttgacc atgggttact acacgcgcca agacatcccg 480
atccactatc tgctggccga cacgttcacc atctgcgacg gctaccattg ctcgctgctg 540
acgggcaccc tgcccaaccg gctctactgg ttgagcgcca acatcgaccc cgccggcacc 600
gacgggggac cccaattggt agagccgggc ttcctgccgc tgcagcaatt cagttggcgc 660
atcatgccgg aaaacctcga agatgccggg gtcagctgga aggtgtacca gaacaagggc 720
ctcgggcgat tcatcaacac gcccatcagc aataacgggc tggtgcaggc cttccgccag 780
gcagctgatc cgaggtcgaa cttggcccgc tacggtatcg ccccgaccta ccctggggac 840
ttcgctgccg acgtcagggc caaccggcta cccaaggtct cctggttagt tcccaacatc 900

-continued

```
ctgcagtccg aacaccccgc cctgccggta gcgcttggcg cggtgtccat ggtgaccgcg    960

ctgcggatct tgctgtccaa tcccgcggtg tgggaaaaga ccgcacttat cgtcagctat   1020

gacgagaacg gcggcttctt cgaccacgtc acgcccccca cggcaccgcc cgggacaccc   1080

ggcgaattcg tcacggtgcc caacatcgac gcagtacccg ggtccggtgg cattcgtggt   1140

ccgctcggtc tgggttttcg cgttccctgc attgtcattt cgccgtacag ccgcggcccg   1200

ctgatggtct ccgacacgtt cgaccacacc tcgcaattga agttgattcg cgcccggttc   1260

ggcgtgccgg ttcccaacat gaccgcctgg cgcgacggcg tggttggcga catgacctca   1320

gcgttcaact ttgcgactcc accgaattcg accagaccca acttgagcca cccgttgctg   1380

ggagcgctgc cgaagctgcc gcagtgcatc cctaacgtgg tgttgggaac caccgacggc   1440

gcgttgccga gcattcccta tcgggtgccc tatccgcagg tgatgccaac tcaggaaacc   1500

acacccgtcc gcgggactcc cagcgggctg tgcagc                             1536
```

<210> SEQ ID NO 60
<211> LENGTH: 1173
<212> TYPE: DNA
<213> ORGANISM: Mycobacteria tuburculosis

<400> SEQUENCE: 60

```
atgattttgg atttttcgtg gttgccgccg gagatcaact cggcgcggat ctatgccggt     60

gcggggtcgg ggccgttgtt tatggcggcg gcggcgtggg aggggttggc tgcggatttg    120

cgggcctcgg cgtcctcgtt tgatgcggtg atcgccgggt tggcggctgg gccgtggtcg    180

ggtccggcgt cggtggcgat ggcgggggcg gcggcgccgt atgtggggtg gttgagtgcg    240

gcggccgggc aggcggagtt gtcggctggt caggctaccg cggcggcgac ggcgtttgag    300

gcggcgttgg cggccacggt gcatccggcg gcggtgacgg cgaatcgggt gttgttgggg    360

gcgttggtgg cgacgaacat tttgggtcag aacacgccgg cgattgcggc cactgagttc    420

gattatgtgg agatgtgggc tcaggacgtg ggtgcgatgg tggggtatca cgcgggggcg    480

gcggcggtgg ctgagacgtt gacgccgttt agtgtgccgc cgctggattt ggcggggttg    540

gcttcccagg ccggtgcgca gttgaccggg atggcgacgt cggtttcggc tgcgttgtct    600

ccgatcgcgg agggtgcggt ggagggggtg ccggctgtgg tggctgcggc gcagtcggtg    660

gcggcggggt tgccggtgga tgcggcgctg caggtggggc aggccgcggc gtatccggcc    720

agtatgttga ttgggccgat gatgcagttg gcgcagatgg ggactacggc caacacggct    780

gggttggccg gtgcggaggc tgcggggttg gctgcggcgg atgtgccgac gtttgccggt    840

gatatcgctt cggggacggg cctaggtggt gccggtggtc tgggtgcggg gatgtcggcg    900

gagttgggta aggcgcggtt ggtgggggcg atgtcggtgc ctccgacctg ggaggggtcg    960

gttcctgcgc ggatggccag ttcggcgatg gcgggtttgg gggctatgcc tgctgaggtg   1020

ccggcggcag gcgggcccat ggggatgatg ccgatgccga tgggtatggg gggtgctggg   1080

gcgggtatgc cggccgggat gatgggccgc ggtggcgcaa atccgcatgt ggtgcaggct   1140

cggcccagtg tggtgccgcg ggtcgggatc gga                                1173
```

<210> SEQ ID NO 61
<211> LENGTH: 1062
<212> TYPE: DNA
<213> ORGANISM: Mycobacteria tuburculosis

<400> SEQUENCE: 61

```
atgccggggc ggttcagaaa cttcggtagc caaaacctgg gtagcggcaa catcggcagc     60
```

-continued

```
accaacgtgg gcagcggcaa catcggcagc accaacgtgg gcagcggcaa catcggcgac    120

acgaacttcg gtaacggaaa caacggcaac ttcaactttg gtagcggcaa taccggcagt    180

aacaacatcg gcttcggaaa caccggcagc gggaatttcg gtttcggaaa cacgggcaac    240

aacaacatcg gtatcgggct caccggcgat ggtcagatcg gcatcggcgg actgaactcg    300

ggcagcggaa acatcggttt cgggaactcc ggcaccggaa acgtcggttt gttcaactcc    360

ggcaccggca acgtaggctt cgggaactcc ggtactgcga acactggatt cgggaacgcg    420

ggcaacgtca acaccggatt ttggaacggc ggcagcacaa acactggcct cgctaacgcc    480

ggcgccggca acacaggctt tttcgacgct ggcaactaca acttcggcag tcttaacgcc    540

ggaaacataa actcgagttt tgggaattcg ggtgacggca acagtggttt cctcaatgct    600

ggcgacgtca actccggtgt gggcaatgcg ggtgatgtca acactggctt agggaactcg    660

ggcaacatca atactggtgg gtttaatccg ggcacgctca acacgggctt cttcagcgcg    720

atgacccaag ctggtccgaa ttcgggcttc ttcaacgccg gtaccggtaa ctctggtttc    780

gggcacaacg acccggctgg cagtggcaac tcgggcattc agaactcggg cttcggcaac    840

tcgggctatg tcaataccag caccacaagc atgttcggcg gtaactcagg ggtgctcaac    900

acgggctacg gcaactcagg tttctataac gcggccgtca acaacaccgg gatttttgtg    960

accggcgtga tgagttcggg atttttcaat tttgggacgg gcaactcggg cctgctggtc   1020

agcggcaatg ggctttcggg tttcttcaag aacttgttcg ga                      1062
```

<210> SEQ ID NO 62
<211> LENGTH: 654
<212> TYPE: DNA
<213> ORGANISM: Mycobacteria tuburculosis

<400> SEQUENCE: 62

```
atgagccgac tcctagcttt gctgtgcgct gcggtatgca cgggctgcgt tgctgtggtt     60

ctcgcgccag tgagcctggc cgtcgtcaac ccgtggttcg cgaactcggt cggcaatgcc    120

actcaggtgg tttcggtggt gggaaccggc ggttcgacgg ccaagatgga tgtctaccaa    180

cgcaccgccg ccggctggca gccgctcaag accggtatca ccacccatat cggttcggcg    240

ggcatggcgc cggaagccaa gagcggatat ccggccactc cgatgggggt ttacagcctg    300

gactccgctt ttggcaccgc gccgaatccc ggtggcgggt tgccgtatac ccaagtcgga    360

cccaatcact ggtggagtgg cgacgacaat agccccacct ttaactccat gcaggtctgt    420

cagaagtccc agtgcccgtt cagcacggcc gacagcgaga acctgcaaat cccgcagtac    480

aagcattcgg tcgtgatggg cgtcaacaag gccaaggtcc caggcaaagg ctccgcgttc    540

ttctttcaca ccaccgacgg cgggcccacc gcgggttgtg tggcgatcga cgatgccacg    600

ctggtgcaga tcatccgttg gctgcggcct ggtgcggtga tcgcgatcgc caag          654
```

<210> SEQ ID NO 63
<211> LENGTH: 489
<212> TYPE: DNA
<213> ORGANISM: Mycobacteria tuburculosis

<400> SEQUENCE: 63

```
gtgtgctgca atggcgtggt gactccgggt gatccagccg acattgcagc gatcaaacag     60

ctcaaatacc ggtatctgcg ggcattggac accaagcatt gggacgactt caccgacacc    120

ctggccgagg atgtcaccgg cgattacggg tcatcggtcg gtacggagct gcacttcacc    180
```

-continued

```
aaccgcgccg acctggtcga ctacctgcgc caggcactcg gcccgggtgt catcaccgaa    240

caccgggtca cccatccgga aatcaccgtg accggcgata ccgcaaccgg catctggtac    300

ctgcaagacc gggtcatcgt cgccgagttc aatttcatgc tcatcggcgc cgcgttctac    360

cacgaccagt accgacgaac caccgacggc tggcggatca gcgccaccgg ctacgaccga    420

acctacgagg cgaccatgtc gttggcgggc cttaacttca acatcaggcc gggccgcgcg    480

ctggccgat                                                            489
```

<210> SEQ ID NO 64
<211> LENGTH: 1227
<212> TYPE: DNA
<213> ORGANISM: Mycobacteria tuburculosis

<400> SEQUENCE: 64

```
atgagccaat cccggtacgc ggggttgtcc cgcagcgagc tggcagttct gttacccgag     60

ctgttgttga tcggccagct gatcgaccga tcgggcatgg cctggtgtat acaggcattc    120

ggccgccagg agatgctgca gatcgccatc gaggagtggg cgggcgccag cccgatctac    180

accaagcgca tgcaaaaggc gctgaacttc gagggcgacg acgtgcccac catcttcaag    240

gggctacagc tcgacatcgg cgcgccgccg caattcatgg acttccgttt caccctgcac    300

gaccgctggc acggcgagtt tcacctcgac cactgcggtg cgctgctcga cgtggagccg    360

atgggcgacg actacgtcgt cggcatgtgc cacaccatcg aagatccgac gttcgacgcc    420

accgcgatcg cgaccaaccc gcgcgcgcag gtgcgcccca tccaccggcc gccccgcaag    480

ccggccgacc ggcatccgca ctgtgcgtgg accgtcatca tcgacgagtc ctatcccgag    540

gctgagggta ttccggcgct ggacgcggtc cgtgaaacca aagctgccac ctgggaatta    600

gacaacgtcg atgcgtctga cgacgggctg gtggactatt cgggtccgct ggtgtccgac    660

ctggacttcg gggcgttctc gcattccgca ctggtgcgga tggccgatga ggtctgcctg    720

caaatgcacc tgctgaatct gtcgttcgcc attgccgtgc ggaaacgggc caaagccgat    780

gctcaactgg ccatttcggt gaacacccgc cagttgatcg gagtggccgg gctgggcgca    840

gaacgcattc accgtgcgat ggctttaccc ggcggaatcg aaggcgcgtt aggtgtgctg    900

gagctacacc cgctgctcaa cccggccggt tacgtgctgg ccgaaacgtc gccggaccgt    960

ctggtggtgc acaactcgcc agcccacgcc gacggcgcct ggatttcgtt gtgcacaccg   1020

gcatccgtgc agccgttgca ggccatcgcc accgctgtag acccgcatct gaaggttcgg   1080

atcagcggga cggacaccga ctggaccgcg gaactcatcg aggccgatgc cccagcgagc   1140

gaactgccgg aggtgttggt agccaaggtc agtcgcggat cggtcttcca gttcgagccg   1200

aggcgctcac tgccgttgac cgtgaaa                                       1227
```

<210> SEQ ID NO 65
<211> LENGTH: 1860
<212> TYPE: DNA
<213> ORGANISM: Mycobacteria tuburculosis

<400> SEQUENCE: 65

```
atgtacgacc cgctggggtt gtcgatcggg accacaaacc tggtcgcggc gggtaacgga     60

ggtccgccgg ttactcgtcg cgccgtgctg accctgtacc cgcattgcgc accgaaaatc    120

ggtgtgccta gccagaaccc gaacttgatc gagccgggcg ccctaatgag cggctttgtt    180

gagcgcattg gagatgcggt ggcgctggtg tctcccgacg gatccgtgca cgatccagac    240

ctcttgctgg tcgaggcgct ggatgcgatg gtgctgaccg ccggtgcgga cgcgagttcc    300
```

-continued

```
tcggagatcg ccattgccgt tcccgcgcat tggaagcccg gagctgtaca cgcactgcgt    360

aacggtttgc ggacgcacgt cggcttcgtc cgcagcggca tggcgccgcg cctggtttcc    420

gatgcgatcg cggcgttgac cgcggtgaac tcggaattgg gcctgcccca cggcagtgtg    480

gtggggttgc ttgatttcgg tggctccgcg acttacgtca ccttggtgga gaccaagtcg    540

gattccagga cgtcggattt ccagcccgtt agtgccacgg cacggtacca ggacttttcc    600

ggtagtcaga tcgaccaggc tttgctgctt cgggtcatcg accaattcgg gtacggcgat    660

gacgtcgatc cggccagtac cgccgcggtc gggcaactcg gccaactcag ggagcagtgc    720

cgtgcggcaa aggaacgact gtccaccgac gttgccacgg aattgttcgc tgagcttgcc    780

gggtgcagct cgagcatcga gatgactcgg gaacagctcg aagacctgat ccaggatcca    840

ttgaccggct tcatctacgc gttcgacgac atgctggcgc gccacaacgc gagctgggcg    900

gatctcgcgg cggtggtcac cgtcggcggt ggtgccaata ttccccttgt gactcaacgt    960

ctttcgttcc acactcgtcg acctgtgctg accgcgtcgc aacccgggtg cgcggcggcg   1020

atgggtgcgt tgctgctcgc caaccgtggg ggagagcgcg attcgcgaac gcggacgtcc   1080

atcggcctcg ccacggccgc agccgccggc accagtgtca tcgagctgcc ggccggcgac   1140

gtcatggtca tcgaccatga ggccttgacc gatcgcgagt tggcctggtc gcagaccgac   1200

ttcccaagcg aagctccggc gcgtttcgag ggcgactcgt ataacgaagg cggcccctgc   1260

tggtcgatgc gtctgaacgc ggtcgagccc cccaaaggac cagcgtggcg gcgaatccgg   1320

gtgtcgcagt tgctcatcgg ggtgtcggcg gtagtggcca tgaccgcgat cgggggcgtg   1380

gcattgacgt tgacagccat cgagagacgc ccaagcccgc taccaacccc aattgtgccc   1440

ggcctggccc cgatgccgcc cggatccgtc gtgcctagct cgcgcgcacc gaccccgccg   1500

ccaccgccgt cgaccgttgc gccgcttccc agtgcggcac cggcccccgac gacggtcgcg   1560

ccggcaccgc cgccgcccac acaggtggtg acgaccacga cagcgccacc cgtcaccacg   1620

acgccgaggc cgtcgccgac caccacaacg accaccgcgc caccgtcgac aacgacgaca   1680

accgagccgc cggtgacgac cacttcgacg attccaacga ttccgacgac tacgacgacg   1740

gtgaagatga ccacggagtg gttgcacgtc ccgtttttgc ccgttccgat cccggtcccg   1800

attccgcaaa atccgggtgc cggcgaaccg cagaacccgt tcggaagcct tggctctggg   1860
```

<210> SEQ ID NO 66
<211> LENGTH: 720
<212> TYPE: DNA
<213> ORGANISM: M. tuberculosis

<400> SEQUENCE: 66

```
atgatccgat tggtccgtca ttcgatcgcc ctggtggccg ccggccttgc cgccgcattg     60

tcggggtgcg attcccacaa ctcgggatcg ctcggtgccg atccgcggca ggtgaccgtg    120

ttcggatccg ggcaagtgca gggtgtgccg gacacgttga tcgctgacgt cggcattcag    180

gtcaccgcgg ccgacgtcac cagcgcgatg aaccagacca atgatcgcca gcaagcggtg    240

atcgatgcac tggtgggtgc cggcctggac cgcaaggaca tccgcaccac cagggtcacc    300

gtggcaccgc agtacagcaa tccggagccg gccggaaccg ccaccatcac cgggtatcgg    360

gcagacaacg acatcgaggt gaagatccac ccgaccgacg ccgcgtcgcg gctgctggcc    420

ctcgtcgtca gcaccggcgg tgacgccacc cggatcagct cggtcagcta ctcgattggc    480

gacgactcgc agctggtgaa ggatgcccgg gcgcgcgcct tccaagacgc caagaaccgt    540
```

-continued

```
gcggaccagt acgcacaact gtcggggctg cggctaggca aggtgatctc gatctccgag    600

gcatctggcg ccgcgcccac gcacgaggcg ccggcgccgc cgcgcggcct atccgcggtg    660

ccgctggaac ccggccagca gacggtgggc ttctcggtca cggtggtctg ggaactgacc    720
```

<210> SEQ ID NO 67
<211> LENGTH: 297
<212> TYPE: DNA
<213> ORGANISM: Mycobacteria tuburculosis

<400> SEQUENCE: 67

```
atgtcgatca tgcacgccga gccagagatg ctggctgcga ccgcgggga actgcagtcg      60

atcaacgccg ttgcgcgggc cggaaatgca gcggtggcgg gcccgacgac gggtgtggtt    120

ccggccgccg ctgatttggt gtccctgcta accgcctccc agtttgccgc gcatgcacag    180

ctgtaccagg cgattagtgc cgaggcgatg gcggtccagg agcagttggc gaccacgctg    240

ggcatcagcg ccggttcata tgcggccacc gaggctgcca acgccgccac gatcgct       297
```

<210> SEQ ID NO 68
<211> LENGTH: 1239
<212> TYPE: DNA
<213> ORGANISM: Mycobacteria tuburculosis

<400> SEQUENCE: 68

```
atgctggact ttgctcagtt accgccggag gtcaactccg cgctgatgta cgccggaccc     60

ggttcgggac cgatgctggc tgccgcggcg gcctgggagg cgctggccgc cgagttgcaa    120

accacggcgt ccacctacga cgctctgatc actggcctgg ccgacgggcc atggcagggg    180

tcctccgcgg cgtccatggt ggctgccgcc acgccccagg tggcgtggtt gaggagcacc    240

gccgggcagg ccgagcaagc cggcagccaa gcggtggcag cggcgagtgc ttatgaggcg    300

gcgtttttcg cgaccgtgcc gcccccggag atcgcggcca acagggcgtt gttgatggcg    360

ttgctggcga cgaacttcct tggccagaac acggcggcga tcgcggccac cgaggcgcaa    420

tacgccgaga tgtgggccca ggatgcggcc gcgatgtacg gctatgctgg cgcgtcggcg    480

gcggcgacgc agttgtcgcc attcaatccg gcggcgcaga ccatcaaccc ggccgggctg    540

gccagccagg ccgcatctgt cggacaagct gtcagcgggg ccgcaaatgc gcaagcactc    600

accgacattc ctaaagcgtt gtttgggctt agcggaatct tcaccaatga accgccttgg    660

ctcaccgacc ttggcaaggc gctcggtttg accgggcaca cctggtcctc ggacggtagc    720

gggctcatcg tgggcggagt gcttggcgac tttgtgcagg gtgtgaccgg gtcggccgaa    780

cttgatgcca gcgtggccat ggacacgttc ggcaaatggg tctcgcccgc tcggctcatg    840

gtcacccaat tcaaggacta ctttggcctg gcgcacgacc tgccgaagtg ggcgagtgaa    900

ggcgccaaag ccgccggtga ggccgccaag gcgttgccgg ccgccgttcc ggccattccg    960

agtgctggcc tgagcggcgt tgcgggcgcc gtcggtcagg cggcgtcggt cgggggattg   1020

aaggttccgg ccgtttggac cgccacgacc ccggcggcga gccccgcggt gctggcggcg   1080

tccaacggcc tcggagccgc ggccgccgct gaaggttcga cacacgcgtt tggcgggatg   1140

ccgctcatgg gtagcggtgc cggacgtgcg tttaacaact tcgctgcccc tcgatacgga   1200

ttcaagccga ccgtgatcgc ccaaccgccg gctggcgga                           1239
```

<210> SEQ ID NO 69
<211> LENGTH: 294
<212> TYPE: DNA
<213> ORGANISM: Mycobacteria tuburculosis -continued

<400> SEQUENCE: 69
atgacctcgc gttttatgac ggatccgcac gcgatgcggg acatggcggg ccgttttgag 60
gtgcacgccc agacggtgga ggacgaggct cgccggatgt gggcgtccgc gcaaaacatt 120
tccggcgcgg gctggagtgg catggccgag gcgacctcgc tagacaccat gacccagatg 180
aatcaggcgt ttcgcaacat cgtgaacatg ctgcacgggg tgcgtgacgg gctggttcgc 240
gacgccaaca actacgaaca gcaagagcag gcctcccagc agatcctcag cagc 294

<210> SEQ ID NO 70
<211> LENGTH: 282
<212> TYPE: DNA
<213> ORGANISM: Mycobacteria tuburculosis

<400> SEQUENCE: 70
atgaccatca actatcaatt cggggacgtc gacgctcacg gcgccatgat ccgcgctcag 60
gccgggtcgc tggaggccga gcatcaggcc atcatttctg atgtgttgac cgcgagtgac 120
ttttggggcg gcgccggttc ggcggcctgc caggggttca ttacccagct gggccgtaac 180
ttccaggtga tctacgagca ggccaacgcc cacgggcaga aggtgcaggc tgccggcaac 240
aacatggcac aaaccgacag cgccgtcggc tccagctggg cc 282

<210> SEQ ID NO 71
<211> LENGTH: 1185
<212> TYPE: DNA
<213> ORGANISM: Mycobacteria tuburculosis

<400> SEQUENCE: 71
atgaaggcac cgttgcgttt tggcgttttc atcacgccat tccatccgac cggtcaatcc 60
ccgaccgtgg cgttgcaata cgacatggag cgcgtcgttg cgctggaccg gctcggctac 120
gacgaggcgt ggtttggcga acaccactcc ggtggctacg agctgatcgc ttgcccggag 180
gtgtttatcg cggccgcagc ggaacggacc acccacatcc ggctaggtac cggagtggtt 240
tcgctgccct accatcatcc gctaatggtg gccgaccgtt gggtgctgct ggatcacctg 300
acccgtgggc gggtcatgtt cggcaccggc cccggcgcgc tgccgtcgga cgcctacatg 360
atgggcatcg atccggtcga gcagcgacga atgatgcagg agtccctcga ggcgattctc 420
gcgctgttcc gtgccgcacc tgacgagcga atcgaccgcc actccgactg gttcaccctg 480
cgtgaagcgc aattgcacat ccgcccctac acctggccgt accccgaaat cgctaccgca 540
gccatgattt cgccatcggg tccgcgactg gccggtgcgc tgggcacgtc gctgttatca 600
ctgtcgatgt cagtgcccgg cggctacgct gcgctggaaa cagcgtgggg cgtggtgcgg 660
gagcaggccg ccaaagctgg gcggggcgag ccggatcgcg ccgattggcg ggtgttgagc 720
atcatgcact tgtcggacag ccgcgaccag gcgatcgacg actgcactta cgggttaccc 780
gacttctcga ggtacttcgg cgcggcaggg tttgtcccgt tggcgaacac cgtggaaggc 840
acccagtcgt ctcgggaatt cgtcgagcaa tacgcggcca agggaaattg ctgcatcggc 900
acgcccgatg acgcgatcgc ccacattgaa gacttgctgc accggtcggg tggcttcgga 960
acgttgctac tgctcggcca cgactgggcc ccgccaccgg caacctttca ctcctatgag 1020
ctgttcgccc gtgctgtgat tccttatttc aagggacaac tcgcggcgcc gcgggcgtcg 1080
cacgaatggg ctagaggcaa gcgcgaccaa ttgattggcc gcgccggcga agcggtcgtc 1140
aaagccatca ccgagcacgt cgccgaacaa ggggaagcgg gcagc 1185

-continued

<210> SEQ ID NO 72
<211> LENGTH: 966
<212> TYPE: DNA
<213> ORGANISM: M. tuberculosis

<400> SEQUENCE: 72
atgggcgcac ctaccgaacg gttagttgat accaacggcg tgcgactgcg agtggtcgag 60
gccggtgagc ccggcgcacc cgtggtgata ctggcccacg gctttcccga actggcctat 120
tcatggagac accagattcc tgcgcttgcc gacgccggct accacgtgtt ggctcccgat 180
cagcgcggtt acggcggatc gtctcgccca gaggcgatcg aggcctacga cattcaccgg 240
ttgaccgctg acctagtggg cctactagat gatgtcggtg ccgagcgggc ggtctgggtt 300
ggtcatgact ggggtgccgt ggtggtgtgg aacgcgccac tgctgcacgc tgaccgagtc 360
gccgccgttg ccgcgttgag cgtccccgcg ctgccccggg cacaggtgcc gccgacgcaa 420
gcgttccgca gcaggtttgg ggagaacttc ttctacatcc tttatttcca ggagcccggc 480
atcgccgacg ccgaactcaa tggcgacccg gcccgcacga tgcgccgaat gatcggcggt 540
ctgcgccctc cgggcgatca gagcgcggca atgcgtatgc tggcgcccgg ccccgacggc 600
tttatcgatc ggcttccgga gccggccggg ttgccggcct ggattagtca ggaggaactc 660
gaccactaca tcggcgagtt cacccgcacc ggtttcaccg gcggcctgaa ctggtaccgc 720
aacttcgacc gcaactggga gaccacggcc gacctcgccg gcaagacgat ctccgtgccc 780
tcgttgttca ttgcgggcac agccgatccc gtcttgacgt tcacccgcac cgaccgcgct 840
gcggaggtga tctccggccc gtatcgcgag gtgctgatcg acggggcggg tcactggctg 900
cagcaggaac gtcccggtga ggtgaccgcg gccctgctgg agttcctgac ggggttggag 960
ttgcga 966

<210> SEQ ID NO 73
<211> LENGTH: 1365
<212> TYPE: DNA
<213> ORGANISM: Mycobacteria tuburculosis

<400> SEQUENCE: 73
gtgaataccg atgtgctggc tggcctgatg gccgagctgc ccgaggggat ggtggtcacc 60
gaccccgccg tcaccgacgg ctaccggcaa gaccgggcct ttgacccttc ggccggcaaa 120
ccgctggcaa tcatccggcc acggcgcacc gaagaggtgc agacggtgct gcgttgggcc 180
agtgcgaacc aggtgcccgt ggtgacccga ggagccggta gcggcctttc gggcggggcg 240
accgccctgg atggcgggat cgtgctgtcc accgaaaaga tgcgcgacat caccgtcgac 300
ccggtcaccc gcaccgcagt gtgccagccc ggcctgtaca acgccgaggt gaaggaggcc 360
gccgccgaac acggcctgtg gtatcccccg gatccgtcgt cgttcgagat ctgcagcatc 420
ggcggcaaca tcgccaccaa cgccggcggg ctgtgctgcg tgaagtacgg cgtcacaggc 480
gactacgtac tgggcatgca ggttgtgctg gccaacggca ccgcggtccg gctgggcggc 540
ccacggctca aggacgtcgc cgggctttcc ctgaccaaac tgttcgtcgg cagcgaaggc 600
acgctgggcg tcatcacgga ggtgacgttg cgactgctgc ccgcacagaa tgcatcgagc 660
atcgtggtgg ccagcttcgg ctcggtgcag gcggcggtcg atgcggtgct cggggttacc 720
ggccgacttc gccccgcgat gctggagttc atggattcgg tggcgatcaa cgccgtcgag 780
gacaccttgc ggatggacct ggaccgcgat gcggcggcca tgctggtggc tggttctgat 840
gaacgtggcc gcgcggccac cgaagacgcc gccgtgatgg ccgccgtgtt cgccgaaaac 900

-continued

```
ggtgcgatag acgtgttttc gaccgacgac ccggatgagg gcgaggcgtt cattgcggcc    960

cggcggttcg ccattccggc ggtcgagagc aagggggcgt tgctgctcga ggacgtcggg   1020

gtaccgctgc ccgcactggg cgaactggtc accgggattg cgcgcatcgc cgaggagcgg   1080

aatctgatga tctcggtgat cgcccacgcc ggggacggca atacccaccc gttgctggtg   1140

tacgaccccg cagatgccgc gatgctagag cgcgcccacc tcgcgtacgg cgaaatcatg   1200

gacctggccg tcggcctggg cggcacgatc accggcgaac acggcgtggg ccggttgaaa   1260

cggccgtggt tggccggcta tctcgggccc gacgtcctgg ccctcaacca gcgcatcaag   1320

caagcgctgg acccccaggg catcctcaat cccggctcgg cgatc                   1365
```

```
<210> SEQ ID NO 74
<211> LENGTH: 1215
<212> TYPE: DNA
<213> ORGANISM: Mycobacteria tuburculosis

<400> SEQUENCE: 74

atgacatcag taatgtctca cgaattccag ctcgccaccg ccgaaacctg gccgaatccg     60

tggccgatgt accgcgcgtt gcgcgaccac gacccggtgc accacgtcgt cccgccgcag    120

cgtcccgagt acgactacta cgtgctgtcc cggcacgccg acgtctggtc ggcagcgcgg    180

gaccatcaga cgttctcgtc ggcgcaaggc ttgaccgtta actacggcga gctggaaatg    240

attggactgc acgacacccc gcccatggtg atgcaggatc cgccggtcca caccgagttt    300

cgcaagctgg tgtcgcgcgg cttcacgcca cgacaggtcg aaaccgtcga gcccacggtg    360

cgcaagttcg tcgttgagcg gctcgaaaag ctgcgcgcca acggtggcgg cgacattgtc    420

accgaactat tcaaaccgct cccgtcgatg gtggtggcgc actatctcgg tgttcccgaa    480

gaggattgga cgcaattcga cgggtggacc caggccatcg tggcggcgaa cgcggttgac    540

ggcgccacca ccggcgcact ggacgcggtc ggctcgatga tggcctactt caccgggctg    600

atcgagcgac gccgcaccga gcccgccgac gacgccatct cccacctggt agccgccggg    660

gtcggcgccg acggcgacac cgccggcaca ctgtccatac tggcgttcac gttcaccatg    720

gtcaccggcg gcaacgacac cgtcaccggc atgctaggcg gttcgatgcc gttgctgcac    780

cggcggcccg accagcgccg gctgctgctg gatgacccag agggcatccc cgacgcggtc    840

gaggagctgc tgcggctcac ctcgccggtg caggggctgg cgcgcacaac cacgcgcgac    900

gtcacgatcg gtgacaccac catcccggcc ggtcgccggg tgctgctgct gtacggctcg    960

gccaaccgtg acgaacgcca atacggcccg gacgcagccg aactcgatgt cactcggtgc   1020

ccgcgcaaca tcttgacctt cagccacggc gcccaccact gcctgggtgc ggccgcggcc   1080

cggatgcaat gccgggtggc gctgaccgaa ctgctggccc ggtgcccgga cttcgaggtg   1140

gccgagtcac gcatcgtgtg gtccggcggc agttatgtcc ggcgtccgct gtcggtgccg   1200

ttccgagtga catcc                                                    1215
```

```
<210> SEQ ID NO 75
<211> LENGTH: 606
<212> TYPE: DNA
<213> ORGANISM: Mycobacteria tuburculosis

<400> SEQUENCE: 75

atggcgggta ccgactggct gtccgcgcgt cggaccgagt tagccgcaga tcggatactc     60

gacgccgccg agcgactctt tacgcagcgt gacccggcgt cgatcggcat gaacgagatc    120
```

-continued

```
gccaaggccg caggctgttc gcgcgcaaca ctgtatcggt acttcgacag ccgcgaggcg    180
ctgcgaaccg cgtacgtgca ccgcgagacc cgccggctcg gccgcgagat catggtgaag    240
atcgccgatg tcgtcgaacc tgccgaacgg ctgctggtga gcatcaccac gacgttgcgg    300
atggtccgcg acaaccccgc gttggccgcg tggtttacca ccacccgccc accgatcggc    360
ggcgagatgg ccggacggtc cgaggtgatc gcggccctgg ccgcggcatt cctcaactca    420
ctaggtcccg acgatccgac caccgtcgaa cgccgcgccc gctgggtggt ccggatgctc    480
acatcgctgc tgatgttccc cggccgtgac gaagccgacg aacgagcgat gatcgcggag    540
ttcgtcgtcc cgatcgtgac acctgcttct gccgccgcta ggaaggccgg tcaccctgga    600
cccgag                                                               606
```

<210> SEQ ID NO 76
<211> LENGTH: 534
<212> TYPE: DNA
<213> ORGANISM: Mycobacteria tuburculosis

<400> SEQUENCE: 76

```
atgcatccaa tgataccagc ggagtatatc tccaacataa tatatgaagg tccgggtgct     60
gactcattgt ctgccgccgc cgagcaattg cgactaatgt ataactcagc taacatgacg    120
gctaagtcgc tcaccgacag gctcggcgag ctgcaggaga actggaaagg tagttcgtcg    180
gacttgatgg ccgacgcggc tgggcggtat ctcgactggc tgactaaaca ctctcgtcaa    240
attctggaaa ccgcctacgt gatcgacttc ctcgcatacg tctatgagga gacacgtcac    300
aaggtggtac ccccggcgac tatcgccaac aaccgcgagg aggtgcacag gctgatcgcg    360
agcaacgtgg ccggggtaaa cactccagca atcgcaggac tcgatgcaca atatcagcag    420
taccgggccc aaaatatcgc tgtcatgaac gactatcaaa gtaccgcccg gtttatccta    480
gcgtatctgc cccgatggca ggagccgccg cagatctacg gggcgggggg cggg          534
```

<210> SEQ ID NO 77
<211> LENGTH: 1230
<212> TYPE: DNA
<213> ORGANISM: Mycobacteria tuburculosis

<400> SEQUENCE: 77

```
gtggccacga tagcccaacg gctgcgtgac gaccacgggg tggcggcgtc ggagtcgtcg     60
gtgaggcgtt ggatcgcaac gcatttcgcc gaggaggtgg cccgcgagag agtcacggtg    120
ccgcgcggac cggtcgatgc gggtagtgag gcgcagatcg attacgggcg gctgggcatg    180
tggttcgacc cggccaccgc gcgccgggtc gcggtgtggg cgttcgtgat ggtgctggcg    240
ttctcccgac acctgttcgt gcgtccggtc atccggatgg accaaaccgc ttggtgtgct    300
tgccatgtcg ccgcattcga attcttcgac ggggtgccgg cgcggctagt gtgtgacaac    360
ctcaggaccg gggtggacaa gcccgacctg tacgacccgc agatcaaccg ctcctacgcc    420
gagctggcca gccactacgc cacgctggtc gacccggccc gcgccagaaa acccaaagat    480
aaaccccgcg tggagcggcc gatgacctat gtgcgggact cgttttggaa aggccgcgag    540
ttcgattcgc tggcccagat gcagcaggcg gcggtcacct ggagcaccga agtggccggg    600
cttcggtact tacgtgcctt ggagggcgcc caacccctgc ggatgttcga agctgtggag    660
caacaagcgt tgatcgcatt gccgcccagg gcatttgaac tcaccagctg gtcgatcggc    720
accgtcgggg tggacacgca cctcaaagtt ggcaaggcac tctattccgt gccgtggcgg    780
ctgatcgggc aacgcctgca cgcgcgcacc gccggtgatg tggtgcagat cttcgccggc    840
```

-continued aacgatgtgg tggccaccca tgtgcgccga cccagcgggc gctccaccga cttctcccac 900
tacccaccgg agaagatcgc cttccacatg cgcaccccga cctggtgtcg acacaccgcc 960
gaactggtcg gcccagccag ccagcaagtg atcgccgaat tcatgcgcga caacgccatc 1020
caccacctac ggtcggccca aggcgtgctc gggctacgcg acaaacacgg ctgcgaccgg 1080
ctggaggccg cctgcgcccg cgccatcgag gtcggcgacc cgagctatcg caccatcaag 1140
ggcatccttg ttgccggcac cgaacacgcc gccaacgagc cgaccaccag tagtccggca 1200
agcaccgctg gggcgttcc tgcgcggccc 1230

<210> SEQ ID NO 78
<211> LENGTH: 753
<212> TYPE: DNA
<213> ORGANISM: Mycobacteria tuberulosis

<400> SEQUENCE: 78
atgtctatct gtgatccggc gctgcgtaat gcgctacgta ccctgaaact gtccggcatg 60
ctcgacaccc tcgacgcccg cctggcccaa acccgcaacg gcgacctggg gcatctggaa 120
ttcctgcaag cgttgcgtga agacgagatc gcccgccgcg agtccgccgc cctgacacga 180
cgattacgcc gcgccaagtt cgaagcccaa gccaccttcg aagacttcga cttcactgcc 240
aacccgaaac tgcccggtgc gatgttgcgc gatctggccg cgctgcgctg gctggatgcc 300
ggcgaatcgg tcatcctcca cggcccggtc ggcgtcggaa aaacccatgt agcacaagca 360
cttgtccacg ccgtggcccg ccgcggcggc gacgtgcgct tcgccaaaac ctcccgcatg 420
ctctccgacc tcgccggcgg gcacgccgac cgatcctggg gccaacgcat ccgcgaatac 480
accaagccgc tcgtgctcat tctggacgac ttcgcgatgc gtgagcacac cgccatgcac 540
gctgatgacc tctacgagct catcagcgac cgcgccatca ctggcaaacc gctgatcttg 600
accagcaacc gcgcaccgaa taactggtac ggcctgttcc ccaaccccgt cgtcgccgaa 660
tcactcctgg atcggctcat caacaccagc caccaaatcc tcatggacgg acccagctac 720
cgaccccgca agagacccgg ccgcaccacc agc 753

<210> SEQ ID NO 79
<211> LENGTH: 696
<212> TYPE: DNA
<213> ORGANISM: Mycobacteria tuberulosis

<400> SEQUENCE: 79
atgcatctaa tgatacccgc ggagtatatc tccaacgtaa tatatgaagg tccgcgtgct 60
gactcattgt atgccgccga ccagcgattg cgacaattag ctgactcagt tagaacgact 120
gccgagtcgc tcaacaccac gctcgacgag ctgcacgaga actggaaagg tagttcatcg 180
gaatggatgg ccgacgcggc tttgcggtat ctcgactggc tgtctaaaca ctcccgtcag 240
attttgcgaa ccgcccgcgt gatcgaatcc ctcgtaatgg cctatgagga gacacttctg 300
agggtggtac ccccggcgac tatcgccaac aaccgcgagg aggtgcgcag gctgatcgcg 360
agcaacgtgg ccgggggtaa acactccagc aatcgcagac ctcgaggcac aatacgagca 420
gtaccgggcc gaaaatatcc aagcaatgga ccgctatcta agttggaccc gatttgcgct 480
atcgaagctg ccccgatggc gggagccgcc gcagatccac aggagcgggt aggtccaaga 540
ggccggcgcg gtcttgcagg ccagcaacaa tgccgcggtc gaccaggccc atcgcttcgc 600
tgctcgcacg acacaccgcg gtttcagatg aatcaggcgt ttcacaccat ggtgaacatg 660

-continued

```
ttgctgacgt gttttgcatg tcaggagaaa ccgaga                              696


<210> SEQ ID NO 80
<211> LENGTH: 528
<212> TYPE: DNA
<213> ORGANISM: Mycobacteria tuberulosis

<400> SEQUENCE: 80

atgcatccaa tgataccagc ggagtatatc tccaacataa tatatgaagg cccgggcgct     60

gactcattgt ttttcgcctc cgggcaattg cgagaattgg cttactcagt tgaaacgacg    120

gctgagtcgc tcgaggacga gctcgacgag ctggatgaga actggaaagg tagttcgtcg    180

gacttgttgg ccgacgcggt tgagcggtat ctccaatggc tgtctaaaca ctccagtcag    240

cttaagcatg ccgcctgggt gatcaacggc ctcgcgaacg cctataacga cacacgtcgg    300

aaggtggtac ccccggagga gatcgccgcc aaccgcgagg agaggcgcag gctgatcgcg    360

agcaacgtgg ccggggtaaa cactccagca atcgcagacc tcgatgcaca atacgaccag    420

taccgggccc gcaatgtcgc tgtaatgaac gcctatgtaa gttggacccg atctgcgcta    480

tcggatctgc cccggtggcg ggaaccgccg cagatctaca ggggcggg                 528


<210> SEQ ID NO 81
<211> LENGTH: 1170
<212> TYPE: DNA
<213> ORGANISM: M. tuberculosis

<400> SEQUENCE: 81

atgatcatcg ttgtcgggat cggcgccgac ggcatgaccg gtctctccga gcattctcgc     60

tccgaattgc gcagggccac agtaatttac ggctcgaaac ggcaacttgc cctgctcgac    120

gataccgtca ccgccgagcg ctgggagtgg ccgacgccga tgctgcccgc ggtgcaaggc    180

ctgtcaccgg atggggctga cctacacgtg gttgccagcg gcgacccgtt gttgcatggt    240

atcggctcca ccctgatccg gctgttcggc cacgacaacg tgaccgtgtt gccgcacgtg    300

tccgcggtga cgttggcgtg cgcccggatg ggctggaacg tgtatgacac cgaggtgatc    360

agcctggtca ccgcgcaacc acacaccgcg gtgcgccgcg gcggccgggc catcgtgctg    420

tccggcgatc ggtccacccc gcaggcgctg gcggtgctgc tgaccgagca cggtcgcggt    480

gactccaagt tcagcgtgct cgaacagctt ggcggcccgg ccgaacgccg ccgcgacggt    540

acggcccggg catgggcctg cgacccaccc ctcgatgtcg atgagctcaa cgtgatcgcc    600

gtgcgctacc tgctcgacga gcgcacgtcg tgggcacccg acgaggcatt cgcgcacgac    660

gggcagatca ccaaacaccc gatccgcgtg ctgaccctgg ctgcgctggc gccaaggccc    720

gggcagcggt tatgggacgt cggcgcgggc tcaggcgcca tcgcggtcca gtggtgtcgg    780

agctggccgg gctgcaccgc ggtggcgttc gagcgcgacg aacggcgccg ccgcaacatt    840

gggttcaatg ccgcggcctt cggggtgagc gtcgacgtgc gcggcgacgc gcccgatgcg    900

ttcgacgacg ccgcacggcc gtcggtgatt tttcttggcg gtggtgtaac ccagccaggc    960

ctgcttgagg cctgcctgga cagcctgccc gcaggcggga acttggtcgc caacgctgtc   1020

accgtcgaat cggaagccgc tctggcgcat gcatattcgc gcctcggtgg cgagctacga   1080

cgattccagc actatctcgg cgaaccgctg ggcggcttca ccggttggcg cccacagctg   1140

ccggtcaccc agtggtcggt gaccaagcga                                    1170


<210> SEQ ID NO 82
<211> LENGTH: 747
```

-continued

<212> TYPE: DNA
<213> ORGANISM: Mycobacteria tuberulosis

<400> SEQUENCE: 82
gtggacgaca cgggcgctgc tccggtagta attttcggcg gccgcagcca gatcggcggc 60
gaactcgcgc gacgcctggc tgccggggcg acgatggtgc tggccgcgcg gaacgccgat 120
caactcgccg accaggccgc cgcactccgc gcagctggcg ctatagcggt gcacacccgg 180
gagttcgacg ccgacgacct ggccgcacac ggcccgttgg tcgcttcgct cgttgccgag 240
cacggcccca tcggcaccgc ggtgctggcc ttcgggatac tcggcgacca ggcccgcgcc 300
gagacagacg cggcgcacgc ggtggccatc gtgcacaccg actacgtcgc ccaggtcagc 360
ctgctgactc atctggcagc ggcgatgcgc accgccggac ggggatcgct ggtggtgttc 420
tcctcggtcg ccgggattcg ggtgcgccgc gccaactatg tctacggatc ggccaaagcc 480
ggcctggacg gcttcgccag cggcctggcc gatgcgttgc acggcaccgg ggtgcggtta 540
ctgatcgcgc ggccgggatt cgtcatcggg cgcatgaccg agggcatgac gcccgcaccc 600
ctgtcggtca ccccggagcg ggtggccgcc gcgaccgcgc gtgcgctggt caacggtaag 660
cgcgtggtgt ggattccgtg ggcgctgcgg ccaatgtttg ttgcgctgcg gttgcttccc 720
cggttcgtct ggcgcaggat gccgcga 747

<210> SEQ ID NO 83
<211> LENGTH: 411
<212> TYPE: DNA
<213> ORGANISM: Mycobacteria tuberulosis
<400> SEQUENCE: 83
gtggcgatgg tcaacaccac tacgcggctt agtgacgacg cgctggcgtt tctttccgaa 60
cgccatctgg ccatgctgac cacgctgcgg gcggacaact cgccgcacgt ggtggcggta 120
ggtttcacct tcgaccccaa gactcacatc gcgcgggtca tcaccaccgg cggctcccaa 180
aaggccgtca atgccgaccg cagtgggctt gccgtgctca gccaggtcga cggcgcgcgc 240
tggctctcac tggagggtag ggcggcggtg aacagcgaca tcgacgccgt gcgcgacgcc 300
gagctgcgct acgcgcagcg ctatcgcacc ccgcgtccca atccacgccg agtggtcatc 360
gaggtccaga ttgagcgcgt gctgggatcc gcggatctgc tcgaccgggc c 411

<210> SEQ ID NO 84
<211> LENGTH: 1461
<212> TYPE: DNA
<213> ORGANISM: Mycobacteria tuberulosis
<400> SEQUENCE: 84
atgccccgcg cccgatggct gcagagcgcg gccctcatgg gcgccttggc cgtggtgttg 60
ataaccgcgg caccggtggc cgccgatgcc taccaggtgc ccgctccgcc ctcgcccacc 120
gcatcctgtg acgtaataag cccggttgcg atcccctgcg tggcgctcgg caagttcgcc 180
gacgcggtcg ctgcggagtg tcgccgcgtc ggtgtgcccg atgcgcggtg cgtgcttccg 240
ctcgcgcacc gggtgaccca ggccgcgcgt gatgcctacc tacagtcttg ggtgcatcgc 300
accgcgcggt tccaggatgc gttgcaagac ccggtgccgc tgcgggaaac tcagtggctc 360
ggcacgcaca actcgttcaa cagcctcagc gattcgttca cggtctcgca cgcagactca 420
aaccagcagc tgtcgttggc ccaacagctc gacatcgacg tccgcgcgct cgagctagac 480
ctgcactact tgccccgcct cgagggccac ggcgcccccg gcgtcaccgt gtgtcacggg 540

-continued

```
ctgggaccga agaacgcgaa cctaggctgc accgtcgaac ctctgctggc cacagtgctg    600

ccgcagatcg ccaactggtt gaacgcaccc gggcataccg aggaggtcat cctgctctac    660

ctggaggacc agctgaagaa cgcgtcggcg tatgagtcgg tggtggctac cctcgaccaa    720

gtgttgcggc gtgcggacgg aacaagcctt atctaccgtc ccaacccggc ccggcgtgcc    780

accaacggct gtgtcccgct tccactcgac gtgtcgcggg aggaaatccg cgcatccggc    840

gcacgagccg tgctcgtcgg gtcttgtgcg ccaggttggt cggccgccgt cttcgactgg    900

agcggcgttg agctggaaag cggctcgaac tccggctacc ggccataccc ggcctgcgat    960

gccacctatg gccgcggtgt ctacgcttgg cgactggtcc gctattacga ggactccacg   1020

ctggccacgg cgttggccaa cccgacccgt ccaccggcca atccgcaggc gcttaccccg   1080

ccgaaggtgc cggcgatgac cgattgcggg gtcaatctgt tcggcttcga tcagctgctc   1140

cccgaagacg gccgcattca ggcgtcgttg tggagctggg caccggacga accgcgtgcc   1200

ggtgccggag catgcgccct gcagggcgcg gatggccgct gggtcgccgc atcgtgcggt   1260

gacccacacc ctgcggcctg tcgggacgcg gcaggcaggt ggaccgtgac gccggcaccc   1320

gtggtcttcg ccggggctgc cctagcctgc acagccatcg gcgcggactt taccctgccc   1380

cgaacgggca atcagaacgc ccgtctgcac gccgtggccg ggcccgccgg tggcgcctgg   1440

gtgcattacc tactgccgcc a                                             1461
```

<210> SEQ ID NO 85
<211> LENGTH: 429
<212> TYPE: DNA
<213> ORGANISM: Mycobacteria tuberulosis

<400> SEQUENCE: 85

```
atgaccacca cgccccgaca acccctgttc tgcgcccacg ccgacaccaa cggcgacccg     60

ggccgctgcg cctgcggcca gcagctcgcc gacgtcggcc cggccacccc gccaccgccc    120

tggtgcgaac cgggcaccga acccatctgg gagcagctca ccgaacgata cggcggcgtc    180

acaatctgcc agtggacacg atattttccg gccggcgacc cggtggctgc cgacgtgtgg    240

atcgccgccg acgatcgtgt cgttgacggc cgggtgctgc gcacccaacc ggcgattcac    300

tacacggaac cgcccgtgtt ggggatcggc ccggcggcgg cccgccggct ggccgctgag    360

ctgctcaacg ccgccgacac cctcgacgac ggccgccggc agctagacga cctcggcgaa    420

caccggcgg                                                            429
```

<210> SEQ ID NO 86
<211> LENGTH: 996
<212> TYPE: DNA
<213> ORGANISM: Mycobacteria tuberulosis

<400> SEQUENCE: 86

```
gtgaacaccg cgacccgggt ccggctggcc cgcaaacgcg ccgaccggct caatctgaaa     60

ctaatcaaga acggccacca cttcaggttg cgtgacgccg acgagatcac gctggcggtc    120

gggcacctag gggtggtgga agccttcctg gcggcggcca agtcgcaaaa caagccgccc    180

ggtccgccgc cgagcctcca cgccccgcca tcctggcggc gcgacatcga cgactacctg    240

ctcaacctga acgccgccgg tcaacgccca gcgacgatcc ggctacgcaa gacggtgctg    300

tgcgcagccg cccacggcct cggccgccca cccgccgacg tcaccgccga acacctcctg    360

gactggctag gcaaacagca gcacctctcc ccagagggcc gcaaaaccta tcgcagcacg    420

ttgcggggct tcttcgtgtg ggcctacgaa atggaccggg tgcgcgacta tgtcgcagac    480
```

-continued

```
tccctgccta aggtgcgctg cccgaaacag ccgccccgcc cggccggcga cgacgtctgg    540

caagcggcgc tggccaaggc cgaccgtcga atcgagctga tgatccgcct agccggtgag    600

gccgggctgc gacgcgccga agccgcccag gcgcacaccg gcgacttgat ggacggcggg    660

cttctcctcg ttcacggcaa aggtggtaaa cgccgtattg tgccgatcag cgactacttg    720

gccgcgctca tccgcgacac cccgcacggc tacctgttcc ccaacggcac cggcggccac    780

ctcaccgccg aacacgtggg aaaactcgtc tcccgggcat tacccggtga cgcgaccatg    840

cacaccctgc ggcaccgata cgccacccgc gcctaccgcg gctcccacaa cttgcgagct    900

gtacaacaac ttctcggtca cgcctcgatc gtgacaacag aacgctacac agcgctgtgc    960

gacgacgagg tgcgcgccgc agcagcagcc gcatgg                              996
```

<210> SEQ ID NO 87
<211> LENGTH: 366
<212> TYPE: DNA
<213> ORGANISM: Mycobacteria tuberulosis

<400> SEQUENCE: 87

```
gtgcacgtgt gccacacgat cgccgacgtg gtcgaccggg ccaaagccga acgctccgaa     60

aacacgcttc gcaaggattt cacccccctcg gagctgctcg ccgctggtcg ccggatcgcc    120

gagctggaac ggccgaaagc caaacagcgg caacgcgaag gcggcgacca tggccgccag    180

gctcgatatt ctggcttagg ctccatggag cctaagccag aatcagagcg cgatgcccac    240

aaagccgaca ctgccatcag cgaagccctc ggcatctccc gcggccacta ccagcggctc    300

aaacgaatcg acaacgcaac ccgcagcgaa gctggctacc gggatggttt aaacggttgg    360

agcggc                                                               366
```

<210> SEQ ID NO 88
<211> LENGTH: 324
<212> TYPE: DNA
<213> ORGANISM: Mycobacteria tuberulosis

<400> SEQUENCE: 88

```
atgtcaggtg gttcatcgag gaggtacccg ccggagctgc gtgagcgggc ggtgcggatg     60

gtcgcagaga tccgcggtca gcacgattcg gagtgggcag cgatcagtga ggtcgcccgt    120

ctacttggtg ttggctgcgc ggagacggtg cgtaagtggg tgcgccaggc gcaggtcgat    180

gccggcgcac ggcccgggac cacgaccgaa gaatccgctg agctgaagcg cttgcggcgg    240

gacaacgccg aattgcgaag ggcgaacgcg attttaaaga ccgcgtcggc tttcttcgcg    300

gccgagctcg accggccagc acgc                                           324
```

<210> SEQ ID NO 89
<211> LENGTH: 984
<212> TYPE: DNA
<213> ORGANISM: Mycobacteria tuberulosis

<400> SEQUENCE: 89

```
aaagaccgcg tcggctttct tcgcggccga gctcgaccgg ccagcacgct aattacccgg     60

ttcatcgccg atcatcaggg ccaccgcgag ggccccgatg gtttgcggtg gggtgtcgag    120

tcgatctgca cacagctgac cgagctgggt gtgccgatcg ccccatcgac ctactacgac    180

cacatcaacc gggagcccag ccgccgcgag ctgcgcgatg gcgaactcaa ggagcacatc    240

agccgcgtcc acgccgccaa ctacggtgtt tacggtgccc gcaaagtgtg gctaaccctg    300
```

-continued

```
aaccgtgagg gcatcgaggt ggccagatgc accgtcgaac ggctgatgac caaactcggc    360

ctgtccggga ccacccgcgg caaagcccgc aggaccacga tcgctgatcc ggccacagcc    420

cgtcccgccg atctcgtcca gcgccgcttc ggaccaccag cacctaaccg gctgtgggta    480

gcagacctca cctatgtgtc gacctgggca gggttcgcct acgtggcctt tgtcaccgac    540

gcctacgctc gcaggatcct gggctggcgg gtcgcttcca cgatggccac ctccatggtc    600

ctcgacgcga tcgagcaagc catctggacc cgccaacaag aaggcgtact cgacctgaaa    660

gacgttatcc accatacgga taggggatct cagtacacat cgatccggtt cagcgagcgg    720

ctcgccgagg caggcatcca accgtcggtc ggagcggtcg gaagctccta tgacaatgca    780

ctagccgaga cgatcaacgg cctatacaag accgagctga tcaaacccgg caagccctgg    840

cggtccatcg aggatgtcga gttggccacc gcgcgctggg tcgactggtt caaccatcgc    900

cgcctctacc agtactgcgg cgacgtcccg ccggtcgaac tcgaggctgc ctactacgct    960

caacgccaga gaccagccgc cggc                                            984
```

<210> SEQ ID NO 90
<211> LENGTH: 1437
<212> TYPE: DNA
<213> ORGANISM: Mycobacteria tuberulosis

<400> SEQUENCE: 90

```
atgactaatg aacaacattt cgctgacgat ggcgacatca aacagctcag cctcgacgaa     60

acccgttccg cggcaaaaca gctcctcgac tccgtcgagg gcgacctgac cggtgatgtg    120

gcgcaacgtt ttcaggcgct gacacgccac gccgaggaac tgcgggcgga gcagcgccgc    180

cgcggccgcg aagccgagga ggcgctgcgc cgctgccggg ccggtgagct gagggtggtg    240

cccggtgctc ccaccggcgg cgacgacggc gacgcgccgc cgggcaactc gttgcgcgac    300

atcgcgtttc gcacactgga cgtttgtgtg cgcgatggcc tgatgtcgtc gcgggcggcg    360

gaagccgcgg aaaccttgtg ccgcaccggg ccgccgcagt cgacgtcgtg ggcgcagcgc    420

tggctggcgg ccaccggcaa ccgcgactac ctgggggcgt tcgtcaagag ggtttcgaac    480

cctgttgcgg ggcacacgac ctggaccgac cgggaagcgg ccgcgtggcg tgaggcggcc    540

gcggtggccg ccgagcagcg agcaatgggc ttggtggaca ccgccggcgg gtttttgatc    600

ccggcggcgc tggatccggc gattctgctg tcgggtgatg gttcaacgaa tccgatccgg    660

caggtggcga gggtggtgca aacgacctcc gaggtttggc ggggcgtgac ctccgaaggc    720

gccgaggctc attggtactc cgaagcccag gaggtgtccg acgattcgcc aacgctggcc    780

cagccggcgg tgccgagcta ccgtggctcc tgctggattc cgttcagtct cgagattgag    840

ggtgacgccg ccggattcgt cgcagaggtg ggccgcgtcc tagcggattc ggttgagcag    900

ctgcaggcgg cggcgttcgt cagcggctcc ggcaacggcg agcccaccgg attcgtctcc    960

gcactgaccg gcaccgcgga ctacaccgtc accggcgcgg ggacggaagc cgttgtagcc   1020

gccgacgttt acgcgctgca gtcggcgttg ccgccgcgct ttcaatccaa cagcgcgttc   1080

gcggcgaact tgtccaccat caacgtgctg cgccaggcgg aaaccgcgaa tggggcgctg   1140

aaattcccat cgctgcacgc cagcccgccg atgctggccg ggaaacacat ctgggaggtg   1200

tcgaacatgg acaccgtgga cgcggcggtg accgccacca attacccgct ggtgcttggc   1260

gactggaagc agttcatcat caccgaccgg gtcgggtcga cggtggagct ggtgccgcac   1320

gtgttcggcg gcaaccgccg accgaccgga cagcgcggat tcttctgctg gttccgagtc   1380

ggttctgatg tgctggtgga caatgcgttc cgcgtgctga aggtgcagac caccgcg      1437
```

-continued

<210> SEQ ID NO 91
<211> LENGTH: 531
<212> TYPE: DNA
<213> ORGANISM: Mycobacteria tuberulosis

<400> SEQUENCE: 91
ttgagtagca tccttttccg cacggccgag ctgcggcctg gtgagggccg caccgtgtac 60
ggcgtcatcg tgccttatgg cgaggtgacc accgtccgcg acctcgacgg cgagttccgg 120
gaaatgttcg ctcctggcgc ttttcggcgc tccatcgctg agcgcggcca caaggtgaag 180
ctgctggtct cccacgacgc tcgaacccgc tacccggttg gccgggccgt cgagctgcgt 240
gaggagcctc acggcttgtt cggggcgttc gagcttgcga acaccccgga cggcgacgag 300
gccctggcga atgtgaaagc tggtgtggtg gacgcgtttt cggtgggttt ccggccgatc 360
cgggaccgcc gggaaggga tgtgatcgtg cgggtcgagg cggcgctgtt ggaggtctcc 420
ttgaccggcg ttccggccta tctgggcgcg cagatcgccg gtgtgcgcgc ggaatcgctt 480
gcagtcgttt cccgttcgct agccgaagcc aggttagccc tgatggattg g 531

<210> SEQ ID NO 92
<211> LENGTH: 624
<212> TYPE: DNA
<213> ORGANISM: Mycobacteria tuberculosis

<400> SEQUENCE: 92
ttgccatcgc cagcaaccgc ccgaccggac accgccacgg tgggagagcg tgtgcgcgct 60
caagttttat ggggcgtttt ttggcatcat ggcattcgcg acccgaaacc cggaaagagg 120
agggtggtgt tgaaaatggg taggcgtggt cccgcgccgg cgccggcgca gttgaaactc 180
ctcggcggcc gctcgccggg ccgtgattct ggcggccggc gggttacacc accggcggcg 240
ttcgagcgtg ttgcgccgga atgcccggat tggttgccgc caggcgctaa agacatgtgg 300
gggcgcgtcg ttcccgagct tgcggcatta aacctgctga aggagtccga ccttggggtg 360
ctgacctcct tctgcgtcgc ctgggatcag ctcatgcagg ctgtaacagc ctaccgtgaa 420
cagggtttca tcgcgacgaa cgcccgcagc cgacgggtga cggtgcatcc tgccgtggcc 480
gcggcccggg ccgcgacgag ggacgttttg gtgctcgcgc gcgaattggg gtgcacgcca 540
agcgctgagg cgaatttggc tgctgtgctg gcggcggcgg gggaccccga cgacgacgag 600
ttcaacccgt tcgccccaga ccgg 624

<210> SEQ ID NO 93
<211> LENGTH: 321
<212> TYPE: DNA
<213> ORGANISM: Mycobacteria tuberculosis

<400> SEQUENCE: 93
ttgacccaca agcgcactaa acgccagcca gccatcgccg cagggctcaa cgccccgcgt 60
cggaatcgcg ttgggcggca acatggttgg ccggccgacg ttccgtccgc cgagcagcgc 120
cgcgcccaac ggcagcgcga cctcgaggct atccgccgag cgtacgccga gatggtggcg 180
acatcacacg aaatcgacga cgacacagcc gaactggcgc tgttgtcgat gcatctcgac 240
gatgagcagc gccggcttga ggcggggatg aagctcggct ggcatccgta tcacttcccc 300
gacgaacccg acagcaaaca g 321

<210> SEQ ID NO 94

-continued

<211> LENGTH: 243
<212> TYPE: DNA
<213> ORGANISM: Mycobacteria tuberculosis

<400> SEQUENCE: 94
atgagcggcc acgcgttggc tgctcggacg ttgctggccg ccgcggacga gcttgtcggc 60
ggcccgccag tcgaggcttc ggccgccgcg ctggccggcg acgccgcggg cgcatggcgg 120
accgcggccg tcgagcttgc gcgagcgttg gtccgcgctg tggcggagtc gcacggcgtc 180
gcggccgttt tgttcgccgc gacggccgcc gcggcggcgg ccgtcgaccg gggtgatccg 240
ccg 243

<210> SEQ ID NO 95
<211> LENGTH: 1425
<212> TYPE: DNA
<213> ORGANISM: Mycobacteria tuberculosis

<400> SEQUENCE: 95
atggctgaca tcccctacgg ccgtgactat cccgacccga tctggtgtga cgaggacggc 60
cagccgatgc cgccggtcgg cgccgaattg ctcgacgaca ttagggcatt cttgcggcgg 120
ttcgtagtct atccaagcga ccatgaactg atcgcgcaca ccctctggat tgcgcattgc 180
tggtttatgg aggcgtggga ctcaacgccc cgaatcgctt ttttgtcacc ggaacccggc 240
tctggcaaga gccgcgcact cgaagtcacg gaaccgctag tgccccggcc ggtgcatgcc 300
atcaactgca caccggccta cctgttccgt cgggtggccg atccggtcgg gcggccgacc 360
gtcctgtacg acgagtgtga caccctgttt ggcccgaaag ctaaagaaca cgaggaaatt 420
cgcggcgtga tcaacgccgg ccaccgcaag ggagccgtcg cgggccgctg cgtcatccgc 480
ggcaagatcg ttgagaccga ggaactgcca gcgtactgtg cggtcgcctt ggccggcctc 540
gacgacctgc ccgacaccat catgtctcgg tcgatcgtgg tgaggatgcg caggagggca 600
ccaaccgaac ccgtggagcc gtggcgcccc cgcgtcaacg gccccgaggc cgagaagctg 660
cacgaccggt tggcgaactg ggcggccgcc attaacccgc tggaaagcgg ttggccggcg 720
atgccggacg gggtgaccga ccggcgcgcc gacgtctggg agtccctggt tgcggttgct 780
gacaccgcgg gcgggcactg gcccaaaacc gcccgtgcaa ccgcagaaac ggatgcaacc 840
gcaaatcgag gagccaagcc cagcataggc gtgctgctgc tgcgggatat ccgtcgagtc 900
ttcagcgacc gggaccggat gcgcaccagc gacatcctga ccggactgaa ccggatggag 960
gagggaccgt ggggctccat ccgccgcggc gacccgctcg acgcgcgcgg cctcgcgacc 1020
cggctcggca gatacggcat cggccgaag ttccagcaca gtggtggcga accaccctac 1080
aaagggtatt cgcggaccca gttcgaggat gcgtggtccc ggtatctctc tgccgacgac 1140 gaaaccccg aggaacgaga tttatcggtt tccgcggttt ccgcggtttc accgccggtt 1200
ggcgatcccg gtgatgcaac cggcgcaacc gatgcaaccg atctcccgga ggcgggcgac 1260
ttgccgtacg agccgccggc gcccaacggg caccccaacg gcgacgcgcc gctgtgctcc 1320
gggccgggat gccccaacaa gctcctcagt actgaggcca aggccgccgg caaatgccgg 1380
ccctgccgag gtcgagcggc ggctagcgct cgggacggcg cccga 1425

<210> SEQ ID NO 96
<211> LENGTH: 390
<212> TYPE: DNA
<213> ORGANISM: Mycobacteria tuberculosis

<400> SEQUENCE: 96

-continued

```
atgaccgccg tcggcgggtc gccgccgacg cgacgatgcc cggccacaga ggaccgggca     60

cccgcgacag tcgccacacc gtctagcacc gatcctaccg cgtcccgcgc cgtgtcgtgg    120

tggtcggtgc acgagtatgt cgcaccgacc ctggccgccg ccgtggaatg gccgatggcc    180

ggcaccccgg cgtggtgcga cctcgacgac accgacccgg tcaaatgggc cgcgatctgc    240

gacgctgctc ggcattgggc actccgggtg gagacgtgcc aggccgcgtc ggccgaggca    300

tcacgtgacg tatccgccgc cgccgactgg ccggcggtct ctcgggagat ccagcgtcgg    360

cgtgacgcct acattcggcg ggtggtggtc                                     390
```

<210> SEQ ID NO 97
<211> LENGTH: 258
<212> TYPE: DNA
<213> ORGANISM: Mycobacteria tuberculosis

<400> SEQUENCE: 97

```
atgtgcgcgt tcccgtcgcc gagtctcggg tggacggtct ctcacgagac cgaaaggccc     60

ggcatggcag acgctccccc gttgtcacgg cggtacatca cgatcagtga ggccgccgaa    120

tatctagcgg tcaccgaccg cacggtccgc cagatgatcg ccgacggccg cctacgcgga    180

taccgctccg gcacccgcct cgtccgtctg cgccgcgatg aggtcgacgg cgccatgcac    240

ccgttcggtg gtgccgca                                                  258
```

<210> SEQ ID NO 98
<211> LENGTH: 360
<212> TYPE: DNA
<213> ORGANISM: Mycobacteria tuberculosis

<400> SEQUENCE: 98

```
atggccgatg cggttaagta cgtagttatg tgcaactgcg acgacgaacc gggagcgctc     60

atcatcgcct ggatcgacga cgaacgaccc gccggcgggc acatacagat gcggtcgaac    120

acccgcttca ccgaaacaca gtggggccgc catatcgagt ggaaactcga atgccgggca    180

tgccgaaagt atgcgccgat atccgagatg accgccgcgg cgatcctcga cggtttcggg    240

gcgaagcttc acgagctgag aacgtcgacc atccccgacg ctgacgatcc atcaatagca    300

gaggcgcgac acgtaattcc gttcagcgca ttatgcttgc gcttgagcca gctaggcggg    360
```

<210> SEQ ID NO 99
<211> LENGTH: 1125
<212> TYPE: DNA
<213> ORGANISM: Mycobacteria tuberculosis

<400> SEQUENCE: 99

```
gtgacgcaaa ccggcaagcg tcagagacgc aaattcggtc gcatccgaca gttcaactcc     60

ggccgctggc aagccagcta caccggcccc gacggccgcg tgtacatcgc cccaaaaacc    120

ttcaacgcca agatcgacgc cgaagcatgg ctcaccgacc gccgccgcga aatcgaccga    180

caactatggt ccccggcatc gggtcaggaa gaccgccccg gagccccatt cggtgagtac    240

gccgaaggat ggctgaagca gcgtggaatc aaggaccgca cccgcgccca ctatcgcaaa    300

ctgctggaca accacatcct ggccaccttc gctgacaccg acctacgcga catcaccccg    360

gccgccgtgc gccgctggta cgccaccacc gccgtgggca caccgaccat gcgggcacac    420

tcctacagct tgctgcgcgc aatcatgcag accgccttgg ccgacgacct gatcgactcc    480

aacccctgcc gcatctcagg cgcgtccacc gcccgccgcg tccacaagat caggcccgcc    540
```

-continued

```
accctcgacg agctggaaac catcaccaaa gccatgcccg acccctacca ggcgttcgtg    600

ctgatggcgg catggctggc catgcgctac ggcgagctga ccgaattacg ccgcaaagac    660

atcgacctgc acggcgaggt tgcgcgggtg cggcgggctg tcgttcgggt gggcgaaggc    720

ttcaaggtga cgacaccgaa aagcgatgcg ggagtgcgcg acataagtat cccgccacat    780

ctgatacccg ccatcgaaga ccaccttcac aaacacgtca accccggccg ggagtccctg    840

ctgttcccat cggtcaacga ccccaaccgt cacctagcac cctcggcgct gtaccgcatg    900

ttctacaagg cccgaaaagc cgccggccga ccagacttac gggtgcacga ccttcgacac    960

tccggcgccg tgttggctgc atccaccggc gccacactgg ccgaactgat gcagcggcta   1020

ggacacagca cagccggcgc cgcactccgc taccagcacg ccgccaaggg ccgggaccgc   1080

gaaatcgccg cactgttaag caaactggcc gagaaccagg agatg                   1125
```

<210> SEQ ID NO 100
<211> LENGTH: 225
<212> TYPE: DNA
<213> ORGANISM: Mycobacteria tuberculosis

<400> SEQUENCE: 100

```
gtgatagcgg gcgtcgacca ggcgcttgca gcaacaggcc aggctagcca gcgggcggca     60

ggcgcatctg gtggggtcac cgtcggtgtc ggcgtgggca cggaacagag gaacctttcg    120

gtggttgcac cgagtcagtt cacatttagt tcacgcagcc cagattttgt ggatgaaacc    180

gcaggtcaat cgtggtgcgc gatactggga ttgaaccagt ttcac                    225
```

<210> SEQ ID NO 101
<211> LENGTH: 186
<212> TYPE: DNA
<213> ORGANISM: Mycobacteria tuberculosis

<400> SEQUENCE: 101

```
atgatcgagc agggccgcga ctgccgggac gtggtcaccc agctcgccgc ggtatcgcgc     60

gcactcgacc gcgccggatt caagatcgtt gcggcagggt tgaaggaatg cgtgtccggg    120

gccacggcca gcggcgcggc accgctgagt gcagctgagc tagaaaagct gttcctggcg    180

ctcgct                                                               186
```

<210> SEQ ID NO 102
<211> LENGTH: 357
<212> TYPE: DNA
<213> ORGANISM: Mycobacteria tuberculosis

<400> SEQUENCE: 102

```
atgtcggacc agccacgtca tcaccaggtc ctcgacgacc tgctgcccca acaccgcgct     60

ctacgtcacc agattcccca ggtgtaccag cgatttgtag ccctgggcga cgccgcgctt    120

accgacggcg ctctcagccg caaggtcaag gagcttgtgg cgctggcgat cgcggttgtg    180

caggggtgcg atggctgcgt cgcatcacac gcccaagccg cggtacgggc cggcgctaca    240

gcgcaagaag ccgctgaggc catcggggtc accatcttga tgcacggtgg accggccacc    300

atccacggtg ctcgtgccta cgcggcattt tgcgaattcg ctgacacaac gccgtcc       357
```

<210> SEQ ID NO 103
<211> LENGTH: 1854
<212> TYPE: DNA
<213> ORGANISM: Mycobacteria tuberculosis

<400> SEQUENCE: 103

-continued

```
atgtcctatc tcgtcgtggt gccggagttg gtcgcagcgg cggcaacaga tttggcgaac     60
atcggttcgt cgattagtgc agccaacgcg gccgcggcgg caccgaccac ggcactggtc    120
gcagccggcg gcgacgaggt atcggcggcc atagccgcgt tgttcggagc gcatgctcgg    180
gcatatcaag cgttgagtgc ccaggcggcg atgtttcatg aacagtttgt ccgggccctc    240
gccgccggcg gtaactccta cgccgtcgct gaggcggcaa ccgcgcaatc ggttcagcaa    300
gatctgctca acctgatcaa tgcgcccacc caggcgctgt tggggcgtcc gctgatcggc    360
aacggcgcca acgggctgcc gggtacgggc cagaacggcg gcgacggcgg gattctgtac    420
ggcaacggcg gcaacggtgg gtccggcggg gtcaaccagg ccggtggcaa tggcgggaat    480
gctgggctgt ggggcaatgg cggatccggc ggagccggcg ggaacgccac cactgccggc    540
cgcaacggct tcaacggggg cgccggggga agcggcggtt tgctgtgggg caatggcggt    600
gccggcgggg ccggtgggaa cggcggtccg gctccgctcg tgggcggggt gggcaccacc    660
ggtggcgccg gcgggaacgg cggcggcgcc gggttgttct acggtttcgg cggcgccggt    720
gggaacggcg ggatgggcgg ggtggcaccg agcaccggcc cctcgatggg catcctcccg    780
gccggcggtg tcggcgggcc tggtggctcc ggcggggcga gcgcgcttgc cttcggctcc    840
ggcggcgtcg gcggtgccgg tggcttgggc gggccgaccg atggcaccgt ccagggggtg    900
ggcggcttcg gcggtcaggg cggcaacggc gggcagagcg gcttgttgtt tggcaacgcg    960
ggagccggcg gggcaggcgc tgccggcgga gccggcaccg gcgacaccga gagcttcggc   1020
ggccacggcg gggccggcgg tgatggcggc gctgttggct tgatcggtaa cggcggggcc   1080
ggcggcaccg gatctcccgg cgctgtggtg ggtggtaacg gcggcgtcgg tggtctgggt   1140
ggcgccggca gtcccggggg tctgttgtac ggcaccgggg gggccggcgg caatggcgga   1200
ccgggtggtg acggtggtac tggcgcgacg gtgggctttg ccggctccgg cggtttcggc   1260
ggtgcggggg gcatcgccca gctgtttggc acgggtggca tgggtggtag cggcggtggt   1320
ataggcgctg gcaccacgac cgtggtgccg cccgacgtcg ccccggtggg tggcacaggc   1380
ggcaatggcg gtcgcgccgg gctgctgttg ggtgtgggtg gcatgggcgg taatggcggt   1440
gccaccagcg tcggcgggac gctctacgcc gccggtggaa acggcggcga cggcgggttg   1500
gtgtggggca acggtggcac cggcgggagc ggtggcgccg gcggggcggg cagcgtcggc   1560
aacggcggtg cgggtggcaa cgcggcactg ctgttcggca acggcggggc gggcggggcc   1620
ggcggcgccg gcggcatcgg tgccggcgga gccggcggct tcggcgcggt tctgtttggc   1680
aacggcgggg ctggcgggag cggtgccccc ggtggcatcg gcgccggtgg caatggcgga   1740
aacgcgctgc tggtcggcaa cggcggcaac ggtggggcag gtaccggtgg ggctgctggc   1800
ggtgccggtg gctcgggcgg gttgctattc ggccaaaatg ggatgcccgg gccg          1854
```

<210> SEQ ID NO 104
<211> LENGTH: 1242
<212> TYPE: DNA
<213> ORGANISM: Mycobacteria tuberculosis

<400> SEQUENCE: 104

```
gtgcatgagg tggctgctcg tgagcaacgt tcggacgggc cgatgaggct ggatgcgcag     60
ggccgactgc agcgttacga ggaggcgttc gctgactacg atgcaccgtt tgcgttcgta    120
gatctcgacg cgatgtgggg caatgccgat caactgcttg cgcgcgccgg cgacaagccg    180
atccgggtgg cgtcgaagtc gctgcgttgc cgaccactgc aacgcgaaat ccttgatgcc    240
```

-continued

```
agtgagcgat tcgacgggct attgacgttc acgcttaccg agacgctgtg gcttgccggc    300

caaggtttct cgaacctgtt gttggcctac ccgccgaccg accgggcggc attgcgtgcg    360

cttggcgagc tgacggccaa ggacccggac ggggcgccga tcgtgatggt ggacagcgtg    420

gagcaccttg acctgatcga gcgcacgacc gacaagccgg tacggctgtg tctggatttc    480

gatgccggct attggcgcgc cggcgggcgg ataaaaattg gttccaagcg ctcgccgctg    540

cacaccccgg agcaggctcg cgcactcgcg gtggagatcg cgcggcggcc ggcgctaacg    600

ttggcggcgt tgatgtgcta cgaggcccac attgcgggcc tcggtgacaa cgtcgccggc    660

aagcgggtcc acaacgcgat catccgtcgg atgcagcgca tgtcgttcga agagctgcgc    720

gagcgtcgtg cccgggccgt cgagctggtg cgcgaggtcg ccgacatcaa gatcgtcaac    780

gccggtggca ccggcgactt gcagctggtt gcgcaggagc cgttgattac cgaagcgacc    840

gccggctcgg gtttttacgc gccgacactg ttcgactcgt attcgacgtt cacgctgcag    900

cccgcggcga tgttcgcgct gccggtatgc cgtcgtcccg gtgcaaagac cgtgaccgcg    960

ctcgggggtg gctatttagc cagcggggtc ggggcgaagg accgcatgcc gactccctac   1020

ctgccggtcg ggctgaagct caatgcgctg gagggaacgg gcgaagttca gacaccgcta   1080

tccggtgatg cagcccgacg gctgaagctt ggcgacaagg tctacttccg ccacaccaag   1140

gccggtgagc tgtgtgagcg gttcgaccat ctgcatctgg tccgtggcgc tgaagtagtc   1200

gacaccgtcc ccacctaccg gggtgaaggg cgcaccttcc tc                      1242
```

<210> SEQ ID NO 105
<211> LENGTH: 1284
<212> TYPE: DNA
<213> ORGANISM: Mycobacteria tuberculosis

<400> SEQUENCE: 105

```
atggacgagg cccacccggc tcacccggca gatgcggggc ggcccggtgg cccaattcaa     60

ggcgcgcgaa gaggagctgc catgacaccg atcaccgccc tgccgaccga gttggcggcc    120

atgcgcgagg tagtcgagac gctcgcaccc attgagcgtg ccgcgggcga gccgggtgag    180

cacaaggcgg ccgagtggat cgtcgagcgc ctgcgcacgg cgggcgcgca ggacgcgcgc    240

atcgaggagg agcagtacct cgacggctac ccgaggctgc acctcaagct gtcggtgatc    300

ggggtggcgg ccggcgtcgc gggcctgctc agcagacgtt tgcgcatccc cgccgcgctg    360

gccggggtgg gtgcggggct ggcaatcgcc gacgattgcg ccaacgggcc gcgcattgtg    420

cgcaaacgaa cggagacgcc ccggacgaca tggaacgcgg tagccgaggc cggtgatcct    480

gctggtcagc taacagttgt tgtgtgcgct caccacgacg ccgcgcacag cggcaagttt    540

ttcgaggctc atattgagga ggtaatggtc gagctgtttc ccgggattgt ggagcgcatc    600

gacacgcagc tgccgaactg gtgggggccg atcctcgcgc ccgcactcgc cggtgtcggc    660

gccctgcgcg gcagccggcc gatgatgatc gccggaacgg tgggtagcgc cctggccgcc    720

gctttgttcg ccgacatcgc gcgcagtccg gtcgtccccg gtgccaacga caatctctcc    780

gcggttgcgc tgctggtcgc gctggccgag cggctgcgcg agcggccggt gaagggcgtg    840

cgagtgttgc tcgtgtccct gggggccgag gaaacgttgc agggcgggat ctacgggttc    900

ctggcgcgac acaaacccga gctggaccgc gaccgcacat acttcctgaa cttcgacacc    960

atcggctcac ccgagctcat catgctcgag ggcgagggcc cgacggtcat ggaggactac   1020

ttctatcggc cattccggga tctggtcatc cgggcggccg agcgcgccga cgcgccgctg   1080

cggcgcggca tccggtcgcg caacagtacc gacgcggtgt tgatgagccg cgccggctac   1140
```

-continued ccgaccgcgt gctttgtgtc gatcaaccgg cacaagtcgg tggccaatta ccacctgatg 1200
tccgatacac ctgagaatct ctgctatgag acggtgtccc acgccgtcac cgtcgccgaa 1260
tccgtgatca gggagctggc ccga 1284

<210> SEQ ID NO 106
<211> LENGTH: 1284
<212> TYPE: DNA
<213> ORGANISM: Mycobacteria tuberculosis

<400> SEQUENCE: 106
atgagcccga tatggagtaa ttggcctggt gagcaagtct gcgcgccgtc ggcgatcgta 60
cggccgacct cggaggctga gctggccgac gtgatcgcgc aggcggcgaa aagaggcgag 120
cgggtacgcg cggttggcag cgggcattcg tttaccgaca tcgcctgcac ggacggggtc 180
atgatcgaca tgaccggcct gcagcgggtc ctcgacgtgg accagccgac tggcctggtg 240
acggtcgagg ggggcgcaaa gctacgtgcg ctgggacccc aattggcgca acgacggctc 300
ggcctggaga accagggtga cgtggatccc caatccatca ccggcgcgac cgcgaccgcg 360
acgcacggaa ccggggtgcg tttccagaat ctgtcggcgc ggatcgtttc gctgcggctg 420
gtcaccgcgg gcggggaagt gctcagtctg tccgaaggtg acgattacct ggcggcacgg 480
gtttccctcg gcgcgctagg agtgatctca caggtcaccc tgcagacggt tccgctattc 540
acgttgcatc gccatgatca gcgacgctcg ctggcgcaga cgctggagcg cctcgacgag 600
ttcgtggacg gtaatgacca tttcgagttt ttcgtattcc cttacgcaga taaggcgttg 660
acgcgcacca tgcatcgcag tgacgagcag cccaaaccca cgcccgggtg gcagcgcatg 720
gtcggcgaga acttcgagaa cgggggattg agcctgatct gccagaccgg ccgtcgtttt 780
cctagtgtgg cgccgcgact gaaccgcctg atgacgaaca tgatgtcgtc ctccaccgtg 840
caagaccgcg cctacaaggt ctttgcgacc caacgcaagg tcaggttcac cgagatggag 900
tacgcgatcc cgcgtgaaaa cgggcgcgag gcgctccagc gtgtcatcga ccttgtgcgc 960
cgtcgcagct tgccgatcat gtttccgatt gaggtgcgat tctccgcccc cgacgattcc 1020
ttcctgtcga ccgcatatgg gcgcgacact tgctacatcg cggttcatca atacgccggt 1080
atggagttcg aaagctactt ccgcgccgtc gaggagatca tggacgacta cgccggtcgg 1140
ccacactggg gtaaacgtca ctatcagacc gccgccacgc ttcgtgagcg ctatccgcag 1200
tgggatcggt tcgccgcggt tcgcgatcgc ctcgatccgg accgggtgtt tctcaacgac 1260
tacacccggc gcgttctcgg tccc 1284

<210> SEQ ID NO 107
<211> LENGTH: 309
<212> TYPE: DNA
<213> ORGANISM: Mycobacteria tuberculosis

<400> SEQUENCE: 107
ttgggttcaa caggaggtag ccaacccatg acggcgaatc gagggcccgc tgcaatctcg 60
agcggctcga actctggccg cgttctcgac accgcccggg gtatcctcat cgctcttcgg 120
cggtgccccg cagagaccgc gttcgacgag ttgcacaacg ccgctcaacg gcacagattg 180
ccggtcttcg aaatagcttg ggcactagtg catttggcgg tcgagggaag cacgccatgc 240
cggagcttcg tcgatgccca gtcggcggct cggcgggagt ggggtcagct ttttgcgcat 300
gcggcggcg 309

-continued

<210> SEQ ID NO 108
<211> LENGTH: 744
<212> TYPE: DNA
<213> ORGANISM: Mycobacteria tuberculosis

<400> SEQUENCE: 108
gtgccgccta cggaaggaaa gtcgacaacg aatcgcgacg aaggcatcca ggtgctccgt 60
cgcgccgtcg ccgcgctgga cgaaatagct gccgaaccgg gacacctgcg cctagtcgat 120
ctctgcgagc ggctggggct ggccaaatcg acgactcgac gcttgctggt cggcctggtc 180
gaggtggggc tggttagtgt cgattcgcac ggccgcttcg cactgggcga gcgtttgctg 240
ggattcggaa gtgtcaccgg agcccacata gccgcggcgt tccggccgac cgtcgagcga 300
gttgcccgcg cgaccgacgg cgaaacggtc gacctgtcgg tactgcgcgg ccagcgaatg 360
tggtttgtcg accagatcga atcgtcttac cggctgcgtg cggtctcagc cgtcgggctc 420
cgcttcccgt tgaacggaac cgcgaatgga aaagcggcgc tggctgctct cgacgacgcc 480
gacgccgagg ccgcgctctg ccgtctggat cccatggtgg ccgaaggtct acggcgcgag 540
atcgtcgaga tccggcgcac cggtatcgct ttcgaccgca acgagcacac cccagggata 600
tccgcggctg cgatcgcacg acgcgccctg ggcgacaacg tgatcgcgat ctcggtgccg 660
gcgcccaccg cacgatttct ggaaaaagag cagcgcataa tcgccgcgtt gcgcgccgcc 720
gcggactcgc cggactggac tcgc 744

<210> SEQ ID NO 109
<211> LENGTH: 1218
<212> TYPE: DNA
<213> ORGANISM: Mycobacteria tuberculosis

<400> SEQUENCE: 109
atggcatccg tcgcccaacc cgttaggcgc cgcccaaagg accggaagaa gcagattttg 60
gatcaggccg ttggactgtt catcgaacgt ggcttccatt cggtcaaatt ggaggacatt 120
gccgaggcgg ccggggtgac cgcgcgcgcg ttgtatcgcc actacgacaa caagcaggcg 180
ttgctcgccg aagcgatccg aaccggccag gatcagtacc agagcgcgcg tcgtctcacc 240
gagggcgaga cggagccgac gccgcggccg ttgaacgccg atctggaaga cctgatcgcc 300
gcggcggtcg cctctcgggc gttgacggtg ctgtggcagc gcgaggcccg ctacctcaac 360
gaggacgacc gcacggcggt ccggcgccgc atcaacgcga tcgtcgccgg catgcgtgac 420
agcgtgctgc tggaggtgcc cgatctgagt ccacagcatt cggagttgcg ggcgtgggcg 480
gtgtccagca ctttgaccag cctgggccgg cacagcctaa gcctgccggg cgaggaactg 540
aaaaagcttc tctaccaggc gtgtatggcc gcggcaagga cgcctcccgt ctgcgaattg 600
ccgccactgc cggccggtga tgccgcacgc gacgaggccg acgtgctgtt ctcccgctac 660
gagaccctgc tggccgcggg cgcgcggctg ttccgtgcgc agggctatcc ggccgtcaac 720
accagcgaaa tcggcaaggg agccggcatc gcgggcccgg ggctgtaccg ttcgttttct 780
tccaaacagg ccatcctgga cgcgctcatc cgccgcctcg acgagtggcg ctgcctggag 840
tgcatccgag cgctacgagc gaatcagcaa gcggcacaac ggttgcgcgg ccttgtccaa 900
gggcacgttc ggatcagctt ggacgctccg gatctggtgg cagtgtcggt caccgaactg 960
tcgcacgcct ctgtcgaagt acgcgacggc tacctgcgaa atcagggcga ccgcgaggcc 1020
gtgtggatcg acctcatcgg caagctggta cccgcgacca gtgtcgccca ggggcgactg 1080
ctggtcgcgg cggcgattag cttcatcgaa gacgtcgctc gcacctggca tctcacgcgc 1140

-continued

```
tacgccggag tcgccgacga gatcagtggc ctggcgctgg cgatcctgac cagcggggca   1200

ggtaacctct tgcgcgca                                                 1218


<210> SEQ ID NO 110
<211> LENGTH: 795
<212> TYPE: DNA
<213> ORGANISM: Mycobacteria tuberculosis

<400> SEQUENCE: 110

atggtaatcg tggccgacaa ggcggccggt cgggtcgctg atccggtctt gcggccggtg     60

ggcgcgctgg gcgatttctt cgcgatgacg ctcgacacgt ccgtgtgcat gttcaagccg    120

cctttcgcgt ggcgtgaata cctacttcag tgctggttcg tggcgcgggt gtcgacgctg    180

cctggggtgt tgatgacgat cccatgggcg gtgatctcgg ggtttctctt caacgtcttg    240

ctgaccgaca tcggtgccgc ggacttttcc ggcaccggct gtgcgatctt caccgtgaac    300

caaagcgccc cgatcgtcac ggtcttggtg gtcgcgggcg cgggcgccac cgccatgtgc    360

gccgatctgg gtgcgcgcac catccgtgag gaactcgacg cactgcgggt gatgggcatc    420

aacccgatcc aagcgctagc ggctccgcgc gtgctggcgg ccaccacggt gtcgttggcg    480

ctgaattcgg tggtgaccgc gacggggctg atcggcgcgt tcttttgctc ggtgtttctc    540

atgcacgtct cggcgggggc atgggtgacc gggcttacca cgctgaccca caccgtggac    600

gtcgtcattt cgatgatcaa ggcgacgttg ttcgggctga tggccggact gatcgcctgc    660

tataagggca tgtcggtcgg tggcggcccg gccggagtcg gccgggcggt gaacgaaacc    720

gtggtgtttg ccttcatcgt cttgttcgtg atcaacatcg tcgtcaccgc ggtcggcatc    780

ccattcatgg tgtcc                                                     795


<210> SEQ ID NO 111
<211> LENGTH: 813
<212> TYPE: DNA
<213> ORGANISM: Mycobacteria tuberculosis

<400> SEQUENCE: 111

atgacggcag cgaaagccct tgtaagcgaa tggaatcgga tgggatcgca gatgcggttc     60

ttcgtcggca cgctggccgg gattcccgac gccctcatgc actaccgcgg cgagctgctg    120

cgggtgatcg cgcaaatggg gttggggacc ggggttcttg cggtgatcgg tggaacggtc    180

gcgatcgtcg ggttcttggc gatgaccacc ggcgcgatcg tggccgtgca gggctacaac    240

cagttcgctt cggtgggtgt ggaggcgctg accggcttcg cgtcggcctt cttcaacacc    300

cgcgagattc agcccggaac cgtgatggtc gcgctagcgg ccaccgtcgg tgccggtacc    360

accgctgcgc tgggggcgat gcggataaac gaggagatcg acgcgctcga ggtgatcggc    420

atccgcagca tcagctacct ggcgagcacc cgggtgctgg ccggagtggt cgtggccgtc    480

cctctgttct gtgtgggact gatgacggcc tacctggccg cgcgcgtcgg caccaccgcc    540

atctatggcc aggggtcggg cgtgtacgac cactacttca acacgttcct gcgcccgacc    600

gacgtgctct ggtcgtcggt tgaagtcgtc gtggtcgctc tgatgatcat gctggtgtgc    660

acctattacg gctacgccgc acatggcggg ccggccgggg ttggcgaggc ggtcggccgg    720

gccgtgcgtg cctcgatggt cgtcgcgtcg atcgcaatcc ttgtcatgac gctggccatc    780

tacggccagt cgcccaactt tcacctggcg acc                                 813


<210> SEQ ID NO 112
```

-continued

<211> LENGTH: 1275
<212> TYPE: DNA
<213> ORGANISM: M. tuberculosis

<400> SEQUENCE: 112
atgagacgcg ggccgggtcg acaccgtttg cacgacgcgt ggtggacgct gatcctgttc 60
gcggtgatcg gggtggctgt cctggtgacg gcggtgtcct tcacgggcag cttgcggtcg 120
actgtgccgg tgacgctggc ggccgaccgc tccgggctgg tgatggactc cggcgccaag 180
gtcatgatgc gcggtgtgca ggtcggccgg gtcgcccaga tcggtcggat cgagtgggcc 240
cagaacgggg cgagcctcag actggagatc gaccccgacc agatccggta catcccggcc 300
aatgtcgagg cacagatcag cgccaccacc gcattcggtg ccaagttcgt cgacctggtg 360
atgccgcaaa acccaagtcg tgcacggctg tccgctgggg cggtactgca ttcgaagaac 420
gtcagcacgg aaatcaacac cgtcttcgaa aacgtcgtcg acctgctcaa catgatcgac 480
ccgctgaaac tgaacgccgt gctgaccgcg gtcgccgacg ccgttcgcgg gcaaggtgaa 540
cggataggcc aggccaccac cgacctcaac gaggtgctgg aggcactcaa cgcacgcggc 600
gacaccatcg gcggcaactg gcgatcgctc aagaacttca ccgacaccta tgacgcggcc 660
gcccaagaca tcctgacgat cctgaacgcc gccagcacca ccagtgcgac cgtcgtgaat 720
cattcgacgc agctggatgc cttgctactc aacgccatcg gactatccaa cgctggcacc 780
aacctgcttg gcagcagccg agacaatctc gtcggcgcgg ccgacatcct ggcgccgacc 840
acgagcctgc tgttcaagta caaccccgaa tacacctgct tcctgcaggg cgccaagtgg 900
tatctcgaca acggcggcta tgcggcctgg ggcggggccg acgggcgcac gctacaactc 960
gatgtggcgc tactgttcgg caacgacccc tatgtctatc cggacaacct gccggttgtc 1020
gcggccaagg ggggtcccgg cggaaggccg ggatgcgggc cattgccgga tgccacccac 1080
aacttcccgg tgcgccagct ggtcaccaac accggatggg gaaccgggct ggacatccgg 1140
cccaaccccg gcatcgggca tccctgctgg gccaactact tcccggtgac ccgcgcggtg 1200
cccgagccgc cgtcgatccg tcagtgcatc cccgggccgg cgatcgggcc caaccccgcg 1260
gcgggggagc agcca 1275

<210> SEQ ID NO 113
<211> LENGTH: 1026
<212> TYPE: DNA
<213> ORGANISM: Mycobacteria tuberculosis

<400> SEQUENCE: 113
atgagggaga acctgggggg cgtcgtggtg cgcctcggcg tcttcctggc ggtatgcctg 60
ctgacggcgt tcctgctgat tgccgtcttc ggggaggtgc gcttcggcga cggcaagacc 120
tactacgccg agttcgccaa cgtgtccaat ctgcgaacgg gcaagctggt gcgcatcgcc 180
ggcgtcgagg tcggcaaggt caccaggatc tccatcaacc ccgacgcgac ggtgcgggtg 240
cagttcaccg ccgacaactc ggtcaccctc acgcggggca cccgggcggt gatccgctac 300
gacaacctgt tcggtgaccg ctatttggcg ctggaggaag gggccggcgg actcgccgtt 360
cttcgtcccg gtcacacgat tccgttggcg cgcacccaac cggcgttgga tctggatgcc 420
ctgatcggtg gattcaagcc gctgtttcgt gcgctgaacc ccgagcaggt caacgcgctg 480
agcgaacagt tgctgcacgc gtttgccgga caggggccca cgatcgggtc attgctggcc 540
cagtccgcgg ccgtgaccaa caccctggcc gaccgtgatc ggctgatcgg gcaggtgatc 600
accaacctca acgtggtgct gggctcgctg ggcgctcaca ccgatcggtt ggaccaggcg 660

-continued gtgacgtcgc tatcagcgtt gattcaccgg ctcgcgcaac gcaagaccga catctccaac 720
gccgtggcct acaccaacgc cgccgccggc tcggtcgccg atctgctgtc gcaggctcgc 780
gcgccgttgg cgaaggtggt tcgcgagacc gatcgggtgg ccggcatcgc ggccgccgac 840
cacgactacc tcgacaatct gctcaacacg ctgccggaca aataccaggc gctggtccgc 900
cagggtatgt acggcgactt cttcgccttc tacctgtgcg acgtcgtgct caaggtcaac 960
ggcaagggcg gccagccggt gtacatcaag ctggccggtc aggacagcgg gcggtgcgcg 1020
ccgaaa 1026

<210> SEQ ID NO 114
<211> LENGTH: 1230
<212> TYPE: DNA
<213> ORGANISM: Mycobacteria tuberculosis

<400> SEQUENCE: 114
atgaaatcct tcgccgaacg caaccgtctg gccatcggca cagtcggcat cgtcgtcgtc 60
gccgccgttg cgctggccgc gctgcaatac cagcggctgc cgtttttcaa ccagggcacc 120
agggtctccg cctatttcgc cgacgccggc gggctgcgca ccggcaacac cgtcgaggtc 180
tccggctatc cggtgggaaa agtgtccagc atctcgctcg acggaccggg cgtgctggtg 240
gagttcaagg tcgacaccga cgtccgactc ggaaaccgca ccgaagtggc aatcaaaacc 300
aagggcttgt tgggcagcaa gttcctcgac gtcacccccc gcggggacgg ccgactcgat 360
tctccgatcc cgatcgagcg gaccacgtcg ccctaccaac tgcccgacgc ccttggcgat 420
ttggccgcca cgatcagcgg gttgcacacc gagcggctgt ccgaatcgct ggccaccctg 480
gcgcagacct ttgccgatac gccggcgcac ttccgcaacg ccatacacgg ggtggcccgg 540
ctcgcccaaa ccctcgatga gcgcgacaac caactgcgca gcctgctggc caacgcggcc 600
aaagccaccg gggtgctggc caaccgcacc gaccagatcg tcggcctggt gcgcgacacg 660
aatgtggtct tggcgcagct gcgcacccaa agcgccgccc tggaccggat ctgggcgaac 720
atctcggcgg tggccgaaca actgcggggc ttcatcgctg agaaccgcca gcagctgcgc 780
ccggcgctgg acaagctcaa cggggtgctg gctatcgtcg aaaaccgcaa agagcgtgtg 840
cggcaggcca tcccgctgat caacacctat gtcatgtcgc tgggtgagtc gctgtcgtcg 900
ggcccgttct tcaaggcata cgtggtgaac ctgctgccgg gtcagttcgt gcaaccgttc 960
atcagcgccg cgttctccga cctggggctc gacccggcca cgttgctgcc gtcgcagctg 1020
accgacccac cgaccggtca acccggaacc ccgccgttgc cgatgcccta cccgcgcacg 1080
ggccagggcg gtgagccgcg gctgacgctg cccgacgcga tcaccggcaa tcccggcgat 1140
ccgcgctatc cgtaccggcc ggagccgccc gcgccgccgc ccggcgggcc gccgcccggc 1200
ccgcccgcgc agcagccggg agaccaaccg 1230

<210> SEQ ID NO 115
<211> LENGTH: 1269
<212> TYPE: DNA
<213> ORGANISM: Mycobacteria tuberculosis

<400> SEQUENCE: 115
gtgacaacga aactcagacg tgcccgctcg gtgttggcga ccgccctggt gctggtcgcg 60
ggcgtgatcc tggccatgcg caccgccgac gccgccgccc gcacgaccgt ggtcgcctac 120
ttcgacaaca gcaacggtgt gttcgccggt gacgacgtgc tcattcgggg cgtgccggtg 180

-continued

```
ggcaagatcg tcaagatcga accgcaaccg ctgcgcgcca agatttcgtt ctggttcgac    240

cgcaaatacc gagtccccgc cgatgccgcc gcggcgatcc tgtcgccgca actggtgacc    300

ggccgggcca tccagctgac accgccgtat gccggcgggc cgaccatggc cgacggcaca    360

gtaatcccgc aagagcgcac cgtggtgccg gtggagtggg acgacttgcg ggcgcaactt    420

cagcggctga ccgcattgct gcagcccacc cggccgggcg gcgtcagcac gctgggtgcg    480

ctcatcaata ctgccgccga caacctgcgc gggcaaggcg ccaccatccg cgacaccatc    540

atcaaactgt cacaagcgat ttcggctctc ggtgaccaca gcaaagacat cttctccacc    600

gtgacgaacc tgtcgacgct ggtcacggcg ctgcatgaca gcgctgacct gctcgaacgg    660

ctcaaccaca acctggccgc ggtgacctcg ctgctggccg atggcccgga caagatcggt    720

caggcagccg aggacctcaa cgcggtcgta gccgacgtcg gcagcttcgc cgccgagcac    780

cgcgaggcga tcggcaccgc atcagacaag ctcgcgtcaa tcaccaccgc gctggtcgac    840

agcctcgacg acatcaagca gacgctgcat atcagcccga cggtgttgca gaacttcaac    900

aacatcttcg aaccggccaa cggcgcgctg accggcgcgc tggcgggcaa caacatggcc    960

aacccaatcg ccttcctgtg cggcgcgatc caggctgcct cccggctggg cggcgagcaa   1020

gcggccaaat tgtgcgtgca atacctggcg ccgatcgtga agaaccgcca gtacaactac   1080

ccgccgctgg gggcgaacct gttcgtcggg gcgcaggcca ggcctaacga ggtcacctac   1140

agcgaggact ggctgcggcc cgattacgtt gcaccagttg cggacacgcc gccagatccg   1200

gccgcggccg tgaccgtcga tcccgcgacc ggcctgcgcg gcatgatgat gccgccgggg   1260

ggtggctcg                                                           1269
```

```
<210> SEQ ID NO 116
<211> LENGTH: 1131
<212> TYPE: DNA
<213> ORGANISM: M. tuberculosis

<400> SEQUENCE: 116

gtgaggatcg gcctgaccct ggtgatgatc gcggccgtgg tagcgagctg cggctggcgc     60

gggctgaatt cgctgccgct gcccggcacg cagggcaacg gcccggggtc cttcgcggtc    120

caggcgcagc tgccggatgt caacaacatc cagccgaact cgcgggtgcg ggttgccgac    180

gtgacggtcg gccacgtcac gaaaatcgag cgccaaggct ggcacgcgtt ggtgaccatg    240

cggctggatg gcgacgtcga tttgcccgcc aacgcaacgg ccaagatcgg caccaccagc    300

ctgctgggtt cctaccacat cgagctggcg ccaccgaaag gcgaagcgcg gcaaggcaag    360

ctgcgcgacg gttcactcat tgcgctgtca cacggtagcg cctacccaag caccgagcag    420

acgctggcag cgctgtcgct ggtgctcaac ggcggcggac tgggccaggt tcaagacatc    480

accgaggcgt tgagcaccgc gtttgccggc cgtgagcacg atctgcgcgg gctgattggg    540

cagctggaca ccttcaccgc atacctcaac aaccagtccg gtgacatcat cgcggccacc    600

gacagcctca accgcctcgt cggcaagttc gccgaccagc aacccgtctt cgatcgggcc    660

ctggccacca tccccgacgc gctcgcggtg ctggccgatg agcgggacac gctcgtcgag    720

gctgccgagc agctgagcaa gttcagcgcc ctgaccgtcg actcggtcaa caagaccacc    780

gcgaacctgg tcaccgaact gcggcaactc ggaccggtgt tggagtcgct ggccaattcc    840

ggtccggcgc tgacccgatc gctgtccctg ctggccacgt tcccgttccc gaacgagacg    900

ttccaaaatt tccagcgcgg cgaatacgcc aacctgaccg cgatcgtcga cctcacgctc    960

agccgcatcg accagggcct gttgaccggc acccgctggg agtgtcatct gacccagctc   1020
```

-continued gagctgcagt ggggtcgcac cattgggcag ttccccagcc cgtgtaccgc gggctatcgg 1080
ggtaccccgg gcaatccgct gacgatcgcc taccgctggg atcaggggcc c 1131

<210> SEQ ID NO 117
<211> LENGTH: 1311
<212> TYPE: DNA
<213> ORGANISM: Mycobacteria tuberculosis

<400> SEQUENCE: 117
atgctgcatc taccgcgccg agtgatcgtt cagctggccg tctttaccgt gatcgcggtg 60
ggcgtgctgg ccatcacgtt cctgcatttc gtgaggctgc cggcgatgct tttcggcgtc 120
ggccgctaca cggtgacgat ggagctggtc gaagccggtg ggctgtatcg caccggcaat 180
gtcacctacc gcggctttga ggtgggccgg gtggcagcgg tgcggctcac cgacaccggg 240
gtgcaagcgg tgctggccct gaaatcgggc atcgatatcc cgtcggacct caaggccgag 300
gtgcacagcc acaccgcgat cggcgaaacc tacgtcgagt tgttgccgcg caacgccgcc 360
tcgccgccac tgaagaacgg cgatgtcatt gcgctggccg acacctcggt gccgcccgac 420
atcaacgacc tgctcagcgc ggccaacacc gcattggagg caatacctca cgagaacctg 480
cagaccgtca tcgacgagtc gtacaccgcg gtggccgggt tagggctcga actttcccgg 540
ctgatcaagg gctcggcgga actggcgatc gatgctcgcg cgaatctcga tccgctggtg 600
gcgctgatcg accgggcagg accggtgctg gattcgcaga cccacacctc ggatgcgatc 660
gcggcctggg cggcacagct ggccgcagtc accggccaat tgcagacaca cgactcggcg 720
gtcggcgatc tcatcgaccg gggcggtccg gcgttggggg agacgcgcca actgctcgag 780
cggctacaac ccaccgtgcc catcctgctg gccaacctgg tcagcgtcgg ccaggtcgca 840
ctcacctatc acaacgacat cgaacagctg ctggtggtgt tccccatggc catcgccgcc 900
gaacaggccg gcatcctggc caacctcaac accaagcagg cctaccgggg ccagtatctg 960
agcttcaacc tcaacctgaa cctgccgccg ccgtgcacca ccggctttct gccggcccag 1020
cagcggcgca ttcccacgtt cgaggactac ccggatcgcc cggccggtga tctgtactgc 1080
cgggtgcccc aggattcgcc gtttaacgtg cgcggcgccc gcaacatccc ctgtgaaacc 1140
gtgccgggca agcgcgcacc caccgtgaag ttatgcgaga gcgacgcgcc atacctgccg 1200
ctgaacgacg gctacaactg gaagggcgac cccaacgcca cggtgccggg tttggggtcc 1260
ggccaggaca tcccgcagac atggcaaacg atgctgctgc cgccgggcag c 1311

<210> SEQ ID NO 118
<211> LENGTH: 573
<212> TYPE: DNA
<213> ORGANISM: Mycobacteria tuberculosis

<400> SEQUENCE: 118
atgtcggtag cagtggattc cgacgccgag gatgacgccg tatcggagat cgctgaggca 60
gccggcgtgt cgccggcccc agccaaacca tccatgtcgg cgccgcggcg catgctgctg 120
ttcggcctgg tcgtcgtcgt cgctttggcg gtgctgttgt gttgctgggg atttcgcgtc 180
cagcgggcac gccatgcgca ggaccagcgt ggtcacttcc tgcaagcggc ccggcagtgc 240
gcgctgaacc taacgaccat cgactggcgc aacgccgagg cggatgtgcg ccgcattctg 300
gacggcgcca caggcgagtt ttacaacgac ttcgcccagc ggtcccagcc cttcgtcgaa 360
gtactgaggc acgcaaaggc cagcacggtc ggcacgatca ccgaggccgg gctgcagacg 420

-continued

```
cagaccgccg acacggccca ggcgctggtg gcggtgtccg tgcaaacgtc gaatgccggc    480

gaagccgacc cggttccacg agcgtggcga atgcgcatca ccgtgcagcg ggtcggcgac    540

cgggtcaagg tgtccgacgt cgggttcgtg ccg                                 573
```

<210> SEQ ID NO 119
<211> LENGTH: 480
<212> TYPE: DNA
<213> ORGANISM: Mycobacteria tuberculosis

<400> SEQUENCE: 119

```
gtgagctggt cgcgggtgat cgcctacggg ctgctgcccg ggctggcgtt ggcgctgacg     60

tgtggcgcgg gcttgctgaa atggcaggac ggcgccgtcc gcgacgccgc ggttgcccgt    120

gcggaatccg tgcgggccgc gaccgacggc accaccgcgc tgctgtctta ccggcccgac    180

accgtgcagc atgacctcga gagcgcgcga agcaggctca cgggcacgtt cctcgacgcc    240

tacacacagc tgacccacga cgtggtgatc cccggcgcac agcagaagca gatctcggcc    300

gtggccaccg tcgcggccgc ggcgtcggtg tcgacttccg ccgaccgcgc cgtcgtcctg    360

ctgttcgtaa accagaccat caccgtcggc aaggacgcgc cgaccaccgc cgcttccagc    420

gttcgggtga ccctcgacaa catcaacggg cgttggctga tctcgcaatt cgaaccgatc    480
```

<210> SEQ ID NO 120
<211> LENGTH: 375
<212> TYPE: DNA
<213> ORGANISM: Mycobacteria tuberculosis

<400> SEQUENCE: 120

```
gtgcagcgcc aatcattgat gccccagcag acccttgccg ccggcgtttt cgtgggtgcg     60

ctgctatgcg gtgtcgtgac ggcggcggtg ccaccacacg cacgcgccga cgtggtcgcc    120

tatctggtca acgtgacggt acgcccgggc tacaacttcg ccaacgccga cgccgcgttg    180

agttacggac atggcctctg cgagaaggtg tctcggggcc gcccttacgc acagatcatc    240

gccgacgtca aggctgattt cgacacccgc gaccaatacc aggcctcgta tctgctcagc    300

caggctgtca acgaactctg ccccgcgctg atctggcagt tgcgaaactc cgcagtcgac    360

aatcggcgct cgggc                                                     375
```

<210> SEQ ID NO 121
<211> LENGTH: 663
<212> TYPE: DNA
<213> ORGANISM: Mycobacteria tuberculosis

<400> SEQUENCE: 121

```
atgtcgcgtc gagcatcggc cacgtgtgcc ttgtccgcga ccaccgccgt cgccataatg     60

gctgctcccg ccgcacgggc cgacgacaag cggctcaacg acggcgtggt cgccaacgtc    120

tacaccgttc aacgtcaggc cggctgcacc aacgacgtca cgatcaaccc gcaactacaa    180

ttggccgccc aatggcacac cctcgatctg ctgaacaacc ggcacctcaa cgacgacacc    240

ggttctgacg gatccacacc gcaagaccgc gcgcatgccg ccggcttccg cgggaaagtc    300

gctgaaaccg tggcgatcaa tcccgccgta gcgatcagcg gcatcgagtt gataaaccag    360

tggtactaca accccgcgtt tttcgcgatc atgtccgact gcgccaacac ccagatcggg    420

gtgtggtcag aaaacagccc ggatcgcacc gtcgtggtgg ccgtttacgg acagcccgat    480

cgaccttccg cgatgccgcc caggggagcg gtaaccggac cgccgtcccc ggtggccgcg    540

caagagaacg ttcctatcga ccccagcccc gactacgacg ccagcgacga gatcgaatac    600
```

-continued

```
ggcatcaact ggctgccatg gatcctgcgc ggcgtgtacc cgccgcccgc aatgccgccg    660

cag                                                                  663


<210> SEQ ID NO 122
<211> LENGTH: 405
<212> TYPE: DNA
<213> ORGANISM: Mycobacteria tuberculosis

<400> SEQUENCE: 122

gtgcggtgga ttgtcgacgg tatgaacgtg atcggaagtc gtccggatgg ttggtggcgc     60

gaccgccatc gcgcgatggt gatgctggtg gaaaggctcg aggggtgggc catcaccaag    120

gctcggggcg acgacgtgac ggtggtgttc gagcggccgc cgtcgaccgc catcccgtca    180

tcggtggtcg aagtggcgca tgcgcccaag gcggccgcca actcggccga cgacgagatc    240

gtccggctgg tccgatccgg cgcccagcca caagagattc gtgtggtgac atcggacaaa    300

gcgttgaccg accgggtccg agacttgggt gcggcagtct acccggcaga acggttccgt    360

gaccttatcg acccgcgcgg gtcgaacgcg gcccgccgca cgcag                    405


<210> SEQ ID NO 123
<211> LENGTH: 1044
<212> TYPE: DNA
<213> ORGANISM: Mycobacteria tuberculosis

<400> SEQUENCE: 123

atgtctcaga cacccgctac aacccgcaaa acgtttcccg agatcagctc aagagcgtgg     60

gagcaccccg ccgaccggac cgccctttcc gcgctgcgcc ggctcaaagg cttcgaccag    120

atcttgaagc tgatgtcggg gatgttgcgg gaacggcagc accggctgct gtacctggcc    180

agcgcggcac gggtcgggcc gcggcagttc gccgacctcg acgcgctgct ggacgaatgc    240

gtggatgtgc tggacgcgtc ggcgaaaccc gaactctacg tgatgcagtc accaatcgcg    300

gatgccttca ccatcggcat gggcaagcca ttcaccgtga tcacctcggg gctgtacgac    360

ctggtgacac acgacgagat gcggttcgtg atgggccacg agctcggcca cgcactgtcc    420

ggccacgcgg tgtaccgcac gatgatgatg catctgctgc ggttggcccg gtcattcggc    480

gtcttgccgg ttggcggctg ggcgctgcgc gcaatcgtgg ctgcgctgct ggaatggcag    540

cgcaaatcgg agctgtccgg cgatcgcgct gggttgctgt gcgcgcagga tttggacacc    600

gcgctcaggg tggagatgaa gctcgctggc ggctgccggc tggacaagct ggactcggag    660

gccttcttgg ctcaggcccg ggaatacgag acatccggcg atatgcgcga cggggtgctc    720

aagctgctca acctggagct gcagacccat ccgttctctg tgctgcgggc tgccgccttg    780

actcactggg tggacaccgg cggctatgcc aaggtgatag ccggcgagta cccgcgtcgg    840

gccgacgacg gcaacgccaa atttgcagac gaccttggcg cggccgcccg gtactaccgg    900

gacggcttcg accagtccaa cgacccgctg atcaaaggta tccgcgacgg attcggtggc    960

atcgtcgagg gcgtgggacg ggcagcctcg aacgcggccg attcattggg ccgcaagatc   1020

accgagtggc ggcagccctc gaag                                          1044


<210> SEQ ID NO 124
<211> LENGTH: 564
<212> TYPE: DNA
<213> ORGANISM: Mycobacteria tuberculosis

<400> SEQUENCE: 124
```

-continued

```
atgactacgc gtccggcaac cgaccgccgc aagatgccca ctgggcggga agaggtagcg     60

gccgcaatcc tgcaggccgc caccgacctg ttcgccgagc gtgggccagc cgcgacgtcg    120

attcgcgaca tcgccgctcg atccaaggtc aaccacgggc tggtgtttcg tcacttcggc    180

accaaggacc aactggttgg ggccgtgctc gatcacctgg gcacgaagct gaccagactg    240

ttgcactccg aggcgcccgc tgacatcatc gaacgggctc tcgaccgaca tgggcgggtc    300

ttagcccggg cactgctgga cggatatccc gtgggccagc tgcaacagcg atttcccaat    360

gttgcggagc tgctcgacgc ggtacggcct cgctacgaca gcgacttggg cgcgcggctg    420

gcggtcgcgc acgcccttgc gctgcaattc ggttggcggc tctttgcgcc catgctgcgc    480

tcggcgacgg gtatcgacga gctgaccggt gacgaactac ggctgtccgt gaacgatgcg    540

gtagcccgga tcctggaacc gcac                                           564
```

<210> SEQ ID NO 125
<211> LENGTH: 702
<212> TYPE: DNA
<213> ORGANISM: Mycobacteria tuberculosis

<400> SEQUENCE: 125

```
gtgacgatat tgatcctgac cgacaacgtc cacgcccatg ctctggcggt cgatctgcag     60

gccaggcatg gcgatatgga cgtctatcag tcccccatcg gccagctgcc gggtgtcccg    120

cgatgtgatg tcgcagagcg cgtcgcggaa atcgtggagc ggtatgacct cgtcctttcc    180

ttccactgta aacagaggtt tcccgccgct ttgatcgatg ggtcaggtg tgtgaatgtt    240

catccgggtt tcaaccccta caaccgcggc tggtttcccc aggtcttctc gatcatcgac    300

gggcaaaaag tcggcgtgac gatccacgag atcgacgatc agttggacca tggtccgatc    360

atcgcccagc gggaatgcgc gatcgagtcg tgggattcct cgggaagtgt ctacgcccgg    420

ctgatggaca tcgagcgtga gttggtgctg gaacatttcg acgccatccg ggacggcagc    480

tacacggcta aatcgccggc caccgagggc aacctcaacc tgaaaaagga tttcgaacaa    540

ctccggcggc tagacctgaa cgagcgcgga acgtttgggc atttcctgaa tcgcctgcgc    600

gcgttgaccc atgatgattt ccgcaacgct tggttcgtcg atgcgtcagg ccgcaaggtg    660

tttgtccgcg tcgtgctcga accggagaag cccgcggaag cc                       702
```

<210> SEQ ID NO 126
<211> LENGTH: 1599
<212> TYPE: DNA
<213> ORGANISM: Mycobacteria tuberculosis

<400> SEQUENCE: 126

```
atgttagcct tcccttattt gatgactatg atcactccac ctaccttcga cgttgcgttc     60

atcggcagcg gggccgcgtg ctctatgact ctgctggaaa tggccgatgc cctgctgagc    120

agcccctcgg catcgcccaa gttgcgcatc gcggtggtgg agcgagacga gcagttctgg    180

tgcggaatcc cctatggcca acgctccagc atcggatcgc tggccattca gaagctcgac    240

gatttcgccg acgagccgga aaaggccgcc taccggatct ggctggagca gaacaagcag    300

cgctggctgg cgttcttcca ggcagagggc ggtgcggccg cggcccgctg gatctgcgac    360

aaccgcgacg cattggacgg caaccagtgg ggggagctct acctgccgcg gtttctcttc    420

ggtgtatttc tgtcggagca gatgattgcc gccatcgccg cgctcggcga gcgtgacctg    480

gccgaaatcg tcaccatccg cgctgaggcc atgagcgccc actccgcaga cggccactac    540

cgaatcggcc tccgcccgtc tggaaacggt ccaacggcaa ttgctgcagg caaagtggtt    600
```

-continued gtggccattg gcagccccc gaccaaagcc atccttgcga gcgattccga acccgcattc 660
acctatatca acgatttcta ctcccccggc ggggagagca acgttgcgcg actgcgcgat 720
tcgctcgacc gcgtcgagtc gtgggagaag cgcaacgtac tggtcgtggg ttccaacgcc 780
acctcgctgg aagcgctcta cctaatgcgt cacgacgcgc gcatccgcgc acgcgtccgg 840
tccatcaccg tcatctcgcg ctccggcgtg ctgccctaca tgatctgcaa tcagccgccg 900
gagtttgact tcccgcggct gcgcacgctg ctctgtacgg aagcgatcgc cgcggcggat 960
ctcatgtccg cgatccgcga cgatctcgcg acggccgaag aacgctcgtt gaacctggcc 1020
gatttgtacg acgccgttgc cgccctgttt gggcaggcgc tgcacaagat ggatctcgtg 1080
cagcaggaag agttcttctg cgtgcacggc atgaacttca ccaagttggt gcggcgtgcg 1140
ggacgcgatt gccgccaggc atccgaggag ctagccgcgg acggcacgct gagcctgctc 1200
gccggcgaag tactgcgcgt ggatgcctgc gcgtccggcc agccgttcgc caccatgacc 1260
taccgagccg cgggagccga gcatacccac cccgtcccct tcgctgcggt ggtgaattgt 1320
ggcggtttcg aggagctgga cacgtgttcc tcgccgttcc tggtcagcgc gatgcagaac 1380
gggctgtgcc gcccgaaccg caccaaccgt ggccttctgg ttaacgacga cttcgaggcc 1440
agcccaggtt tttgcgtcat cgggccccta gtcggcggca atttcactcc caagatccgt 1500
ttttggcacg tcgagagcgc accgcgcgtc cggtcgctgg cgaaatcgct ggcggccagc 1560
ctgcttgctt cgctccagcc cgtcgcactg gccccatgc 1599

<210> SEQ ID NO 127
<211> LENGTH: 1236
<212> TYPE: DNA
<213> ORGANISM: Mycobacteria tuberculosis

<400> SEQUENCE: 127
atgaagatcc gaacgttatc cggctcggtg ctggagccgc cgtccgcagt acgcgcgacc 60
ccaggcacgt ccatgttaaa actcgagccg ggtggctcga cgatccccaa gatccccttc 120
atccgcccga gctttcccgg gccagccgag ctcgccgagg acttcgtaca gatcgcccag 180
gctaactggt acacgaactt cggtccgaac gagcggcggt ttgcccgcgc cctgcgcgac 240
tatctgggac ctcatctgca cgttgctacc ctcgccaacg gcaccctggc actcctcgcg 300
gcgctccacg tcagtttcgg cgccggtacg cgggaccgct acctgctgat gccgtcgttc 360
acgttcgtcg gcgtggctca ggctgcgcta tggactgggt accgtccctg gttcatcgac 420
atcgacgcca acacatggca gccatgcgtc cactccgccc gcgccgtcat cgaacgcttc 480
cgcgaccgga tcgccggcat cctgctggcc aatgtgttcg gcgtcggcaa tccccagatc 540
agcgtctggg aggagctcgc cgccgaatgg gagctaccga ttgtgctcga ctcggcggcc 600
ggcttcggct ccacgtacgc cgacggcgag cgcctcggtg gacgcggtgc atgcgagatc 660
ttctccttcc atgcgaccaa gccgttcgcg gttggtgagg gcggcgctct ggtttctcgc 720
gatccacggc tcgtcgagca cgcatacaag ttccagaact tcggcttggt gcaaacacgc 780
gagtccatcc agctcggaat gaacggcaag ctgtcggaga tcagcgccgc tattggccta 840
cgccaactag tcgggcttga tcgccgcctg gcaagtcgcc gcaaggtcct cgagtgctat 900
cgcaccggta tggccgacgc gggtgtgcgt ttccaggaca acgccaatgt tgcgtcgctc 960
tgtttcgcga gcgcttgctg cacgtccgcc gaccacaagg ccgcggttct gggtagcctg 1020
cgtaggcacg cgatcgaggc gcgcgactac tacaacccac cgcagcaccg acatccgtac 1080

-continued

```
tttgtgacga atgccgagtt agtcgagtcg accgatctag ccgtcacggc ggacatttgc   1140

tcgcgaatcg tgtcgctgcc agtccacgac cacatggccc cggatgacgt tgcccgggtc   1200

gtcgccgccg tgcaggaagc ggaggtgcgc ggtgaa                             1236
```

<210> SEQ ID NO 128
<211> LENGTH: 2358
<212> TYPE: DNA
<213> ORGANISM: Mycobacteria tuberculosis

<400> SEQUENCE: 128

```
atgatcaccg aggacgcctt ccccgtcgaa ccgtggcagg tccgcgagac caagctcaac     60

ctgaacctgc tggcccagtc cgaatcccta ttcgccttgt ccaacgggca cattggatta    120

cgcggcaacc tcgacgaggg cgaacccttc ggactgccgg gcacctacct gaactctttc    180

tacgaaatcc ggccgctgcc gtacgccgag gccggttatg gatatccgga ggccggccag    240

accgttgtcg acgtcaccaa cggcaagatc tttcgcctgt tggtcggcga cgagccgttc    300

gacgtccggt atggcgaatt gatctcccac gaacggatcc tcgacctgcg cgccgggacg    360

ctgacccgcc gcgcgcactg gcgctcaccg gcgggcaagc aagtcaaagt gacgtccacc    420

cggctggtgt cgctggccca ccgcagcgtc gcggcgatcg agtacgtcgt cgaggcaatc    480

gaggaattcg ttcgcgtgac cgtgcagtcc gaactcgtca ccaacgagga cgtaccggag    540

acctcggccg acccgcgggt gtcggccatc ctggacaggc cgctacaggc cgtcgagcac    600

gaacgcaccg agcggggtgc acttctcatg caccgcaccc gagccagcgc gctgatgatg    660

gccgcaggga tggaacacga ggtcgaggtt cccgggcggg tcgagatcac caccgacgcc    720

cgcccggacc tggcccgaac caccgtgatc tgcgggctgc gcccgggaca gaagctgcgc    780

atcgtcaaat acctggccta tggctggtcc agcctgcgct cccgcccggc gctgcgcgac    840

caggccgccg gcgcgctgca cggtgcccgc tacagcggct ggcaggggct gctggacgcg    900

caacgcgcct acctcgacga cttctgggac agcgcggacg tggaggtcga gggcgacccg    960

gaatgtcagc aagcggtgcg tttcgggtta tttcacctgt tgcaggccag cgcgcgcgcc   1020

gaacgccgcg cgatccccag caaggggctc accggaaccg ggtatgacgg ccacgccttt   1080

tgggacaccg aaggtttcgt gctaccggtg ctcacctaca ccgcaccgca tgcggtcgcc   1140

gacgcgctgc ggtggcgggc gtcgacgttg gacctggcca aggagcgggc ggccgagctc   1200

ggcctggaag gtgccgcctt tccctggcgg accatccgcg gacaggagtc ctcggcctac   1260

tggccggccg gcacggcggc ctggcacatc aacgccgaca tcgcgatggc gttcgagcgg   1320

taccgcatcg tcaccggcga cggttcgctg gaggaggaat gcggccttgc ggtgctgatc   1380

gagaccgccc ggctgtggct ctcgctcggg caccacgacc gccacggcgt ctggcacctc   1440

gacggggtca ccggtcccga cgagtacacg gcggtcgtcc gcgacaacgt gttcacgaat   1500

ctgatggcgg cgcacaatct gcacaccgcc gccgatgctt gcttgcgcca ccccgaggcg   1560

gcggaggcca tgggtgtcac caccgaggag atggccgcct ggcgcgacgc ggccgacgcc   1620

gccaacattc cctacgacga ggaactcggt gtccaccagc agtgtgaagg gttcaccacc   1680

cttgcggagt gggatttcga agccaacacc acttatccgt tgctactgca cgaggcctac   1740

gtgcgcttgt atcccgcaca ggtgatcaag caggccgacc tggtgctggc gatgcagtgg   1800

cagagtcacg cgttcacgcc cgagcagaag gcgcgcaacg tcgactacta cgaacggcgc   1860

atggtgcgcg actcgtcgtt gtcggcctgc actcaggcgg tgatgtgcgc cgaggtcggc   1920

catctcgagt tggcccacga ctatgcctac gaagccgccc tgatcgacct gcgcgacctg   1980
```

-continued

```
caccgcaaca cccgtgacgg cctacacatg gcttcgctgg ccggagcctg gacggcgctg   2040

gtcgtaggct tcggcggcct acgcgacgac gagggcatcc tgtccatcga tccgcagctg   2100

cccgacggca tctcgcggct gcggttccgg ctgcgatggc gcggcttccg gctgatcgtc   2160

gacgccaacc acaccgacgt caccttcatc cttggcgacg gtcccggcac ccagctgacc   2220

atgcgccacg ccggccaaga tctgacgctg cacacggaca caccgtccac catcgccgtg   2280

cgcacccgta agccgctgct gccgccacca ccgcagccgc caggccgcga gccagtgcac   2340

cgccgggctt tagcccgg                                                 2358
```

<210> SEQ ID NO 129
<211> LENGTH: 786
<212> TYPE: DNA
<213> ORGANISM: Mycobacteria tuberculosis

<400> SEQUENCE: 129

```
atggcgaact ggtatcgccc gaactatccg gaagtgaggt cccgcgtgct gggtctgccc     60

gagaaggtgc gtgcttgcct gttcgacctc gacggtgtgc tcaccgatac cgcgagcctg    120

cataccaagg cgtggaaggc catgtttgac gcctacctag ccgagcgagc cgagcgcacc    180

ggcgaaaaat tcgttccctt cgaccctgcc gcggactatc acacgtatgt ggacggcaag    240

aaacgcgaag acggcgttcg atcgtttctg agcagccgcg ccatcgaaat acccgacggt    300

tccccggatg acccgggcgc cgccgagacg gtgtatggcc tgggcaaccg caagaacgac    360

atgttgcaca agctgctgcg cgacgatggg gcccaggtgt tcgacgggtc gcggcgctac    420

ctggaggcgg tcacggccgc gggtctcggt gtggccgtgg tgtcttcgag cgccaacacc    480

cgcgacgtgc tcgcgaccac cggtctggac cggttcgtcc agcagcgggt ggacggcgtg    540

acgttgcgcg aagagcacat cgccggcaag ccggcccccg actccttcct gcgcgcggca    600

gaactgttgg gggttacccc cgacgcggcg gcggtgttcg aggacgccct gtccggggtg    660

gcggccggcc gcgccggcaa cttcgccgta gtggtgggca tcaaccgaac gggccgggcg    720

gctcaggccg cccagttgcg ccgccatggc gccgacgtgg tggtaaccga tctcgccgag    780

ctgctg                                                               786
```

<210> SEQ ID NO 130
<211> LENGTH: 60
<212> TYPE: DNA
<213> ORGANISM: M. tuberculosis
<220> FEATURE:
<221> NAME/KEY: misc_feature
<222> LOCATION: (1)...(60)
<223> OTHER INFORMATION: n = A,T,C or G
<220> FEATURE:
<221> NAME/KEY: misc_feature
<222> LOCATION: 2, 55
<223> OTHER INFORMATION: n = A,T,C or G

<400> SEQUENCE: 130

```
antagtaatg tgcgagctga gcgatgtcgc cgctcccaaa aattaccaat ggttnggtca     60
```

<210> SEQ ID NO 131
<211> LENGTH: 60
<212> TYPE: DNA
<213> ORGANISM: M. tuberculosis

<400> SEQUENCE: 131

```
agtagtaatg tgcgagctga gcgatgtcgc cgctcccaaa aattaccaat ggtttggtca     60
```

-continued

```
<210> SEQ ID NO 132
<211> LENGTH: 60
<212> TYPE: DNA
<213> ORGANISM: M. tuberbulosis

<400> SEQUENCE: 132

tgacgccttc ctaaccagaa ttgtgaattc atacaagccg tagtcgtgca gaagcgcaac     60


<210> SEQ ID NO 133
<211> LENGTH: 60
<212> TYPE: DNA
<213> ORGANISM: M. tuberculosis

<400> SEQUENCE: 133

tgacgccttc ctaaccagaa ttgtgaattc atacaagccg tagtcgtgca gaagcgcaac     60


<210> SEQ ID NO 134
<211> LENGTH: 11
<212> TYPE: DNA
<213> ORGANISM: M. tuberculosis

<400> SEQUENCE: 134

actcttggag t                                                          11


<210> SEQ ID NO 135
<211> LENGTH: 11
<212> TYPE: DNA
<213> ORGANISM: M. tuberculosis

<400> SEQUENCE: 135

actcttggag t                                                          11


<210> SEQ ID NO 136
<211> LENGTH: 49
<212> TYPE: DNA
<213> ORGANISM: M. tuberculosis
<220> FEATURE:
<221> NAME/KEY: misc_feature
<222> LOCATION: (1)...(49)
<223> OTHER INFORMATION: n = A,T,C or G
<220> FEATURE:
<221> NAME/KEY: misc_feature
<222> LOCATION: 15, 24
<223> OTHER INFORMATION: n = A,T,C or G

<400> SEQUENCE: 136

gtggcctaca acggngctct ccgnggcgcg ggcgtaccgg atatcttag                 49


<210> SEQ ID NO 137
<211> LENGTH: 49
<212> TYPE: DNA
<213> ORGANISM: M. tuberculosis

<400> SEQUENCE: 137

gcggcctaca acggcgctct ccgcggcgcg ggcgtaccgg atatcttag                 49
```